(12) United States Patent
He

(10) Patent No.: US 11,162,143 B2
(45) Date of Patent: Nov. 2, 2021

(54) METHODS FOR GENERATING THERAPEUTIC DELIVERY PLATFORMS

(71) Applicants: The University of Kansas, Lawrence, KS (US); Kansas State University Research Foundation, Manhattan, KS (US)

(72) Inventor: Mei He, Gainesville, FL (US)

(73) Assignees: The University of Kansas, Lawrence, KS (US); Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 17/236,561

(22) Filed: Apr. 21, 2021

(65) Prior Publication Data

US 2021/0268121 A1 Sep. 2, 2021

Related U.S. Application Data

(63) Continuation-in-part of application No. PCT/US2019/057237, filed on Oct. 21, 2019.

(60) Provisional application No. 63/148,781, filed on Feb. 12, 2021, provisional application No. 62/748,470, filed on Oct. 21, 2018.

(51) Int. Cl.
| | |
|---|---|
| *G01N 27/00* | (2006.01) |
| *B03C 5/00* | (2006.01) |
| *G01N 27/12* | (2006.01) |
| *C12Q 1/6886* | (2018.01) |
| *A61K 47/69* | (2017.01) |
| *G01N 33/574* | (2006.01) |
| *G01N 33/543* | (2006.01) |
| *B03C 1/015* | (2006.01) |
| *B03C 1/30* | (2006.01) |
| *B01L 3/00* | (2006.01) |
| *A61K 49/00* | (2006.01) |

(52) U.S. Cl.
CPC ........ *C12Q 1/6886* (2013.01); *A61K 47/6901* (2017.08); *A61K 49/0097* (2013.01); *B01L 3/502715* (2013.01); *B01L 3/502761* (2013.01); *B03C 1/015* (2013.01); *B03C 1/30* (2013.01); *G01N 33/5434* (2013.01); *G01N 33/54333* (2013.01); *G01N 33/574* (2013.01); *C12Q 2600/156* (2013.01); *C12Q 2600/158* (2013.01); *C12Q 2600/178* (2013.01); *G01N 2446/80* (2013.01)

(58) Field of Classification Search
None
See application file for complete search history.

(56) References Cited

U.S. PATENT DOCUMENTS

| | | | |
|---|---|---|---|
| 6,472,541 B2 | 10/2002 | Tsien et al. | |
| 6,806,050 B2 | 10/2004 | Zhou et al. | |
| 8,186,913 B2 | 5/2012 | Toner et al. | |
| 8,895,292 B2 | 11/2014 | Söderlund et al. | |
| 8,986,944 B2 | 3/2015 | Yamanishi et al. | |
| 9,534,216 B2 | 1/2017 | Link et al. | |
| 10,130,949 B2 | 11/2018 | Viovy et al. | |
| 10,150,116 B2 | 12/2018 | Kapur et al. | |
| 10,350,599 B2 | 7/2019 | Zhao et al. | |
| 10,788,486 B2 | 9/2020 | Zhang et al. | |
| 2008/0302732 A1 | 12/2008 | Soh et al. | |
| 2010/0105120 A1 | 4/2010 | Zebala | |
| 2010/0165784 A1 | 7/2010 | Jovanovich et al. | |
| 2012/0183575 A1 | 7/2012 | Gabrielsson | |
| 2014/0154703 A1 | 6/2014 | Skelley et al. | |
| 2017/0001197 A1 | 1/2017 | He et al. | |
| 2017/0065978 A1 | 3/2017 | Zhao et al. | |
| 2017/0160294 A1 | 6/2017 | Neurauter et al. | |
| 2017/0165667 A1 | 6/2017 | Beaumont et al. | |
| 2018/0100853 A1 | 4/2018 | Zhang et al. | |
| 2018/0143188 A1 | 5/2018 | Stein et al. | |
| 2018/0346969 A1 | 12/2018 | Chang et al. | |
| 2019/0025330 A1* | 1/2019 | John | G01N 33/54313 |
| 2019/0049434 A1 | 2/2019 | Blainey et al. | |
| 2019/0145980 A1 | 5/2019 | Kang et al. | |
| 2019/0170741 A1 | 6/2019 | Alix-Panabieres et al. | |
| 2019/0276820 A1 | 9/2019 | Gaige et al. | |

FOREIGN PATENT DOCUMENTS

| | | |
|---|---|---|
| CN | 108795685 | 11/2018 |
| EP | 2956541 | 12/2018 |

(Continued)

OTHER PUBLICATIONS

International Search Report and Written Opinion in corresponding PCT/US2019/057237, dated Jan. 16, 2020.

(Continued)

*Primary Examiner* — Nianxiang Zou
(74) *Attorney, Agent, or Firm* — Hovey Williams LLP

(57) ABSTRACT

Methods for producing engineered exosomes and other vesicle-like biological targets, including allowing a target vesicle-like structure to react and bind with immunomagnetic particles; capturing the immunomagnetic particle/vesicle complex by applying a magnetic field; further engineering the captured vesicles by surface modifying with additional active moieties or internally loading with active agents; and releasing the engineered vesicle-like structures, such as by photolytically cleaving a linkage between the particle and engineered vesicle-like structures, thereby releasing intact vesicle-like structures which can act as delivery vehicles for therapeutic treatments.

23 Claims, 33 Drawing Sheets
(9 of 33 Drawing Sheet(s) Filed in Color)
Specification includes a Sequence Listing.

(56) References Cited

FOREIGN PATENT DOCUMENTS

WO 2013126774 8/2013
WO 2020086471 4/2020

OTHER PUBLICATIONS

Zhu, et al., "Microfluidic engineering of exosomes: editing cellular messages for precision therapeutics", Lab Chip, Jun. 12, 2018, 18(12), pp. 1690-1703.
Zhao, et al., "Microfluidic On-demand Engineering of Exosomes towards Cancer Immunotherapy", BioRxiv, Nov. 27, 2018, 8 pages.
Giss, et al., "Microfluidics to Isolate Untagged Proteins From Cell Extracts FOF Visual Analysis By Electron Microscopy", 17th International Conference on Miniaturized Systems for Chemistry and Life Sciences, Oct. 27-31, 2013, pp. 1785-1787.
Schmidli, et al., "Microfluidic protein isolation and sample preparation for high-resolution cryo-EM", PNAS, Jun. 17, 2019, 6 pages.
Amit, et al., "Photosensitive protecting groups of amino sugars and their use in glycoside synthesis. 2-Nitrobenzyloxycarbonylamino and 6-nitroveratryloxycarbonylamino derivatives", J. Org. Chem, 1974, 39(2), pp. 192-196 (abstract attached).
Patchornik, et al., "Photosensitive protecting groups", J. Am. Chem. Soc, 1970, 92, pp. 6333-6335 (abstract attached).
Givens, et al., "New Phototriggers 9: p-Hydroxyphenacyl as a C-Terminal Photoremovable Protecting Group for Oligopeptides", J Am. Chem. Soc, 2000, 122(12), pp. 2687-2697 (abstract attached).

\* cited by examiner

SEQUENCE LISTING

<160> NUMBER OF SEQ ID NOS: 67

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Ser Ile Ile Asn Phe Glu Lys Leu
1               5

<210> SEQ ID NO 2

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Ser Tyr Ile Gly Ser Ile Asn Asn Ile
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Lys Tyr Lys Asn Ala Val Thr Glu Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Asn Ala Ile Thr Asn Ala Lys Ile Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Glu Ala Asp Pro Thr Gly His Ser Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Glu Val Asp Pro Ile Gly His Leu Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Gly Leu Tyr Asp Gly Met Glu His Leu
1               5

<210> SEQ ID NO 8
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 8

Lys Val Ala Glu Leu Val His Phe Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Lys Val Leu Glu Tyr Val Ile Lys Val
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Phe Leu Trp Gly Pro Arg Ala Leu Val
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Lys Val Ala Glu Glu Leu Val His Phe Leu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Tyr Leu Gln Leu Val Phe Gly Ile Glu Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Gly Val Tyr Asp Gly Arg Glu His Thr Val
1               5                   10

<210> SEQ ID NO 14
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 14

Lys Val Val Glu Phe Leu Ala Met Leu
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Leu Leu Phe Gly Leu Ala Leu Ile Glu Val
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Ala Leu Lys Asp Val Glu Glu Arg Val
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Thr Phe Pro Asp Leu Glu Ser Glu Phe
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

His Asn Thr Gln Tyr Cys Asn Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Lys Leu Gln Cys Val Asp Leu His Val
1               5

<210> SEQ ID NO 20
<211> LENGTH: 11
<212> TYPE: PRT
<213> ORGANISM: Artificial Sequence
```

```
<220> FEATURE:
<223> OTHER INFORMATION: Synthetic peptide

<400> SEQUENCE: 20

Gly Val Thr Tyr Ala Cys Phe Val Ser Asn Leu
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Thr Tyr Ala Cys Phe Val Ser Asn Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

His Leu Ser Thr Ala Phe Ala Arg Val
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Ile Leu His Asn Gly Ala Tyr Ser Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Thr Tyr Leu Pro Thr Asn Ala Ser Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Ile Leu His Asp Gly Ala Tyr Ser Leu
1               5

<210> SEQ ID NO 26
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 26

Thr Tyr Val Pro Ala Asn Ala Ser Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Ile Met Asp Gln Val Pro Phe Ser Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Val Tyr Phe Phe Leu Pro Asp His Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

Lys Thr Trp Gly Gln Tyr Trp Gln Val
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic peptide

<400> SEQUENCE: 30

Val Leu Tyr Arg Tyr Gly Ser Phe Ser Val
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31

Ile Thr Asp Gln Val Pro Phe Ser Val
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 32

Tyr Leu Glu Pro Gly Pro Val Thr Val
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Tyr Leu Glu Pro Gly Pro Val Thr Ala
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Lys Val Pro Arg Asn Gln Asp Trp Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide

<400> SEQUENCE: 35

Ala Leu Leu Ala Val Gly Ala Thr Lys
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide

<400> SEQUENCE: 36

Val Tyr Phe Phe Leu Pro Asp His Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

<400> SEQUENCE: 37

Lys Ile Phe Gly Ser Leu Ala Phe Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 38

Leu Leu Gly Arg Asn Ser Phe Glu Val
1               5

<210> SEQ ID NO 39
<211> LENGTH: 11
<212> TYPE: PRT
<213> ORGANISM: Artificial Sequence
<220> FEATURE:
<223> OTHER INFORMATION: Synthetic peptide

<400> SEQUENCE: 39

Gly Leu Ala Pro Pro Gln His Leu Ile Arg Val
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Ser Leu Pro Pro Pro Gly Thr Arg Val
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Lys Leu Cys Pro Val Gln Leu Trp Val
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Arg Met Pro Glu Ala Ala Pro Pro Val
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Tyr Leu Gly Ser Tyr Gly Phe Arg Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44
```

```
Phe Leu Gly Tyr Leu Ile Leu Gly Val
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Ala Leu Phe Asp Ile Glu Ser Lys Val
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Ala Leu Gln Pro Gly Thr Ala Leu Leu
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Glu Leu Ala Gly Ile Gly Ile Leu Thr Val
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic peptide

<400> SEQUENCE: 48

Phe Leu Thr Pro Lys Lys Leu Gln Cys Val
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Leu Leu Leu Leu Thr Val Leu Thr Val
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50
```

```
Gly Leu Met Glu Glu Met Ser Ala Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Arg Leu Leu Gln Glu Thr Glu Leu Val
1               5

<210> SEQ ID NO 52
<211> LENGTH: 10
<212> TYPE: PRT
<213> ORGANISM: Artificial Sequence
<220> FEATURE:
<223> OTHER INFORMATION: Synthetic peptide

<400> SEQUENCE: 52

Leu Ile Ala His Asn Gln Val Arg Gln Val
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic peptide

<400> SEQUENCE: 53

Val Ile Ser Asn Asp Val Cys Ala Gln Val
1               5                   10

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Cys Tyr Ala Ser Gly Trp Gly Ser Ile
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55

His Cys Ile Arg Asn Lys Ser Val Ile
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic peptide

<400> SEQUENCE: 56

Lys Leu Phe Gly Thr Ser Gly Gln Lys Thr
```

<210> SEQ ID NO 57
<211> LENGTH: 10
<212> TYPE: PRT
<213> ORGANISM: Artificial Sequence
<220> FEATURE:
<223> OTHER INFORMATION: Synthetic peptide

<400> SEQUENCE: 57

Tyr Leu Asn Thr Val Gln Pro Thr Cys Val
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Val Ile Leu Thr Asn Pro Ile Ser Met
1               5

<210> SEQ ID NO 59
<211> LENGTH: 10
<212> TYPE: PRT
<213> ORGANISM: Artificial Sequence
<220> FEATURE:
<223> OTHER INFORMATION: Synthetic peptide

<400> SEQUENCE: 59

Phe Ser Asn Ser Thr Asn Asp Ile Leu Ile
1               5                   10

<210> SEQ ID NO 60
<211> LENGTH: 18
<212> TYPE: DNA
<213> ORGANISM: Artificial Sequence
<220> FEATURE:
<223> OTHER INFORMATION: Synthetic PCR Primer

<400> SEQUENCE: 60
atgcgtcttc acctggaa                                                 18

<210> SEQ ID NO 61
<211> LENGTH: 19
<212> TYPE: DNA
<213> ORGANISM: Artificial Sequence
<220> FEATURE:
<223> OTHER INFORMATION: Synthetic PCR primer

<400> SEQUENCE: 61
atcctggctc cttatctcc                                                19

<210> SEQ ID NO 62
<211> LENGTH: 14
<212> TYPE: DNA
<213> ORGANISM: Artificial Sequence
<220> FEATURE:
<223> OTHER INFORMATION: Synthetic PCR primer

<400> SEQUENCE: 62
tcatcacgca gctc                                                     14

<210> SEQ ID NO 63

```
<211> LENGTH: 14
<212> TYPE: DNA
<213> ORGANISM: Artificial Sequence
<220> FEATURE:
<223> OTHER INFORMATION: Synthetic PCR primer

<400> SEQUENCE: 63
tcatcatgca gctc                                                         14

<210> SEQ ID NO 64
<211> LENGTH: 10
<212> TYPE: DNA
<213> ORGANISM: Artificial Sequence
<220> FEATURE:
<223> OTHER INFORMATION: Synthetic PCR probe

<400> SEQUENCE: 64 cccctteegg                                                              10

<210> SEQ ID NO 65
<211> LENGTH: 10
<212> TYPE: DNA
<213> ORGANISM: Artificial Sequence
<220> FEATURE:
<223> OTHER INFORMATION: Synthetic PCR probe

<400> SEQUENCE: 65
cccctccgg                                                               10

<210> SEQ ID NO 66
<211> LENGTH: 26
<212> TYPE: RNA
<213> ORGANISM: Artificial Sequence
<220> FEATURE:
<223> OTHER INFORMATION: Synthetic miRNA adaptor sequence

<400> SEQUENCE: 66
guucagaguu cuacaguccg acgauc                                            26

<210> SEQ ID NO 67
<211> LENGTH: 19
<212> TYPE: DNA
<213> ORGANISM: Artificial Sequence
<220> FEATURE:
<223> OTHER INFORMATION: Synthetic adaptor sequence

<400> SEQUENCE: 67
aactgtaggc accatcaat                                                    19
```

METHODS FOR GENERATING THERAPEUTIC DELIVERY PLATFORMS

CROSS-REFERENCE TO RELATED APPLICATIONS

The present application is a continuation-in-part of PCT/US2019/057237, filed Oct. 21, 2019, which claims the priority benefit of U.S. Provisional Patent Application Ser. No. 62/748,470, filed Oct. 21, 2018, entitled MICROFLUIDIC ON-DEMAND CAPTURE, LOADING, AND PHOTO-RELEASE OF EXTRACELLULAR VESICLES AND EXOSOMES AS VACCINE DELIVERY PLATFORM, and the present application claims the priority benefit of U.S. Provisional Patent Application Ser. No. 63/148,781, filed Feb. 12, 2021, each of which is incorporated by reference in its entirety herein.

FEDERALLY SPONSORED RESEARCH OR DEVELOPMENT

This invention was made with government support under 2017-67021-26600 awarded by the USDA National Institute of Food and Agriculture and GM103638, GM133794, and CA221536 awarded by the National Institutes of Health. The government has certain rights in the invention.

SEQUENCE LISTING

The following application contains a sequence listing in computer readable format (CRF), submitted as a text file in ASCII format entitled "Sequence_Listing," created on Apr. 19, 2021, as 13 KB. The content of the CRF is hereby incorporated by reference.

BACKGROUND OF THE INVENTION

Field of the Invention

The disclosure generally relates to methods and materials for harvesting intact carriers or delivery vehicles for delivery of bioactive therapeutics, such as peptides or proteins, nucleotides, and other active agents (e.g., chemicals and drugs).

Description of Related Art

Among all deliverable cells and nanoparticles, live-cell derived extracellular vesicles, especially exosomes in the nano-size range of 30~150 nm, have shown important roles in intercellular communications in recent decades. The immune cell-derived exosomes have been well documented in the regulation of immune stimulation or suppression, driving inflammatory, autoimmune and infectious disease pathology. The formation of exosomes begins with the creation of endosomes as the intracellular vesicles. Exosomes are differing from other membrane-derived microvesicles by originating from multivesicular bodies (MVBs) for cellular secretion. Therefore, exosomes contain specific proteins and nucleic acids and represent their parent cell status and functions at the time of formation in parent cells. Among many subtypes of exosomes, the immunogenic exosomes with an intrinsic payload of MHC class I and II molecules and other co-stimulatory molecules are able to mediate immune responses, which opens up opportunities for the development of novel delivery platforms which can be used for cancer vaccines, immunotherapy delivery, and other delivery associated with in vivo transportation.

Compared to other nano-sized delivery systems, such as lipid, polymers, gold and silica material, exosomes are living-cell derived, highly biocompatible nano-carriers with intrinsic payload, and exhibit much stronger flexibility in loading desired antigens for effective delivery. Exosomes also eliminate allergenic responses without concerns of carrying virulent factors and avoid degradation or loss during delivery. However, the development of exosome-based vaccines is hindered by substantial technical difficulties in obtaining pure immunogenic exosomes. The diverse subtypes of exosomes could confound the investigation on differentiating different cellular messages. On the other hand, molecular engineering of exosomes through either membrane surface or internal loading could provide an untapped source for developing novel antigenic exosomes.

Bioengineered exosomes as emerging delivery vehicles have gained substantial attention in developing a new generation of cancer vaccines, including recent phase-II trial using IFN-DC-derived exosomes loaded with MHC I/II restricted cancer antigens to promote T cell and natural killer (NK) cell-based immune responses in non-small cell lung cancer patients. Unfortunately, current exosome engineering approaches, such as the transfection or extrusion of parent cells, and membrane permeabilization of secreted exosomes, suffer from poor yield, low purity, and time-consuming operations. There is a need for methods of producing exosomes to solve this bottleneck problem. Due to the intrinsic features in automation and high-efficient mass transport, microfluidic systems overcome many drawbacks of benchtop systems and show superior performance in isolating, detecting and molecular profiling of exosomes. However, molecular engineering of exosomes using microfluidic platform has not been explored. Presently, the most reported work on processing exosomes is either in small quality or bound to solid surface/particles, and they are unable to stay intact for downstream therapeutic preparations.

SUMMARY

In one aspect the present disclosure concerns methods and materials for capture and photorelease of extracellular vesicles from a biological sample. The methods and materials are suitable for use in non-invasive procedures which involve testing samples for use in monitoring the treatment of, and/or diagnosing and/or aiding in the diagnosis, of a disorder or condition that is correlated with the presence of one or more detectable markers that are contained within extracellular vesicles that may be present in the sample. In one or more embodiments, the methods and materials can be used to detect and capture subtypes of extracellular vesicles. For example, immunomagnetic particles can be designed with respective targeting moieties with specificity for a subtype of extracellular vesicle in a population of extracellular vesicles. The population of extracellular vesicles can be sequentially contacted with different mixtures of immunomagnetic particles to sequentially sort and/or capture different subtypes of extracellular vesicles. In one example, the population of initially captured extracellular vesicles can be sequentially contacted with immunomagnetic particles first comprising targeting moieties for CD36, followed by contacting with immunomagnetic particles comprising targeting moieties for CD81, followed by contacting with immunomagnetic particles comprising targeting moieties for L1CAM. At each stage, the captured extracellular vesicles can be separated from the rest of the population (e.g., using magnetic immobilization or other filtering technique). The sorted and or separated extracellular vesicle populations can then be analyzed separately.

The methods are also suitable for engineering the extracellular vesicles themselves by attaching one or more moieties thereto for subsequent in vivo administration as a carrier for delivering a therapeutic or active agent. In embodiments, any biological sample can be used, and can be tested directly, or can be subjected to a processing step before being tested.

In general, the methods comprise contacting a test sample with a plurality of immunomagnetic particles. In one or more embodiments, the sample is a fluid contained within a test container. In one or more embodiments, the sample may be a solid, which is first dispersed in a suitable buffer system, which is then contained within a test container. Samples may be subjected to pre-processing to either concentrate the sample and/or dilute the sample as desired. In one or more embodiments, the plurality of immunomagnetic particles are added to the test container before, after, or simultaneously with the sample. In one or more embodiments, the sample and immunomagnetic particles are intermixed, such as via gentle agitation, vibration, shaking, stirring, and the like, to yield a test mixture. In one or more embodiments, the magnetic aspect of the immunomagnetic particles can itself be used to facilitate mixing of the sample with the particles (e.g., by using an external magnetic to swirl the particles throughout the sample). In one or more embodiments, the test sample and immunomagnetic particles are allowed to mix for a sufficient period of time to ensure complete mixing and reaction with target extracellular vesicles which may be present in the sample. In one or more embodiments, the sample and particles are allowed to mix for at least 30 minutes. In one or more embodiments, the sample and particles are allowed to mix for at least an hour, at least two hours, at least 3 hours, at least 4 hours, at least 5 hours, at least 6 hours, at least 7 hours, at least 8 hours, at least 9 hours, at least 10 hours, at least 11 hours, at least 12 hours (e.g., overnight). In one or more embodiments, the test sample and immunomagnetic particles are mixed at room temperature or below, preferably at decreased temperature (~4 □C) conditions. It will be appreciated that the particular incubation conditions and times may depend on and can be optimized depending upon the selected targeting moiety used and its target ligand on the target extracellular vesicles (i.e., the affinity pairs). For example, longer times and/or reduced temperatures can facilitate binding between certain affinity pairs, whereas faster times and/or increased temperatures can facilitate binding between other affinity pairs.

Once the sample and immunomagnetic particles have sufficiently mixed, and target extracellular vesicles which may be present in the sample have had adequate opportunity to react with the immunomagnetic particles, an external magnet is applied to the outside of the test container, preferably at a single location (e.g., along an edge sidewall or bottom) to magnetically direct, collect, and immobilize the immunomagnetic particles in the test mixture at a single location. In one or more embodiments, the test container is positioned in a holder configured to present a magnet below the test container, thereby pulling the immunomagnetic particles down to the bottom of the container as a concentrated pellet. The text mixture is then washed 1-3 times using a suitable buffer. Advantageously, using magnetic immobilization means that the immunomagnetic particles and bound extracellular vesicles (if any) will remain immobilized at the location in the test container during the washing.

The washed particles and bound extracellular vesicles (if any) are then resuspended in buffer to create a photorelease mixture. In one or more embodiments, the photorelease mixture may be transferred to a new container or the photorelease step may be carried out in test container ("photorelease container"). In one or more embodiments, the new container is preferably a clear container, more preferably, a glass container to facilitate transmission of irradiation through the container and into the mixture for the photorelease step. In one or more embodiments, the photorelease mixture is exposed to activating radiation of the appropriate wavelength depending upon the photocleavable linker used in the immunomagnetic particles. Exposure times and total exposure dosages can vary depending upon the source of radiation and the photocleavable linkers.

After photorelease, an external magnet is applied to the outside of the photorelease container, preferably at a single location (e.g., along an edge sidewall or bottom) to magnetically direct, collect, and immobilize the immunomagnetic particles in the photorelease mixture at a single location. In one or more embodiments, the photorelease container is positioned in a holder configured to present a magnet below the photorelease container, thereby pulling the immunomagnetic particles down to the bottom of the container as a concentrated pellet. This concentrated pellet contains the released immunomagnetic particles, whereas the previously-captured extracellular vesicles have been cleaved from the particles remain suspended in the supernatant. The previously-captured extracellular vesicles can then be collected and analyzed. In one or more embodiments, the supernatant containing the previously-captured extracellular vesicles is poured or pipetted out of the container. The previously-captured extracellular vesicles can then be isolated for analysis (e.g., using one or more rounds of centrifugation, and the like). An overview of the process is depicted in the Figures. Suitable containers include any vessel configured to hold a liquid, including, without limitation, microfluidics chambers, test tubes, centrifuge tubes, microtubes, beakers, vials, flasks, bottles, and other glassware, ELISA well plate, microtiter plates, 6-well, 12-well, 24-well, 48-well, 96-well, or 384-well plates, cell culture containers (petri dishes, bioreactors, 3D culture containers), and other fluid holding containers.

Various immunomagnetic particles with photocleavable linkers can be used in the foregoing process, including those described in co-pending PCT/US2019/057237, filed Oct. 21, 2019, and incorporated by reference in its entirety herein. Particularly preferred particles for use in these systems are graphene oxide-based magnetic particles, such as described in U.S. Pat. No. 10,788,486, filed Oct. 9, 2017, and incorporated by reference in its entirety herein.

Advantageously, this targeted approach, particularly when using graphene oxide-based immunomagnetic particles, results in highly purified populations of intact extracellular vesicles or exosomes. It will be appreciated that such pure populations enable more sensitive and/or more specific detection of target biomarkers, with less background noise for more accurate diagnostics. Such extracellular vesicles, once isolated, can be mined for various diagnostic values, including nucleic acid-based biomarkers for various diseases, proteomics, or multi-omics. The drug loading and engineering of extracellular vesicles also can be implemented in the protocols for developing therapeutics and drug delivery. The reproducible isolation of specific intact sEV subpopulations are essential to support well-controlled and precision drug delivery in vivo. The prepared target extracellular vesicles can also be released from the targeting moieties, leaving behind intact target extracellular vesicles with potential benefits.

Microfluidic methods and devices are also described herein as one exemplary, but not limiting, way to capture and/or engineer a variety of biologic carriers or delivery vehicles, such as cells, extracellular vesicles and exosomes, and membrane or lipid particles, and polymer particles. It will be appreciated that the methods can involve microfluidics for all or only a portion of the capture, release, and/or analysis processes. Likewise, as exemplified below, the processes and materials are not limited to microfluidics applications.

Regardless of the embodiment, these carriers can be captured using the inventive methods and devices, loaded with active agents (either surface modified or encapsulated), and then released as intact, engineered carriers for delivering a variety of therapeutic compounds and bioactive agents. The engineered carriers can be used for diagnostics, prognostics, companion assays, pharmaceutics and therapeutics, immunotherapy and vaccine delivery, and tissue delivery, and other usage associated with in vivo transportation of active agents. Embodiments described herein are exemplified with respect to exosomes. However, it will be appreciated that exosomes represent a particularly challenging biological target, such that it is envisioned that the platform can be applied to other similar structures—vesicular or vesicle-like structures characterized by a liquid core and membrane or bilayer—including cells (including T-cells), microsomes, and the like. These biological targets, which are then engineered into carriers or delivery vehicles can also be characterized as nanocarriers.

In one exemplary aspect, the present disclosure concerns microfluidic analytical devices and method of on-demand capture, loading, and photo-release of intact engineered nanocarriers. The microfluidic devices can enable real-time harvesting and antigenic modification of extracellular vesicles, particularly exosomes, with subsequent release of intact exosomes downstream on-demand.

Also disclosed for use in any of the described embodiments are magnetic-nanoparticles functionalized with photo-cleavable, affinity probes (active moieties) for capturing and on-demand releasing MHC-I positive exosomes via a light trigger. The affinity probe can include an antigenic peptide, antibody, aptamer, nanobody and other affinity-based probes. The photo-release of the modified/loaded exosomes in the microfluidic devices or other suitable vessel can be well controlled spatially and temporally with 95% or greater efficiency. Such a culture system allows antigenic engineering of exosomes either through mediating their parent cell growth using stimulations, or direct molecular engineering on the surface of produced exosomes. Heterogeneity of exosome subtypes has been found from the same population of parent cells. The released subtypes of exosomes contain distinct molecular and biological properties for different cellular regulation. The disclosed methods can capture, load, and release specific subtype of exosomes with more targeted therapeutic functions. The carriers that can be used in this disclosed method for capture, loading and release include cells, extracellular vesicles and exosomes, and membrane or lipid particles, and polymer particles, which can encapsulate drugs (small molecule compounds), genes and bioactive therapeutics. Proof of concept with several tumor antigenic peptides (e.g., gp-100, MAGE-A3, and MART-1) which are commonly used in developing cancer vaccines but difficult in delivery due to the degradation have been demonstrated herein. The microfluidic devices are used by way of example to show high-efficiency in engineering immunogenic exosomes (MHC I+), meanwhile, photo-releasing the intact functional exosomes downstream. Cellular uptake of engineered exosomes by antigen presentation cells has also been demonstrated, which displayed much-improved internalization ability compared to non-engineered exosomes. In particular, the engineered exosomes show significantly higher activation rate (at least 30%) for activating T cells by challenging CD8 T cells purified from the spleen of 2 Pmel1 transgenic mice, than non-engineered exosomes. We also assessed the degree of potency of antimicrobial peptide-engineered immunogenic exosomes for stimulating T cells ex vivo using transgenic mice for treating bovine respiratory syncytial virus (BRSV) infections. Exosomes engineered with BRSV targeting peptide (Peptide 4: M187-195 peptide NAITNAKII, SEQ ID NO:4) have the capacity to activate BRSV M-specific T cells in the presence of activated dendritic cells.

An important aspect of the methods and materials is that they are able to capture and release for analysis or use intact extracellular vesicles, meaning that their membranes remain intact and unbroken or undamaged (i.e., the vesicle has not ruptured) and have no relevant component removed or destroyed by the capture and release process. Accordingly, the engineered extracellular vesicles are viable and functional for application in cancer immunotherapy and vaccination for infectious disease, among other uses. This approach for producing engineered vesicles not only provides an enabling strategy for high-efficiency production of purified, enriched therapeutic vesicles but also serve as an investigation tool for understanding roles of variable peptide-engineered exosomes in antitumor immune responses, cancer immunotherapy, and vaccination for treating infections.

In specific aspects, the microfluidic devices disclosed herein can comprise a cell culture chamber dimensioned to maintain biological material in a three-dimensional configuration; a mixing channel fluidly connected to the cell culture chamber and comprising a plurality of sample inlet channels disposed along the mixing channel, wherein the ratio of a width of the cell culture chamber to the largest cross-sectional dimension of the mixing channel is at least 5:1; an isolation channel defining a path for fluid flow from the mixing channel to an isolation outlet; and a collection chamber fluidly connected to the isolation outlet and comprises a magnet operatively coupled to the collection chamber to produce a magnetic field within the collection chamber.

In other aspects, the microfluidic devices can comprise a cell culture chamber comprising a cell culture inlet and a cell culture outlet; a fluid inlet channel and a particle inlet channel, wherein the cell culture outlet, the fluid inlet channel, and the particle inlet channel fluidly converge at a mixing intersection; a mixing channel fluidly connected to the mixing intersection and defining a path for fluid flow from the mixing intersection to a mixing outlet, wherein the ratio of a width of the cell culture chamber to the largest cross-sectional dimension of the mixing channel is at least 5:1; and a collection chamber fluidly connected to the mixing outlet and comprises a magnet operatively coupled to the collection chamber to produce a magnetic field within the collection chamber. In these aspects, the mixing channel can comprise an isolation channel disposed between the mixing intersection and the mixing outlet.

The isolation channel in the microfluidic devices can have a geometry to induces turbulent flow so as to mix flowing fluids in the device. For example, the isolation channel in the microfluidic devices can have a serpentine geometry. The isolation channel can further include one or more channel constriction domain that decreases in width for producing a local vortex flow profile. In certain embodiments, the isolation channel can comprise a plurality of channel constriction domains, preferably at least 5 channel constriction domains.

As described herein, the microfluidic devices comprise a cell chamber and a mixing channel. The cell chamber and the mixing channel can have a height and a width. The height and the width of the mixing channel can each be at least 50 microns, preferably between 50 and 500 microns. The ratio of the cell culture chamber width to the largest cross-sectional dimension of the mixing channel can be from 5:1 to 500:1, from 5:1 to 200:1, from 5:1 to 100:1, from 5:1 to 20:1, preferably from 6:1 to 12:1. The cell culture chamber can have a volume of about 200 microliters or greater, preferably from about 200 microliters to about 1 milliliter.

The microfluidic devices disclosed herein can further comprise a pump operably coupled to the device.

It also disclosed the method of using the device for capture of a target in a sample solution, loading, and on-demand photo release can be used for harvesting intact delivery carriers. Such carriers can be cells, extracellular vesicles and exosomes, and membrane or lipid particles, and polymer particles, which can encapsulate drugs, genes and bioactive therapeutics. Specifically, this integrated and continuous method of capture, loading and photo-release can produce the engineered exosomes in a microfluidic device. The methods comprise introducing a biological sample containing exosomes (or another target) into a mixing channel and mixing the exosomes with immunomagnetic particles and a wash buffer to form a mixture; allowing the exosomes to react and affinity bind with the immunomagnetic particles; and collecting the exosomes bound to the immunomagnetic particles by applying a magnetic field within a collection chamber. The method for producing the engineered exosomes can include introducing cells into a cell culture chamber of the microfluidic device and first culturing the cells under conditions allowing the release of exosomes. This can be carried out in-line, in the same microfluidic device used for capture and loading.

The cells from which the exosomes are released can be selected from dendritic cells, stem cells, immune cells, megakaryocyte progenitor cells, macrophages, or other live cells.

The immunomagnetic particles bound to the exosomes can comprise a magnetic particle-bound to an affinity probe for capturing exosomes via a moiety comprising a photocleavable linker. As described herein, the affinity probe for capturing exosomes can include an antigen peptide, antibody, aptamer, or antigenic epitope thereof for capturing the exosomes. Suitable examples of antigen peptides include MAGE-A3, gp-100, HER-2, p53, PSA-1, or MART-1. The moiety comprising the photocleavable linker can include biotin bound to immunomagnetic particle and attached at the other end via a photocleavable linker to the affinity probe. The affinity probe targets surface proteins on the target (e.g., immunostimulatory molecules or markers). Suitable immunostimulatory molecules include an MHC class I molecule, an MHC class II molecule, an interleukin, TNFα, IFNγ, RANTES, G-CSF, M-CSF, IFNα, CTAPIII, ENA-78, GRO, I-309, PF-4, IP-10, LD-78, MGSA, MIP-1α, MIP-1β and combinations thereof. Preferably, the affinity probe is itself an antigenic moiety (peptide) which preferentially binds to a surface protein on the target.

After mixing, the immunomagnetic particles capture/bind exosomes (or other target) in the sample. The immunomagnetic particles are immobilized in the device, e.g., using a magnet positioned adjacent to a collection chamber. The immobilized bead/exosome complexes are then washed and incubated with buffer solution containing active moieties for either surface loading onto the captured exosomes or internal encapsulation, as described in more detail below. The methods can further comprise photolytically cleaving the captured, modified exosomes from the immunomagnetic particles, releasing intact, engineered exosomes comprising the active agent (antigen peptide or antigenic epitope thereof).

The methods for producing the engineered biological targets, such as exosomes, can be performed using the microfluidic devices disclosed herein, although the process is not limited to microfluidics and can be carried out in any suitable vessel or series of vessels. In some embodiments, the methods are carried out in real-time. In one or more embodiments, the methods are streamlined (aka "continuous"), such that the capture, loading, and release of the biological target occurs in the same device/container (i.e., without having to transfer or move between containers or reaction tubes, but rather in-line along a microfluidic channel and in-line capture/engineering chamber). Thus, each of the steps can be carried out consecutively, one after the other using the various inlets which converge at a single microfluidic channel, and preferably substantially immediately one after the other. In other words, the method involves immunomagnetic bead loading, followed immediately or nearly simultaneously with sample loading, followed by loading of the active agents to be attached to or loaded into the captured target. Each component loaded into the microfluidic device converges from respective inlets into a single microfluidic channel, followed by "automatic" retention in the capture/engineering chamber downstream from the inlet by the magnet positioned adjacent to the chamber. As the fluid mixture flows through the channel and then the chamber, the respective reactions are occurring in real-time (i.e., capture and loading). Application of light to the chamber can then release the engineered target. It will be appreciated that the streamlined process is much faster than traditional benchtop methods. Preferably, the process from sample/bead loading at respective inlets to collection of the released at the outlet, engineered target can be completed within approximately 2 hours total, more preferably within approximately 90 minutes, and more preferably within approximately 1 hour.

Compositions comprising engineered exosomes, particularly immunogenic exosome complexes are also disclosed. The immunogenic exosome complex can comprise an antigenic peptide or antigenic epitope thereof conjugated to a surface of an exosome, wherein the immunogenic exosome complex activates T-cell by at least 30% compared to a native exosome. The antigenic loading of such antigenic peptide or antigenic epitopes can be performed after mixing and capture exosomes for completely coating exosome surface with antigenic peptides. The compositions can be prepared using the methods disclosed herein. Accordingly, immunogenic exosome complex prepared by a process comprising introducing cells into a cell culture chamber of a microfluidic device; culturing the cells under conditions allowing release of engineered exosomes; introducing the engineered exosomes into a mixing channel and mixing the engineered exosomes with immunomagnetic particles and a wash buffer to form a mixture for exosome capture/binding; then apply a magnetic field within a collection chamber to collect the isolated exosomes, allowing to react with the loading buffer containing antigenic peptides to form an immunogenic exosome complex; and apply UV light to break the photo-cleavable linker for collecting the immunogenic exosome complex at the outlet of microfluidic device.

Pharmaceutical compositions comprising the immunogenic exosome complex are also disclosed. The loading targets can be drugs, genes and bioactive therapeutics. Methods of treating disease in a subject comprising administering to the subject a pharmaceutical composition comprising an immunogenic exosome complex are disclosed. In certain embodiments, the disease can be an infection. In some examples, the disease can be cancer. When the disease to be treated is cancer, the methods can further include administering a chemotherapeutic agent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 25C shows Gene Ontology enrichment analysis of differently expressed proteins from NanoPoms prepared BC urinary sEVs. Most abundant items are listed in biological process, cell component and molecular function, respectively.

DETAILED DESCRIPTION

Figure 1:
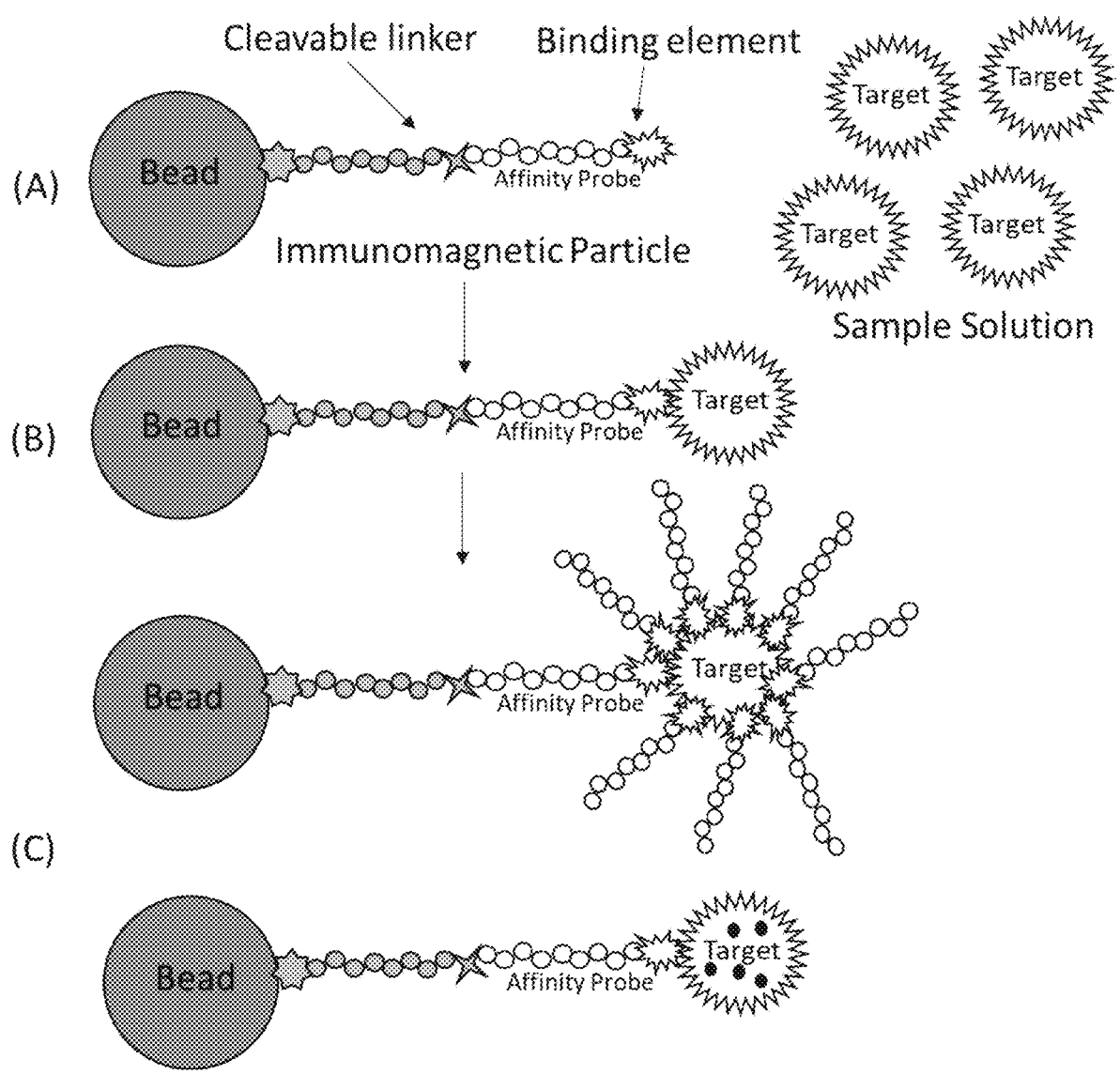
FIG. 1 illustrates (A) immunomagnetic beads mixed with a sample solution, (B) capture of targets in a sample solution using immunomagnetic beads; and (C) loading of antigenic or active agents onto or inside of the captured target.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular fluidic channel is disclosed and discussed and a number of modifications that can be made to the fluidic channels are discussed, specifically contemplated is each and every combination and permutation of the fluidic channels and the modifications that are possible unless specifically indicated to the contrary. Thus, if a class of fluidic channels A, B, and C are disclosed as well as a class of fluidic channels D, E, and F and an example of a combination fluidic channels, or, for example, a combination fluidic channels comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the devices disclosed herein have certain functions. Disclosed are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Thus, where a method claim does not expressly recite an order of steps to be followed or it is not otherwise specifically stated in the claims or description that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "can," "may," "optionally," "can optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

Ranges can be expressed as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It is also understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "upstream" and "downstream" refer to positions within a device which are relative another position and a direction of fluid flow. As used herein, the term "upstream" refers to a first position that is located in a direction opposite the direction of fluid flow relative to a second position. Conversely, as used herein, the term "downstream" refers to a second position that is located in a direction along the direction of fluid flow relative to a first position.

Methods

With reference to FIG. 1, the general methods described herein involve a plurality of immunomagnetic particles (beads), which are mixed with a sample solution suspected of containing a target population of extracellular vesicles. In some embodiments, a biological sample is collected from a subject and prepared for the method, e.g., by diluting with buffer, concentrating, etc. In some embodiments, cells are collected and expanded in culture. In some embodiments, cells are collected and cultured under conditions to release exosomes or other extracellular vesicles or vesicle-like structures into culture. In any event, the immunomagnetic particles contain a photocleavable linker and affinity probe (and preferably a plurality of photocleavable linkers, each with a respective affinity probe) extending from the particle surface for capturing the target. The immunomagnetic particles are contacted with a sample solution for a period of time sufficient for the target (if present in the sample) to interact with the affinity probes extending from the immunomagnetic particles. In FIG. 1, a single bead is depicted with a single linker for ease of illustration; however, in practice, each immunomagnetic particle will be coated with a plurality of linkers (preferably substantially the entire surface area of the particle/bead is coated with linkers). Moreover, the relative sizes in FIG. 1 are not to scale, but enlarged for illustration purposes. In practice, the bead/particle is preferably at least 5 times larger than the target (e.g., in the case of exosomes, which range 30-150 nm in diameter, the bead is preferably 500 nm or larger, preferably from about 500 nm to about 1000 nm or from about 500 nm to about 800 nm, but beads as small as 5 nm to about 100 nm can be used in some embodiments). In this way, a plurality of targets (e.g., extracellular vesicles) will be captured on the surface of a single bead/particle. FIG. 1 uses a single bead and target interaction for ease of reference. As shown in FIG. 1(A), the bead and sample solution are mixed for a sufficient period of time (e.g., in a mixing chamber or channel in the microfluidic device). If the target is present in the sample solution, it will be captured by the bead (and specifically by an affinity probe extending from the bead via its photocleavable linker), as illustrated in FIG. 1(B). Exemplary photocleavable linkers are described herein, and may include linear chains including biotin or similar moiety at one end for attachment to the particle and an amine moiety at the other end for attachment to the affinity probe. A preferred linker has the following structure, where the dashed line indicates the bond cleaved during photo exposure, and the "binding group" represents the moiety (e.g., biotin) used to attach the linker to the bead (directly or via a functionalized surface coating, e.g., avidin):

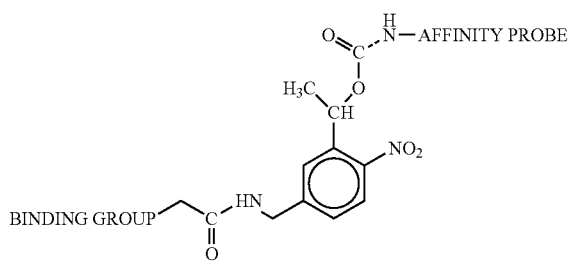

Although various embodiments are described herein, the affinity "probe" is typically an oligopeptide sequence that has specificity for and recognizes the target, such as a peptide that recognizes and acts as a receptor for a surface protein on the target. As used here, the phrase "specificity for" is intended to differentiate the affinity probe from non-specific binding or reactions between molecules, and means that the set of specific targets for which the affinity probe can interact is limited, and in some cases even exclusive, such that binding does not occurs at an appreciable rate with any other molecule except for the target (and specifically, its designated surface protein(s)). Short oligopeptide sequences are preferably used for the affinity probe including sequence segments with high specificity for the target. More preferably, upon binding, the affinity probe and surface protein create a complex that enhances the immunogenic potential of the target, as described in more detail herein and demonstrated in the working examples.

The bead with the captured target (e.g., extracellular vesicles) is immobilized in the vessel at a first location. The bead can be immobilized before or after capture of the target. As described elsewhere herein, this can be achieved by positioning a magnet adjacent a collection or engineering chamber in the microfluidic device or other vessel. As the sample solution and bead solution flow through the microfluidic channel or are mixed within the vessel, the beads and target interact and come into proximity or contact with one another thereby capturing the target. The magnetic beads are immobilized in the collection or engineering chamber or first location in the vessel (thereby also immobilizing the captured target) as the solutions flow through or mixes around. As illustrated in FIG. 1(C), the captured target is then engineered either by attaching a plurality of active agents (e.g., antigenic peptides) to the target surface or loading the target with drugs, chemicals, nucleotides, or other bioactive agents (e.g., CRISPR Cas9). For surface modification, the immobilized bead/target complex is washed and incubated in the vessel with buffer solution containing a plurality of active agents having at least one moiety that has specificity for a surface protein presented on the surface of the target. Preferably, the active agents or moieties for surface loading are of the same "type" of compound (e.g., comprise the same oligopeptide) selected for the affinity probe used in the immunomagnetic particles. The immobilized bead/target complex is incubated with the active agents for a period of time sufficient for the active agents to interact with the captured target. Preferably, the active agent loading into the vessel is at a concentration such that substantially the entire surface of the target is coated with active agents (e.g., preferably, substantially all of the target surface protein is bound by active agent).

Instead of surface modification, FIG. 1(C) also depicts an alternative where active agents can be loaded into the target. This can be carried out by washing and incubating the immobilized bead/target complex in the microfluidic device with buffer solution containing active agents to be loaded, along with detergents or chemical transfection reagents to induce pore formation in the target for active agent loading, followed by washing with buffer to remove the reagents and close the pores. Other approaches for membrane permeabilization can be used, including irradiation, electroporation, ultrasound, sonication, microinjection biolistic particle delivery, and the like, which induce pore formation in the extracellular vesicle membrane other otherwise allow the active agent to be loaded or introduced into the vesicle. Various active agents can be loaded including proteins, peptides, nucleic acids (DNA, RNA, oligonucleotides), small molecule drugs, nanoparticles, biologics, and the like.

In either embodiment, excess active agent is then washed away leaving engineered target immobilized with the immunomagnetic bead.

Figure 2A:
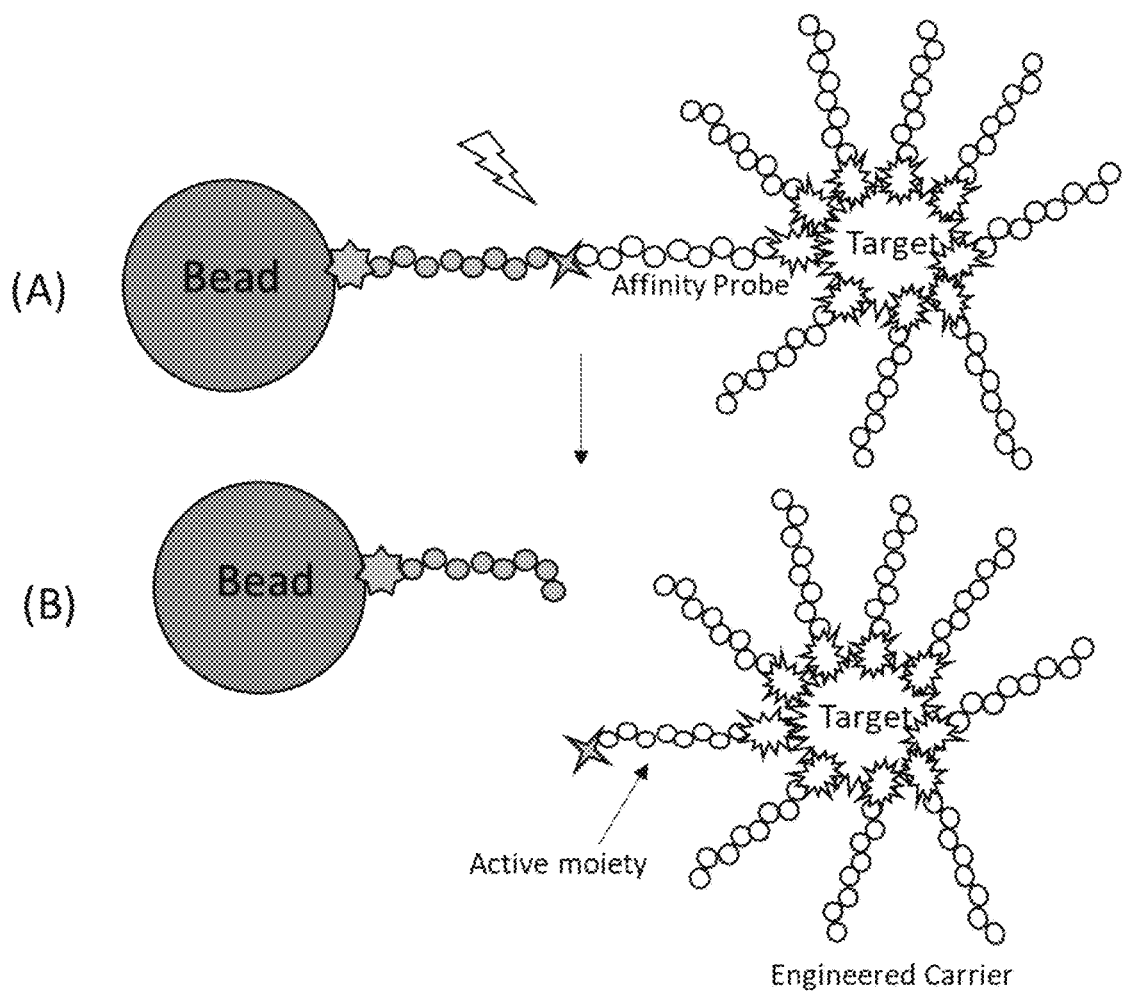
FIG. 2A illustrates (A) application of light or activating radiation to the bead/target complex, and (B) photorelease of an engineered target (carried) surface modified with active agents or antigenic moieties.
Figure 2B:
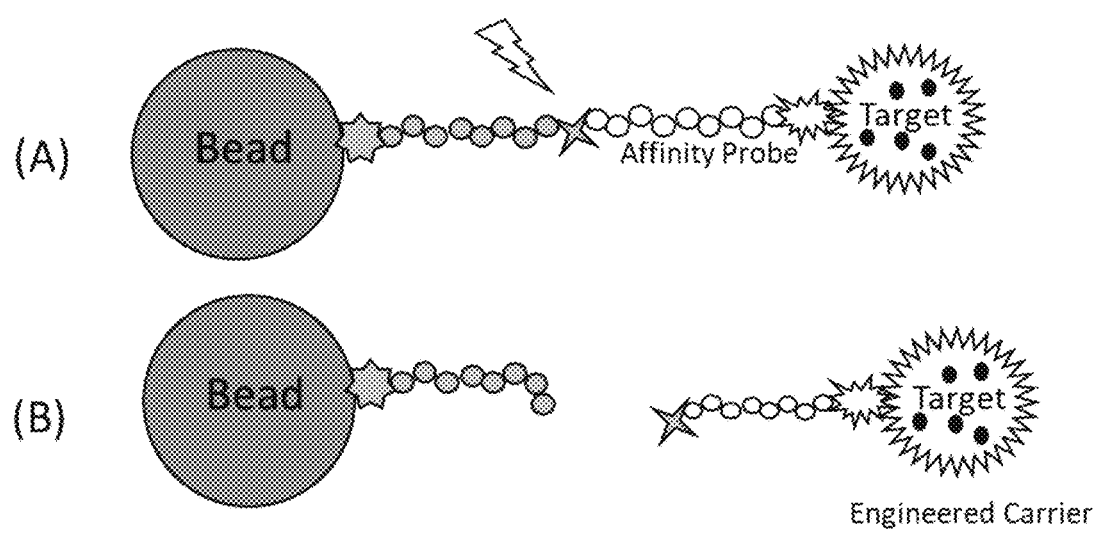
FIG. 2B illustrates (A) application of light or activating radiation to the bead/target complex, and (B) photorelease of an engineered target (carrier) loaded with active agents inside.

With reference to FIG. 2A, the engineered target can then be released by exposing the immobilized bead/target complex to activating radiation (e.g., light) of the appropriate wavelength to cleave the photocleavable linker. This process releases the engineered target along with the affinity probe which remains bound to the target, which now acts as an engineered carrier or delivery vehicle for the active agents decorated on the surface of the target. Likewise, in FIG. 2B, the same photorelease process can be used to release the targets internally loaded with active agents. A wash buffer can be introduced into the vessel or into the microfluidic device to transport the released targets downstream for collection at the outlet of the microfluidic device. Advantageously, the light release step in embodiments of the invention is carried out with exposure times of 15 minutes or less, preferably about 13 minutes or less, more preferably about 12 minutes or less. As demonstrated in the working examples, approximately 100% of the captured target is preferably released/cleaved within about 10 minutes of exposure time.

It will be appreciated that since the magnetic beads are already immobilized in the engineering chamber or vessel, a separate step is not required to separate the target from the magnetic beads in the solution. Rather, upon exposure, the linker between the captured target and the bead is cleaved, thereby releasing the engineered targets, which flow downstream away from the immobilized beads to the outlet of the microfluidic device, or can be poured or pipetted away from the immobilized beads. The released targets, which have been engineered with the active moieties (aka the "engineered carrier"), can then be collected for analysis and therapeutic use from the outlet of the microfluidic device or otherwise directly diverted to a further chamber or collection vessel. It will be appreciated that the immunomagnetic beads can then be subsequently collected for re-use by removing the magnetic field from the microfluidic device, such that the immunomagnetic beads are no longer magnetically immobilized. The beads can be washed downstream and collected from the outlet.

In some embodiments, the released targets, which have been engineered with the attached targeting moieties can be further processed to release the targeting moieties from the extracellular vesicle surface. This can be accomplished without damaging the captured extracellular vesicles, such as by using conventional Western blot stripping and washing buffers to release the affinity probe, and incubating the captured extracellular vesicles with the appropriate stripping buffer, followed by washing to separate the stripped (bare) extracellular vesicles and the formerly-attached targeting moieties.

As noted, this process can advantageously take place in any suitable vessel, including in a microfluidic device, and as a continuous, integrated, in-line approach for isolating, capturing, engineering, and releasing intact targets, such as exosomes from a sample, as therapeutic carriers or delivery vehicles.

Devices

Extracellular vesicles (≤1 μm), particularly exosomes (30-150 nm), are the emerging cargo for mediating cellular signal transductions. However, standard benchtop methods (e.g., ultracentrifugation and filtration) lack the ability to process immunogenic exosomes specifically among other microvesicle subtypes, due to time-consuming (>10 h) and extremely tedious isolation protocols. In one aspect, the present disclosure addresses needs in the art by providing a protocol that can be carried out using conventional liquid handling vessels and utilizing innovating magnetic immobilization and photorelease to streamline the process.

Figure 3:
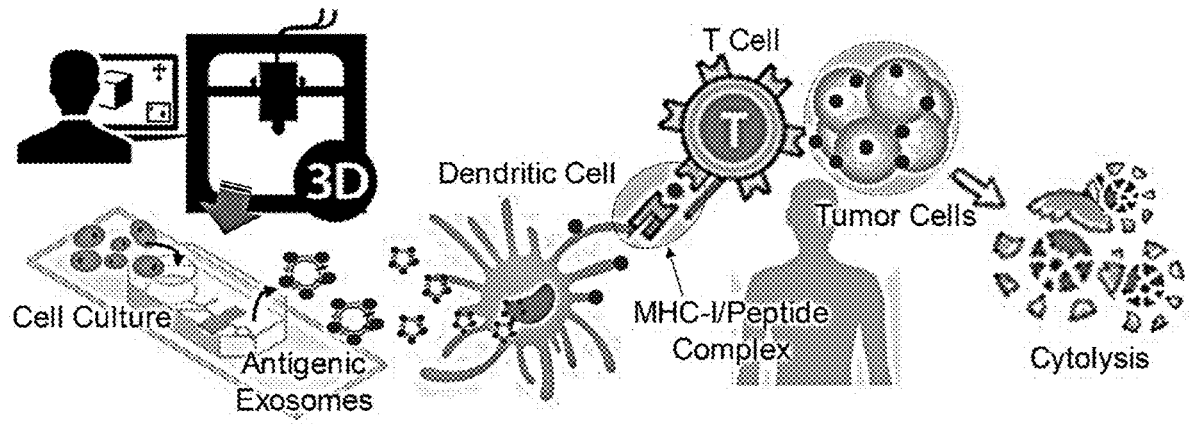
FIG. 3 is an illustration of a process overview for a 3D-printed molded PDMS microfluidic culture chip for streamlined engineering of antigenic exosomes employed in activating anti-tumor responses.

In a further aspect, the present disclosure addresses needs in the art by providing devices that introduce a streamlined microfluidic platform for harvesting, antigenic modification and photo-release of immunogenic extracellular vesicles and exosomes directly from on-chip cultured cellular media. These devices provide automatic and rapid cell-culture production of antigenic exosomes that can be used in immunotherapy such as cancer immunotherapy. In one aspect, the devices disclosed herein enables real-time harvesting and antigenic modification of exosomes with subsequent photo-release downstream on-demand, as depicted in the overview in FIG. 3.

Figure 4:
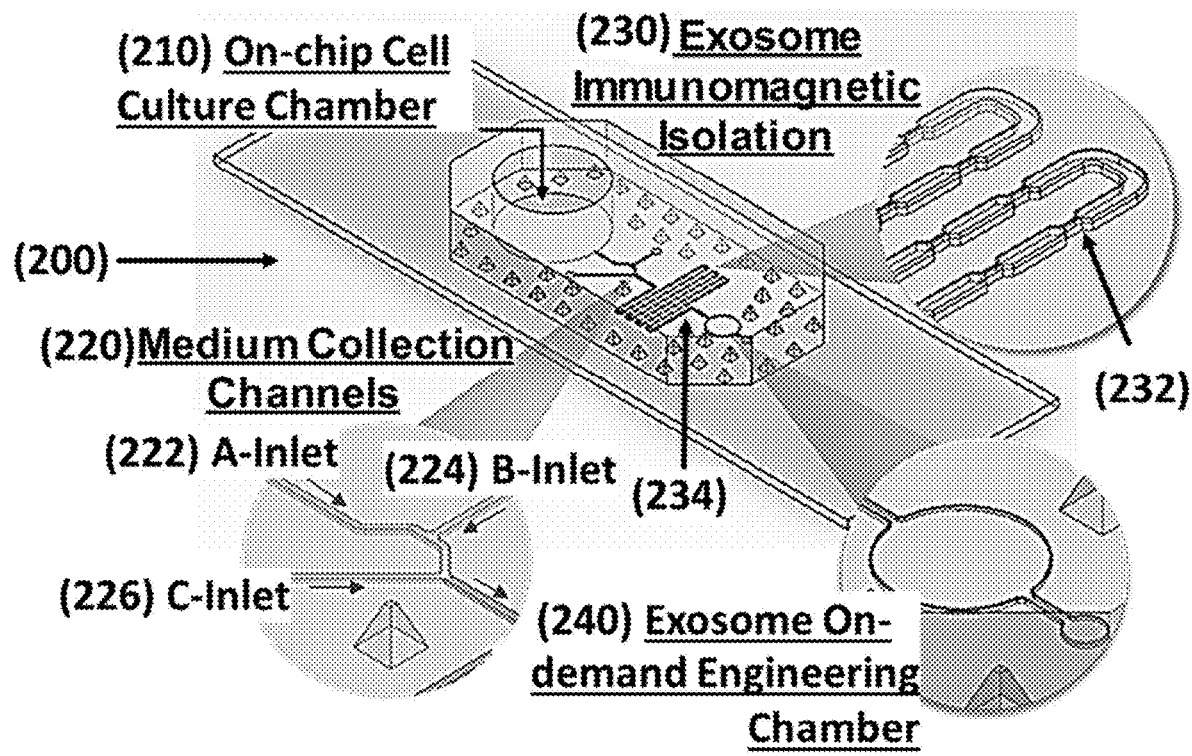
FIG. 4 illustrates an embodiment of a microfluidic device.

Turning now to FIG. 4, disclosed herein is a microfluidic device (200) comprising a cell culture chamber (210) dimensioned to maintain biological material in a three-dimensional configuration; a mixing channel (220) fluidly connected to the cell culture chamber and comprising a plurality of sample inlet channels (222, 224, 226) disposed along the mixing channel, wherein the ratio of a width of the cell culture chamber (210) to the largest cross-sectional dimension of the mixing channel (220) is at least 5:1; an isolation channel (230) defining a path for fluid flow from the mixing channel (220) to an isolation outlet (234); and a collection chamber (240) fluidly connected to the isolation outlet (234) and comprises a magnet operatively coupled to the collection chamber to produce a magnetic field within the collection chamber (240).

Devices of the present disclosure can be described by sizes and comparisons of sizes (e.g., ratios) of components within the device. In some embodiments, the cell culture chamber (210) has a volume of about 200 microliters or greater (for example, 200 microliters or greater, 250 microliters or greater, 300 microliters or greater, 350 microliters or greater, 400 microliters or greater, 450 microliters or greater, 500 microliters or greater, 550 microliters or greater, 600 microliters or greater, 650 microliters or greater, 700 microliters or greater, 750 microliters or greater, 800 microliters or greater, 850 microliters or greater, 900 microliters or greater, 950 microliters or greater, or 1 milliliter or greater). In some embodiments, the cell culture chamber (210) has a volume of about 1000 microliters or less (for example, 950 microliters or less, 900 microliters or less, 850 microliters or less, 800 microliters or less, 750 microliters or less, 700 microliters or less, 650 microliters or less, 600 microliters or less, 650 microliters or less, 550 microliters or less, 500 microliters or less, 450 microliters or less, 400 microliters or less, 350 microliters or less, 300 microliters or less, 250 microliters or less, or 200 microliters or less). In some embodiments, the cell culture chamber (210) has a volume of from about 200 microliters to about 1 milliliter (for example, from 200 microliters to 900 microliters, from 200 microliters to 750 microliters, from 200 microliters to 500 microliters, from 300 microliters to 750 microliters, or from 350 microliters to about 500 microliters). In some embodiments, the cell culture chamber has a sufficient volume such that the top can be left open for applying a plug (such as a PDMS-made, finger-push plug) for fluid exchange and pushing the fluid to downstream collection channels.

In some embodiments, the cell culture chamber has a height and a width. The cell culture chamber can have a height of at least 500 microns (for example, 500 microns or greater, 600 microns or greater, 650 microns or greater, 700 microns or greater, 750 microns or greater, 800 microns or greater, 850 microns or greater, 900 microns or greater, 950 microns or greater, or 1000 microns of greater). In some embodiments, the cell culture chamber has a height of 1000 microns or less (for example, 950 microns or less, 900 microns or less, 850 microns or less, 800 microns or less, 750 microns or less, 700 microns or less, 650 microns or less, 600 microns or less, or 500 microns or less). In some embodiments, the cell culture chamber has a height of from 500 microns to 1000 microns (for example, from 600 microns to 1000 microns, from 750 microns to 1000 microns, or from 800 microns to 1000 microns).

The cell culture chamber can have a width of at least 200 microns (for example, 250 microns or greater, 275 microns or greater, 300 microns or greater, 350 microns or greater, 400 microns or greater, 450 microns or greater, 500 microns or greater, 550 microns or greater, or 600 microns or greater). In some embodiments, the cell culture chamber has a width of 1000 microns or less (for example, less than 1000 microns, 750 microns or less, less than 750 microns, 600 microns or less, 550 microns or less, or 500 microns or less). In some embodiments, the cell culture chamber has a width of from 250 microns to 1000 microns (for example, from 250 microns to 750 microns, from 250 microns to 500 microns, from 300 microns to 750 microns, or from 300 microns to 500 microns).

As described herein, the mixing channel (220) fluidly connects to the cell culture chamber and comprises a plurality of sample inlet channels (222, 224, 226) disposed along the mixing channel. The plurality of sample inlet channels can include a cell culture inlet channel (also referred to herein as B-inlet, 222) that fluidly connects to the cell culture chamber and defines a path for introducing fluid from the cell culture chamber into the mixing channel. The plurality of sample inlet channels can further include a particle inlet channel (also referred to herein as A-inlet, 224) that defines a path for introducing particles into the mixing channel. The plurality of sample inlet channels can further include a fluid inlet channel (also referred to herein as C-inlet, 226) that defines a path for introducing fluid (such as a wash buffer) into the mixing channel. The plurality of sample inlet channels can be in any arrangement. For example, the cell culture inlet channel can be upstream of the particle inlet channel which is upstream of the fluid inlet channel. In other examples, the particle inlet channel can be upstream of the cell culture inlet channel which is upstream of the fluid inlet channel.

The cell culture inlet channel, the particle inlet channel, and the fluid inlet channel can fluidly converge at a mixing intersection. The cell culture inlet channel forms a path for fluid flow from the cell culture chamber to the mixing intersection. The particle inlet channel forms a path for fluid flow from a particle inlet to the mixing intersection. The fluid inlet channel forms a path for fluid flow from a fluid inlet to the mixing intersection. As used herein, a path of fluid flow can be represented pictorially in the figures by an arrow to indicate the direction of fluid flow through the path of fluid flow.

The mixing channel comprising the cell culture inlet channel, the particle inlet channel, and the fluid inlet channel has a height and a width. In some embodiments, the mixing channel has a height of at least 50 microns (for example, 75 microns or greater, 100 microns or greater, 120 microns or greater, 150 microns or greater, 175 microns or greater, 200 microns or greater, 250 microns or greater, 300 microns or greater, 350 microns or greater, 400 microns or greater, or 500 microns or greater). In some embodiments, the mixing channel has a height of 500 microns or less (for example, less than 500 microns, 450 microns or less, 400 microns or less, less than 400 microns, 350 microns or less, 300 microns or less, less than 300 microns, 275 microns or less, 250 microns or less, 200 microns or less, 150 microns or less, 100 microns or less, or 50 microns or less). In some embodiments, the mixing channel has a height of from 50 microns to 500 microns (for example, from 100 microns to 500 microns, from 200 microns to 500 microns, from 100 microns to 350 microns, or from 200 microns to 500 microns).

The mixing channel can have a width of at least 50 microns (for example, 75 microns or greater, 100 microns or greater, 120 microns or greater, 150 microns or greater, 175 microns or greater, 200 microns or greater, 250 microns or greater, 300 microns or greater, 350 microns or greater, 400 microns or greater, or 500 microns or greater). In some embodiments, the mixing channel has a width of 500 microns or less (for example, less than 500 microns, 450 microns or less, 400 microns or less, less than 400 microns, 350 microns or less, 300 microns or less, less than 300 microns, 275 microns or less, 250 microns or less, 200 microns or less, 150 microns or less, 100 microns or less, or 50 microns or less). In some embodiments, the mixing channel has a width of from 50 microns to 500 microns (for example, from 100 microns to 500 microns, from 200 microns to 500 microns, from 100 microns to 350 microns, or from 200 microns to 500 microns).

The ratio of the culture chamber width to the to the largest cross-sectional dimension of the mixing channel is at least 2:1, at least 3:1, at least 4:1, at least 5:1, at least 6:1, at least 7:1, at least 8:1, at least 9:1, at least 10:1, at least 12:1, at least 15:1, at least 18:1, at least 20:1, at least 25:1, at least 50:1, at least 75:1, at least 100:1, at least 150:1, at least 200:1, at least 250:1, at least 300:1, at least 350:1, at least 400:1, at least 450:1, or at least 500:1. In some embodiments, the ratio of the culture chamber width to the largest cross-sectional dimension of the mixing channel is from 5:1 to 500:1, from 5:1 to 200:1, from 5:1 to 100:1, from 2:1 to 25:1, from 5:1 to 20:1, from 5:1 to 15:1, from 6:1 to 25:1, from 6:1 to 20:1, from 6:1 to 12:1, from 8:1 to 25:1, or from 10:1 to 25:1. A ratio of the culture chamber width to the largest cross-sectional dimension of the mixing channel which is greater than one (e.g., 2:1) defines a narrowing of channel width at the mixing channel inlet.

One or more channels in the microfluidic device can, in some embodiments, comprise a fluid mixing mechanism which facilitates the mixing of fluids flowing through the device. A fluid mixing mechanism induces turbulent flow so as to mix flowing fluids. Suitable mixing mechanisms include a serpentine or tortuous channel, a channel protrusion or indentation, a channel curvature, among other known mechanisms.

In some embodiments, a fluid mixing mechanism can be present in the mixing channel and/or in an isolation channel of the microfluidic device. For example, the microfluidic device can include an isolation channel that fluidly connects to the mixing channel to an isolation outlet. The isolation channel can form a part of the mixing channel or can be separate. In some embodiments, the isolation channel defines a path for fluid flow from the mixing channel to an isolation outlet. The isolation channel can comprise a serpentine geometry which enhances mixing as the fluids combine. Referring to FIG. 4, an isolation channel (230) having a serpentine geometry can be positioned within the device at a location advantageous for fluid mixing, for example, between a mixing intersection and a collection chamber. In some embodiments, the isolation channel is positioned immediately adjacent a mixing intersection (e.g., immediately downstream).

The isolation channel can have a similar or narrowed width as compared to the mixing channel width. In some embodiments, the isolation channel can have a narrowed width as compared to the mixing channel width by at least several means. For example, the isolation channel can comprise one or more channel constriction domains (see, for example, the channel constriction domains (232) which form the narrowed width in the isolation channel in FIG. 4) disposed within the isolation channel between the isolation channel inlet and the isolation channel outlet. The channel constriction domains can produce a local vortex flow profile of fluid flowing in the device. In some embodiments, the isolation channel comprises at least one, at least two, at least three, at least four, at least five, at least six, at least seven, at least eight, at least nine, or at least ten channel constriction domains. Any one or more channel constriction domains can be a protrusion and/or indentation in the channel sidewalls. The protrusion and/or indentation can have any shape, for example rounded, linear, triangular, irregular, etc. The protrusion and/or indentation can encircle the inner walls of the channel (e.g., as a ring), or one or more protrusions and/or indentation can be positioned on one or more inner sidewalls of the channel. Inclusion of a channel constriction domain can increase fluid flow turbulence and fluid mixing, where desirable.

Devices disclosed herein can include a collection chamber (240) fluidly connected to the isolation outlet (234). In some embodiments, the device can further comprise a magnet operatively coupled to the collection chamber to produce a magnetic field within the collection chamber. The magnet can be any magnet capable of providing a magnetic field within the collection chamber. In some embodiments, the magnetic field can include an oscillating magnetic field. An oscillating magnetic field is a magnetic field which varies regularly (e.g., automated periodic regularity) or irregularly (e.g., by user-based controls) over time. An oscillating magnetic field includes dynamic changes in the spatial orientation of the north and south magnetic poles, such that the direction of the magnetic field changes over time. Such changes can be cyclical or irregular. Inclusion of an oscillating magnet capable of providing an oscillating magnetic field within the collection chamber can induce magnetic probes (e.g., magnetic beads or particles) within the collection chamber to dynamically move inside the collection chamber along a direction of the magnetic field. As the direction of the magnetic field changes, the directional movement of magnetic particles within the collection chamber also changes. This can be used to foster interaction (and association/binding) between the magnetic particles and targets present in a fluid in the collection chamber. In some embodiments, the magnetic field can be obtained from a permanent magnet. The permanent magnet can be removed when not in use, for example, to switch off the magnetic field.

In some embodiments, the magnet can have any shape such as a toroidal shape. In some embodiments, the magnet comprises a Helmholtz coil or a permanent magnet.

The magnetic field can be present over the entire width of the collection chamber. In some embodiments, the magnetic field can be over a portion of the collection chamber, for example over at least 50%, at least 60%, at least 70%, at least 80%, at least 90%, or at least 95% of the entire width of the collection chamber. Further, the magnetic field can be over other portions of the microfluidic device. For example, the magnetic field can be over one or more of a portion of or the entirety of the mixing channel, the mixing intersection, the particle inlet channel, or other components.

In some embodiments, the device can comprise a pump operably coupled to the microfluidic device. The pump can be any pump known in the art capable of inducing fluid flow within the device. In some embodiments, the pump can impart negative pressure within the device, thereby pulling fluid through a channel. Examples of suitable pumps can be found in US20170065978 and US20170001197, each of which are incorporated by reference in their entireties.

Figure 6:
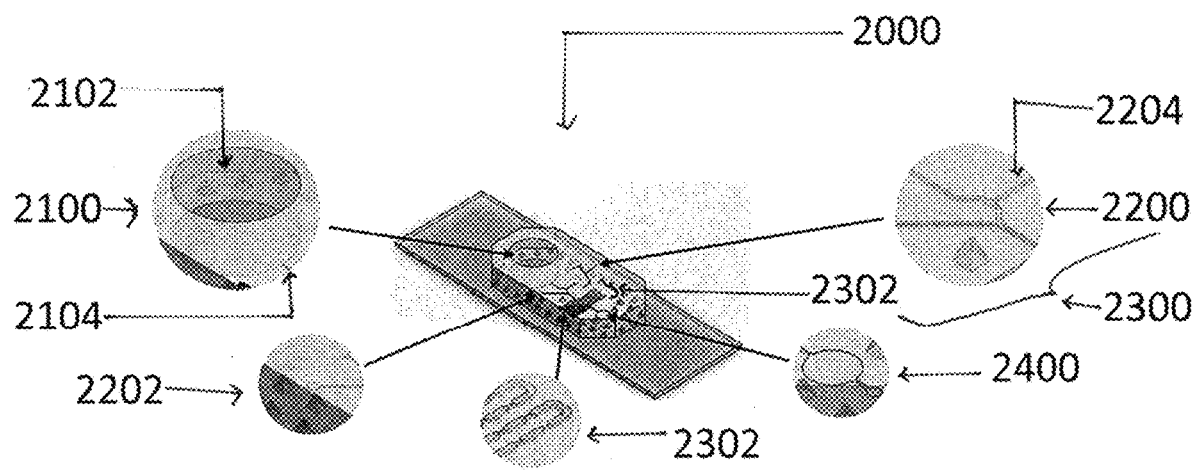
FIG. 6 illustrates an embodiment of a microfluidic device.

Turning now to FIG. 6, also disclosed is a microfluidic device (2000) comprising a cell culture chamber (2100) comprising a cell culture inlet (2102) and a cell culture outlet (2104), a fluid inlet channel (2202) and a particle inlet channel (2204), wherein the cell culture outlet (2104), the fluid inlet channel (2202), and the particle inlet channel (2204) fluidly converge at a mixing intersection (2200); a mixing channel (2300) fluidly connected to the mixing intersection (2200) and defining a path for fluid flow from the mixing intersection to a mixing outlet, wherein the ratio of a width of the cell culture chamber (2100) to the largest cross-sectional dimension of the mixing channel (2300) is at least 5:1; and a collection chamber (2400) fluidly connected to the mixing outlet and comprises a magnet operatively coupled to the collection chamber (2400) to produce a magnetic field within the collection chamber. The mixing channel (2300) can comprise an isolation channel (2302) disposed between the mixing intersection (2200) and the mixing outlet.

Another aspect of the microfluidic devices provided herein relates to multiplexed microfluidic devices which contain two or more sets of chambers and/or channels including the cell culture chamber, the mixing channel, the isolation channel, and the collection chamber. Configuring two or more of such channels and/or chambers on a single microfluidic device can increase sample-processing throughput and/or allow for parallel processing of at least two samples or portions of the sample for different fractions or manipulations. Two or more chambers and/or channels can be arranged in series, in parallel or in a combination thereof.

In some embodiments of a parallel multiplexed microfluidic device, two or more mixing channels can have separated sample inlets disposed on the same microfluidic device. Such arrangement can be employed for multiple fluid samples. Alternatively, the plurality of the mixing channels can be connected to the same sample inlets for parallel processing of the same fluid sample. Additionally, the two or more mixing channels can have separated outlets disposed on the same microfluidic device or be connected to the same outlet. In one or more embodiments, multiplexed microfluidic devices are contemplated having as many as 96 sample inlets.

The microfluidic devices of the present disclosure can be used in combination with the various compositions, devices, methods, products, and applications disclosed herein. In some embodiments, the microfluidic devices can be a stand-alone microfluidic device. In some embodiments, one or more microfluidic devices can be integrated as part of an equipment, a module or a system. In other embodiments, one or more microfluidic devices can be fluidically coupled to an equipment, a module or a system.

By way of example only, one or more microfluidic device and/or multiplexed microfluidic devices can be fluidically coupled to a detection module. As used herein, the term "fluidically coupled" refers to two or more devices and/or modules connected in an appropriate manner such that a fluid can pass or flow from one device or module to the other device or module. When two or more devices and/or modules are fluidically coupled together, additional devices and/or modules can be present between the two or more devices and/or modules.

Alternatively, two the two or more devices and/or modules can be connected such that a fluid can pass or flow directly from a first device or module to a second device or module without any intervening devices or modules. Two or more devices or modules can be fluidically coupled, for example, by connecting an outlet of a first device or module to an inlet of a second device or module using tubing, a conduit, a channel, piping or any combinations thereof.

The detection module can perform any method of detection disclosed herein or other methods known in the art. In some embodiments, the detection module can include a sample-treatment module before the sample is detected for analysis. For example, the exosomes (including or excluding the immunomagnetic particles) can be subjected to immunostaining before detection by microscopy. Examples of the detection module can include, without limitations, a microscope (e.g., a brightfield microscope, a fluorescence microscope, or a confocal microscope), a spectrophotometer (e.g., UV-Vis spectrophotometer), a cell counter, a biocavity laser (see, e.g., Gourley et al., J. Phys. D: Appl. Phys. 36: R228-R239 (2003)), a mass spectrometer, an imaging system, an affinity column, a particle sorter, e.g., a fluorescent activated cell sorter, capillary electrophoresis, a sample storage device, and sample preparation device. In some embodiments, a computer system can be connected to the detection module, e.g., to facilitate the process of sample treatment, detection and/or analysis.

Moreover, although depicted with respect to particular microfluidic handling devices, it will be appreciated that the protocol can be likewise be implemented in various other liquid handling vessels as exemplified in the working examples.

Methods of Making

The devices described herein can be made of any material that is compatible with a fluid sample. In some embodiments, the material for fabrication of the devices described herein can be penetrated by a magnetic field. In some embodiments, the material for fabrication of the devices described herein can be substantially transparent so that the sample therein can be photocleaved in situ or it can be viewed under a microscope, e.g., for in situ analysis of the magnetically-labeled exosomes. Exemplary materials that can be used to fabricate the microfluidic devices described herein can include, but are not limited to, glass, co-polymer, polymer or any combinations thereof. Exemplary polymers include, but are not limited to, polyurethanes, rubber, molded plastic, polymethylmethacrylate (PMMA), polycarbonate, polytetrafluoroethylene (TEFLON™) polyvinylchloride (PVC), polydimethylsiloxane (PDMS), polysulfone, and ether-based, aliphatic polyurethane.

The methods used in fabrication of any embodiments of the microfluidic devices described herein can vary with the materials used, and include 3D printing methods, soft lithography methods, microassembly, bulk micromachining methods, surface micro-machining methods, standard lithographic methods, wet etching, reactive ion etching, plasma etching, stereolithography and laser chemical three-dimensional writing methods, solid-object printing, machining, modular assembly methods, replica molding methods, injection molding methods, hot molding methods, laser ablation methods, combinations of methods, and other methods known in the art.

In specific embodiments, the microfluidic devices described herein can be fabricated using a 3D printer. For example, methods of making the microfluidic devices can include providing three pieces of PDMS molds including a base, wall, and top magnet holder as shown in FIG. 7. The mold can be printed out by a 3D printer. The molds can be coated with Sportline palladium at a thickness of 20 nm followed by assembly using methods known in the art. The PDMS cell chamber can be sized so that when it is filled, the cell culture chamber has an open end for chamber plug. PDMS can be cast by a 10:1 ratio with a linker reagent and incubated at a temperature of 40° C. for 6 hours. After the PDMS is cured, it can be peeled out easily. Chip inlets and outlet can be punched by using puncher. The PDMS chips can then be post-bond on a hot pad at the temperature of 40° C. for 5 mins. The chips can be cleaned using DI water, and sterilized by autoclave (at 121° C. for 30 mins).

Methods of Use

As discussed herein, the process and associated devices can be used for isolating, capturing, engineering, and releasing engineered extracellular vesicles and various vesicle-like biological structures. In certain embodiments, the engineered extracellular vesicles are immunogenic exosomes. As used herein, the term "exosome" generally refers to externally released vesicles originating from the endosomic compartment or any cells, e.g., tumor cells (e.g., prostate cancer cells), and immune cells (e.g., antigen presenting cells, such as dendritic cells, macrophages, mast cells, T lymphocytes or B lymphocytes). Exosomes are generally membrane vesicles with a size of about 20-150 nm that are released from a variety of different cell types including tumor cells, red blood cells, platelets, lymphocytes, and dendritic cells. Exosomes can be formed by invagination and budding from the membrane of late endosomes. They can accumulate in cytosolic multivesicular bodies (MVBs) from where they can be released by fusion with the plasma membrane. Without wishing to be bound by theory, the process of vesicle shedding is particularly active in proliferating cells, such as cancer cells, where the release can occur continuously. When released from tumor cells, exosomes can promote invasion and migration. Thus, in some embodiments, the immunomagnetic particles described herein can be used to capture exosomes originating from cancer cells. Depending on the cellular origin, exosomes can recruit various cellular proteins that can be different from the plasma membrane including MHC molecules, tetraspanins, adhesion molecules and metalloproteinases. Among many subtypes of exosomes, the immunogenic exosomes with an intrinsic payload of MHC class I and II molecules and other co-stimulatory molecules are able to mediate immune responses, which opens up opportunities for the development of novel cancer vaccines and delivery in immunotherapy.

Accordingly, also provided herein are methods of producing immunogenic exosomes in a microfluidic device or other suitable vessel disclosed herein. The methods of producing immunogenic exosome complexes can comprise introducing cells into a suitable vessel, or into the cell culture chamber of the microfluidic device. The cells can include any cells from which extracellular vesicles can be obtained. Such cells include dendritic cells, stem cells, immune cells, megakaryocyte progenitor cells, macrophages, or combinations thereof.

The method for producing immunogenic exosomes can further include culturing the cells under conditions allowing release of exosomes. In some embodiments, the methods can include enriching or expanding the number of exosomes present in the cell sample through mediating their parent cell growth using stimulations known in the art. Conventional methods for culturing a parent cell to produce exosomes are known in the art and can be used in the methods disclosed herein. In some embodiments, the cells can be cultured for a period of time, e.g., at least about 30 mins, at least about 45 mins, at least about 1 hour, at least about 2 hours, at least about 3 hour, at least about 5 hours, at least about 6 hours, at least about 8 hours, at least about 10 hours, at least about 12 hours, at least about 15 hours, at least about 18 hours, at least about 20 hours, at least about 24 hours, at least about 30 hours, at least about 36 hours, at least about 40 hours, or at least about 48 hours.

The method for producing immunogenic exosomes complex can further comprise mixing the cell culture comprising exosomes with immunomagnetic particles for capturing the exosomes and a wash solution to form a mixture. In some embodiments, the methods include introducing the exosomes from the cell culture into a mixing channel and mixing the exosomes with immunomagnetic particles and a wash buffer to form a mixture. The immunomagnetic particles can be introduced into the mixing channel via the particle inlet channel and the wash buffer can be introduced into the mixing channel via the fluid inlet channel.

The immunomagnetic particles can selectively bind to the exosomes present in the cell culture to form exosome-bound immunomagnetic particles. Accordingly, the method can include allowing the exosomes to react with the immunomagnetic particles. The immunomagnetic particles can include a magnetic particle and be of any shape, including but not limited to spherical, rod, elliptical, cylindrical, and disc. In some embodiments, magnetic particles having a substantially spherical shape and defined surface chemistry can be used to minimize chemical agglutination and non-specific binding. As used herein, the term "magnetic particles" can refer to a nano- or micro-scale particle that is attracted or repelled by a magnetic field gradient or has a non-zero magnetic susceptibility. The magnetic particles can be ferromagnetic, paramagnetic or super-paramagnetic. In some embodiments, magnetic particles can be super-paramagnetic.

The magnetic particles can range in size from 1 nm to 5 microns. For example, magnetic particles can be about 500 nm to about 5 microns in size. In some embodiments, magnetic particles can be about 1 micron to about 5 microns in size. In some embodiments, magnetic particles can be about 1 micron to about 3 microns in size. Magnetic particles are a class of particles which can be manipulated using magnetic field and/or magnetic field gradient. Such particles commonly consist of magnetic elements such as iron, nickel and cobalt and their oxide compounds. Magnetic particles (including nanoparticles or microparticles) are well-known and methods for their preparation have been described in the art. Magnetic particles are also widely and commercially available. A particularly preferred particle is a magnetic particle having a graphene-oxide layer or coating which is comprised of graphene-oxide nanosheets, as described in US 2018/0100853, filed Oct. 9, 2017, incorporated by reference in its entirety herein.

The magnetic particles can be coated with a plurality of linkers comprising respective affinity probes (molecules) for capturing the target (such as an antigen peptide or antigenic epitope thereof) having no adverse effect on the magnetic property. In this regard, the magnetic particle can be functionalized with an organic moiety or functional group and photocleavable linker that can connect the magnetic particle to respective affinity probes for capturing the exosomes. Such organic moiety or functional groups can typically comprise a direct bond or an atom such as oxygen or sulfur, a unit such as amino groups, carboxylic acid groups, epoxy groups, tosyl groups, silica-like groups, carbonyl groups, amide groups, SO, $SO_2$, $SO_2NH$, SS, or a chain of atoms.

In certain embodiments, the magnetic particles can be coated with one member of an affinity binding pair that can facilitate the conjugation of the magnetic particles to the affinity probe for capturing the exosomes. The term "affinity binding pair" or "binding pair" refers to first and second molecules that specifically bind to each other. One member of the binding pair is conjugated with first part to be linked while the second member is conjugated with the second part to be linked. Exemplary binding pairs include any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin, biotin-neutravidin, hormone [e.g., thyroxine and cortisol-hormone binding protein, receptor-receptor agonist, receptor-receptor antagonist (e.g., acetylcholine receptor-acetylcholine or an analog thereof), IgG-protein A, IgG-protein G, IgG-synthesized protein AG, lectin-carbohydrate, enzyme-enzyme cofactor, enzyme-enzyme inhibitor, and complementary oligonucleotide pairs capable of forming nucleic acid duplexes), and the like. The binding pair can also include a first molecule which is negatively charged and a second molecule which is positively charged.

One example of using binding pair conjugation is the biotin-avidin, biotin-streptavidin or biotin-neutravidin conjugation. Accordingly, in some embodiments, the magnetic particles can be coated with avidin-like molecules (e.g., streptavidin or neutravidin), which can be conjugated to biotinylated linkages for use as capturing molecules.

In some embodiments, the magnetic particles can be further functionalized with a cleavable chemical moiety that can link the magnetic particles to the affinity probe for capturing the exosomes, and is susceptible to an externally-applied cleavage agent/conditions, e.g., UV light, pH, redox potential or the presence of degradative molecules such as enzymes. In specific examples, the cleavable linker can be conjugated to a member of a binding pair (such as biotin) at one functional end to link to the magnetic particles, and the other functional end provides an affinity probe for capturing exosomes. Thus, after the exosomes bound magnetic particles are separated from a fluid sample, the exosomes can be separated from the magnetic particles, if needed, by cleaving the cleavable chemical moiety between the magnetic particles and the affinity probe.

Exemplary cleavable linking groups include, but are not limited to, photocleavable and redox cleavable linking groups (e.g., —OC(O)NH—, —S—S—, and —C(R)$_2$—S—S—, wherein R is H or $C_1$-$C_6$ alkyl); phosphate-based cleavable linking groups (e.g., —O—P(O)(OR)—O—, —O—P(S)(OR)—O—, and —O—P(S)(H)—S—, wherein R is optionally substituted linear or branched $C_1$-$C_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$_A$C(O)NHCHR$_B$C(O)—, where R$_A$ and R$_B$ are the R groups of the two adjacent amino acids).

In some embodiments, the cleavable linking group is a photocleavable group that can be cleaved by UV light. Specific examples of photocleavable groups include ortho nitrobenzyl derivatives and benzylsulfonyl such as 6-nitro-veratryloxycarbonyl (NVOC), 2-nitrobenzyloxycarbonyl (NBOC), α,α-dimethyl-dimethoxybenzyloxycarbonyl (DDZ), ortho-nitrobenzyl (ONB), 1-(2-nitrophenyl)ethyl (NPE), alpha-carboxy-2-nitrobenzyl (CNB), 4,5-dimethoxy-2-nitrobenzyl (DMNB), 1-(4,5-dimethoxy-2-nitrophenyl)ethyl (DMNPE), 5-carboxymethoxy-2-nitrobenzyl (CMNB), and (5-carboxymethoxy-2-nitrobenzyl)oxy)carbonyl (CMNCBZ). It will be appreciated that the substituents on the aromatic core are selected to tailor the wavelength of absorption, with electron donating groups (e.g., methoxy) generally leading to longer wavelength absorption. For example, nitrobenzyl (NB) and nitrophenylethyl (NPE) are modified by addition of two methoxy residues into 4,5-dimethoxy-2-nitrobenzyl and 1-(4,5-dimethoxy-2-nitrophenyl)ethyl, respectively, thereby increasing the absorption wavelength range to 340-360 nm. Additional examples of the photoremovable protecting groups include multiply substituted nitro aromatic compounds containing a benzylic hydrogen ortho to the nitro group, wherein the substituent may include alkoxy, alkyl, halo, aryl, alkenyl, nitro, halo, or hydrogen. Other materials which may be used include o-hydroxy-α-methyl cinnamoyl derivatives, photocleavable groups based on the coumarin system, such as BHC (such as described in U.S. Pat. No. 6,472,541, the disclosure of which is incorporated by reference herein), photocleavable group comprising the pHP group (such as described in Givens et al., J. Am. Chem. Soc. 122 2687-2697 (2000), the disclosure of which is incorporated by reference herein), ketoprofen derived linkers, other ortho-nitro aromatic core scaffolds include those that trap nitroso byproducts in a hetero Diels Alder reaction (generally discussed in U.S. Patent Application No. 2010/0105120, the disclosure of which is incorporated by reference herein), nitrodibenzofurane (NDBF) chromophore, or a diazo-azide. Further examples of photocleavable groups may be found in, for example, Patchornik, J. Am. Chem. Soc. (1970) 92:6333 and Amit et al., J. Org. Chem. (1974) 39:192, the disclosures of which are incorporated by reference herein.

As discussed above, a photocleavable group is one whose covalent attachment to a molecule (such as to a member of a binding pair example biotin at one functional end and the other functional end to an affinity probe) is cleaved by exposure to light of an appropriate wavelength. In one aspect, release of the affinity probe and/or binding pair occurs when the conjugate is subjected to ultraviolet light or near ultraviolet light. For example, photorelease of the affinity probe may occur at a wavelength ranging from about 200 to 380 nm (the exact wavelength or wavelength range will depend on the specific photocleavable group used, and could be, for example, 200, 210, 220, 230, 240, 250, 260, 270, 280, 290, 300, 310, 320, 330, 340, 350, 360, 370, or 380 or some range therebetween). In another aspect, release of the affinity probe may occur when the conjugate is subjected to visible light. For example, photorelease of the affinity probe may occur at a wavelength ranging from about 380 to 780 nm (the exact wavelength or wavelength range will depend on the specific photocleavable group used, and could be, for example, 380, 400, 450, 500, 550, 600, 650, 700, 750, or 780, or some range therebetween).

As described herein, the magnetic particles further comprise an affinity probe (also referred to herein as a molecule for capturing the exosomes or capturing molecule). As used herein, the term "affinity probe" or "capturing molecule" refers to any molecule, cell or particulate material. Suitable affinity probes comprising a magnetic particle are described in US20170065978 and US20170001197, each of which are incorporated by reference in their entireties. The affinity probes can comprise a binding element which specifically binds the target (exosome or other extracellular vesicles) of interest. For example, the binding element can be a nucleic acid oligomer, antibody, enzyme, hormone, growth factor, cytokine (e.g., inflammatory cytokines), proteins, peptide, prion, lectin, oligonucleotide, carbohydrate, lipid, molecular and chemical toxin or other binding element which has high affinity and high specificity for the target, and specificity for a designated surface protein on the target. One or more binding elements (e.g., a peptide) can be attached to the magnetic particle via the cleavable linker by methods known in the art. Generally, a binding element has an affinity constant (Ka) greater than about $10^5$ M$^{-1}$ (e.g., $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, and $10^{12}$ M$^{-1}$ or more) with the target, particularly exosome or other extracellular vesicles.

In certain embodiments, the affinity probe includes an antigenic peptide or antigenic epitope thereof. As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody or a T cell receptor (TCR) if presented by MHC molecules. The term "antigen," as used herein, also encompasses T-cell epitopes. An antigen is additionally capable of being recognized by the immune system and/or being capable of inducing a humoral immune response and/or cellular immune response leading to the activation of B- and/or T-lymphocytes. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

As described above, the affinity probe (antigen) can be a protein or a peptide. In some embodiments, the protein or peptide can be essentially any protein that can activate immune cells and/or prime immune-responses, bind to a rare cell, e.g., a circulating tumor cell, a stem cell and/or a microbe. By way of example only, if the target species is cancer, exemplary proteins or peptides or other molecule that can be used to generate cancer-affinity probes can include, but are not limited to, MAGE-A3, gp-100, HER-2, p53, PSA-1, or MART-1, EGFR, ERCC1, CXCR4, EpCAM, CEA, ErbB-2, E-cadherin, mucin-1, cytokeratin, PSA, PSMA, RRM1, androgen receptor, estrogen receptor, progesterone receptor, IGF1, cMET, EML4, or leukocyte associated receptor (LAR).

In some embodiments, the affinity probe can be an antibody or a portion thereof, or an antibody-like molecule. In some embodiments, the capturing molecule can be an antibody or a portion thereof, or an antibody-like molecule that is specific for detection of a rare-cell, e.g., a circulating tumor cell, a stem cell and/or a microbe biomarker. In some embodiments, the affinity probe can be an aptamer. In some embodiments, the affinity probe can be a DNA or RNA aptamer. In some embodiments, the affinity probe can be a cell surface receptor ligand. Exemplary, cell surface receptor ligands includes, for example, a cell surface receptor binding peptide, a cell surface receptor binding glycopeptide, a cell surface receptor binding protein, a cell surface receptor binding glycoprotein, a cell surface receptor binding organic compound, and a cell surface receptor binding drug. Additional cell surface receptor ligands include, but are not limited to, cytokines, growth factors, hormones, antibodies, and angiogenic factors. In some embodiments, any art-recognized cell surface receptor ligand that can bind to a rare cell, e.g., a circulating tumor cell, a stem cell and/or a microbe, can be used as an affinity probe on the magnetic particles described herein. In one or more embodiments, an affinity probe is selected to target an immunostimulatory molecule presented on the surface of the target (e.g., exosome), such as MHC class I molecule, an MHC class II molecule, an interleukin, TNFα, IFNγ, RANTES, G-CSF, M-CSF, IFNα, CTAPIII, ENA-78, GRO, I-309, PF-4, IP-10, LD-78, MGSA, MIP-1α, MIP-1β and combinations thereof. More preferably, upon binding of the affinity probe (and subsequent release of the target), the resulting engineered target comprising the bound affinity probe enhances the immunogenic potential of the released target. For example, the binding of an MHC class I surface protein by the affinity probe creates a complex that will (in therapeutic use) enhance recognition and uptake of the engineered target by an antigen presenting cell for stimulation and activation of the immune system. The peptides are preferably 15 amino acid residues or less in length, more preferably 13 residues or less in length, even more preferably 12 residues or even 11 residues or less in length. Example affinity probes include those listed in the Table below:

|  | SEQ ID NO: |  | SEQ ID NO: |
|---|---|---|---|
| Peptide 1: SIINFEKL | 1 | Peptide 2: RSV M2 82-90 peptide sequence SYIGSINNI | 2 |
| Peptide 3: Fusion 85-93 peptide sequence KYKNAVTEL | 3 | Peptide 4: M187-195 peptide sequence NAITNAKII | 4 |
| MAGE-A1 161-169: EADPTGHSY | 5 | MAGE-A3 168-176: EVDPIGHLY | 6 |
| MAGEA-10 254-262: GLYDGMEHL | 7 | MAGEA3 112-120: KVAELVHFL | 8 |
| MAGEA1 278-286: KVLEYVIKV | 9 | MAGEA3 271-279: FLWGPRALV | 10 |
| MAGEA3 112-120 (alternative version): KVAEELVHFL | 11 | MAGEA2 157-166: YLQLVFGIEV | 12 |
| MAGE-A4 230-239: GVYDGREHTV | 13 | MAGE-C1 1083-1091: KVVEFLAML | 14 |
| MAGE-C2 191-200: LLFGLALIEV | 15 | MAGE-C2 336-344: ALKDVEERV | 16 |
| MAGEA3 97-105: TFPDLESEF | 17 | MAGEA5 5-12: HNTQYCNL | 18 |
| Prostate Specific Antigen 146-154: KLQCVDLHV | 19 | Carcinogenic Embryonic Antigen (CEA) 694-702: GVTYACFVSNL | 20 |
| Carcinogenic Embryonic Antigen (CEA) 652-660: TYACFVSNL | 21 | G250 (renal cell carcinoma) 217-225: HLSTAFARV | 22 |
| HER-2/neu 435-443: ILHNGAYSL | 23 | HER-2/neu 63-71: TYLPTNASL | 24 |
| HER-2 434-443: ILHDGAYSL | 25 | Neu/Her-2/Erbb2 proto-oncoprotein 66-74: TYVPANASL | 26 |
| gp100 (pmel17) 209-217: IMDQVPFSV | 27 | gp100-intron 4(170-178): VYFFLPDHL | 28 |
| gp100 (pmel17) 154-162: KTWGQYWQV | 29 | gp100 (pmel17) 476-485: VLYRYGSFSV | 30 |
| gp100 (pmel) 209-217: ITDQVPFSV YLEPGPVTV | 31 | gp100 (pmel) 280-288 (288V): | 32 |
| gp100: YLEPGPVTA | 33 | gp100 (pmel17) 25-33: KVPRNQDWL | 34 |
| gp100 (pmel17) 17-25: ALLAVGATK | 35 | gp100-intron 4 (170-178): VYFFLPDHL | 36 |
| HER-2/neu 369-377: KIFGSLAFL | 37 | p53 264-272: LLGRNSFEV | 38 |
| p53 187-197: GLAPPQHLIRV | 39 | p53 149-157: SLPPPGTRV | 40 |
| p53 139-147: KLCPVQLWV | 41 | p53 65-73: RMPEAAPPV | 42 |
| p53 103-111: YLGSYGFRL | 43 | Prostatic Acid Phosphatase-3 (PAP-3): FLGYLILGV | 44 |
| PSM P2 (prostate): ALFDIESKV | 45 | Prostate Stem Cell Antigen (PSCA) 14-22: ALQPGTALL | 46 |
| MelanA/MART 26-35: ELAGIGILTV | 47 | Prostate Specific Antigen-1 (PSA-1) 141-150: FLTPKKLQCV | 48 |
| MUC-1 12-20: LLLLTVLTV | 49 | Human Mena protein (overexpressed in breast cancer): GLMEEMSAL | 50 |
| HER-2/neu 689-697: RLLQETELV | 51 | HER-2/neu (85-94): LIAHNQVRQV | 52 |
| Prostate Specific Antigen-1 (PSA-1) 154-163: VISNDVCAQV | 53 | Prostate Specific Antigen-1 153-161: CYASGWGSI | 54 |
| PSA 65-73: HCIRNKSVI | 55 | EGF-R-479 350-359: KLFGTSGQKT | 56 |

-continued

| | SEQ ID NO: | | SEQ ID NO: |
|---|---|---|---|
| EGF-R 1138-1147: YLNTVQPTCV | 57 | VEGFR2 400-408: VILTNPISM | 58 |
| VEGFR2/KDR fragment 1 614-624: FSNSTNDILI | 59 | | |

It will be appreciated that the foregoing peptides, suitable for affinity probes, are also exemplary of active agents or moieties for surface loading onto the engineered target.

The immunomagnetic particles (that is magnetic particles bound to the affinity probe) are preferably formed before the mixing process. For example, the affinity probe (e.g., an antigenic peptide bound to biotin via a cleavable linker) and streptavidin coated magnetic particles are mixed together for an effective period of time for the biotinylated affinity probe linkages to substantially completely coat the entire surface of the avidin coated particles.

Thus, the affinity probe is preferably added to the streptavidin coated magnetic particles for a period of time, before adding the exosome containing cell culture. In such embodiments, the affinity probe can be first added to the streptavidin coated magnetic particles for a period of time sufficient for at least a portion of the added amount of affinity probe to bind with the streptavidin coated magnetic particles (and preferably for complete binding of affinity probe so as to coat the entire surface of the particle with probe linkages extending therefrom).

The exosomes present in the exosome containing cell culture are then added into the same fluid sample, where the exosomes can bind to the affinity probe, which have already formed a conjugate with the streptavidin coated magnetic particles.

In some embodiments, the immunomagnetic particles can be separately formed before being introduced into the mixing channel of the device.

The amount of the immunomagnetic particles required to be added into the sample can depend on a number of factors, including, but are not limited to, volume of the sample to be processed, valency of the magnetic particles available for conjugation with the affinity probe, expected abundance of the exosomes present, and any combinations thereof. Too high amounts of the immunomagnetic particles added into the device can induce non-specific binding and/or clogging inside the microfluidic device. Too low amounts of the immunomagnetic particles can result in a low capture efficiency. One skilled in the art can determine the concentration of the immunomagnetic particles and capturing molecules.

The exosomes can be allowed to mix with the immunomagnetic particles for any period of time, e.g., seconds, minutes or hours. In some embodiments, the exosomes can be mixed with the immunomagnetic particles for at least about 1 min, at least about 2 mins, at least about 5 mins, at least about 10 mins, at least about 15 mins, at least about 30 mins, at least about 1 hour, at least about 2 hours or more. A person having ordinary skill in the art can readily determine an optimum time for mixing time, based on a number of factors, including, but not limited to, the affinity of the immunomagnetic particles with the exosomes, concentrations, mixing temperature and/or mixing speed. However, in one or more embodiments, exosomes are mixed with the particles for 1 hour or less.

The exosomes and immunomagnetic particles can be introduced into the sample inlets of the microfluidic device at any flow rate that provides a sufficient residence time for the mixture to retain in the mixing channel and isolation channel of the microfluidic device described herein. In some embodiments, the samples can be introduced at a flow rate of between 0.1 uL/min to 1 uL/min. The sample fluids can be introduced into the inlet of the microfluidic device by any methods known to a skilled artisan. For example, a flow generator can be connected to at least one of the inlets and the outlet of the microfluidic device described herein. Non-limiting examples of a flow generator can include a peristaltic pump, a syringe pump and any art-recognized pump that can be generally used to flow a fluid through the microfluidic device.

The method of producing immunogenic engineered targets can further include capturing the exosomes bound to the immunomagnetic particles by applying a magnetic field within a collection or engineering chamber. In some embodiments, the magnet has a strong magnetic field strength sufficient to create a magnetic field gradient to cause the magnetically-labeled exosomes to separate from the fluid sample in the collection chamber. The immobilized magnetically-labeled exosomes can be removed from the microfluidic device or reaction vessel for further processing. Preferably, the captured exosomes are further engineered and loaded with additional active moieties on the surface or internally as discussed herein. Subsequently, the method includes photolytically cleaving the exosomes bound to the immunomagnetic particles for releasing intact exosomes coated with active moieties or loaded internally with active agents.

The released target (exosomes) can be provided as a pharmaceutical composition. The pharmaceutical composition can include the immunogenic exosomes and a pharmaceutically acceptable excipient. It will be appreciated that the active moieties can be tailored to provide either a specific adaptive immune response against a target condition, or can be selected more generally to activate the innate immune system against a variety of infections or conditions.

The methods described herein can be used to process samples in real time. For example, the methods allow real-time, continuous harvesting and antigenic modification of exosomes with subsequent photo-release downstream on-demand.

As described herein the methods can be used to produce an immunogenic exosome complex or other immunogenic vesicle-like structures. In certain embodiments, the immunogenic exosome complex can comprise an antigen peptide conjugated to a surface of an exosome. The methods described herein for making the immunogenic exosome complex provides complexes with a significantly higher activation rate for T-cells than non-engineered exosomes. In some examples, the immunogenic exosome complex can activate T-cell by at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% compared to a native exosome. Because of the improved activation rate, the immunogenic complexes described herein can be used in cancer immunotherapy.

Accordingly, methods of treating disease in a subject using the immunogenic complex are disclosed. The method can include administering to the subject a composition comprising an immunogenic complex. In some embodiments, the disease can be an infection. In some examples, the disease can be cancer. The method can further comprise administering a chemotherapeutic agent that has been loaded into the target.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

The devices, systems, and methods of the appended claims are not limited in scope by the specific devices, systems, and methods described herein, which are intended as illustrations of a few aspects of the claims. Any devices, systems, and methods that are functionally equivalent are intended to fall within the scope of the claims. Various modifications of the devices, systems, and methods in addition to those shown and described herein are intended to fall within the scope of the appended claims. Further, while only certain representative devices, systems, and method steps disclosed herein are specifically described, other combinations of the devices, systems, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

By way of non-limiting illustration, examples of certain embodiments of the present disclosure are given below.

EXAMPLES

The following examples set forth methods in accordance with the invention. It is to be understood, however, that these examples are provided by way of illustration and nothing therein should be taken as a limitation upon the overall scope of the invention.

Example 1: Microfluidic On-Demand Engineering of Exosomes Towards Cancer Immunotherapy Abstract: Extracellular nanovesicles (1 µm), particularly exosomes (30-150 nm), are emerging delivery system in mediating cellular communications, which have been observed for priming immune responses by presenting parent cell signaling proteins or tumor antigens to immune cells. In this example, a streamlined microfluidic cell culture platform for harvesting, antigenic modification, and photo-release of surface engineered exosomes directly in one workflow is provided. The PDMS microfluidic cell culture platform is replicated from a 3D-printed mold. By engineering antigenic peptides on exosome surface (e.g., gp-100, MART-1, MEGA-A3), the effective antigen presentation and T cell activation can be achieved. This has been demonstrated by using the on-chip culture of human blood-derived leukocytes for engineering secreted exosomes in real-time with melanoma tumor peptides. gp100-specific CD8 T cells which were purified from the spleen of 2 Pmel1 transgenic mice was tested. Significantly higher T-cell activation level (~30%) induced by engineered exosomes was observed compared to non-engineered exosomes. This microfluidic platform serves as an automated and highly integrated cell culture device for rapid, and real-time production of therapeutic exosomes that could advance cancer immunotherapy.

Methods and Materials

3D Printing and microfluidic device fabrication: three pieces of molds for PDMS chip fabrication, including a base, wall, and top magnet holder were provided. The mold was designed by using the SolidWorks® 2017 and printed out by the 3D printer of Project 1200 from 3D Systems. The multiple pieces had the finest structure in 50 µm, and with channel height at 50 µm. The cell culture chamber was designed with 1000 μm diameter, 500 μm height chamber. All molds were coated with Sportline palladium at the thickness of 20 nm. All three pieces were assembled using the PDMS chip. The PDMS was filled with a height under 500 μm, so the cell culture chamber left an open end for chamber plug. PDMS was cast by a 10:1 ratio with a linker reagent, and incubated at the temperature of 40° C. for 6 hours. After the PDMS cured, it could be peeled out easily. Chip inlets and outlet were punched by using 0.75 mm puncher. Piranha treated glass and PDMS were both high-voltage plasma for at least 30 seconds. The PDMS chips were then post-bond on the hot pad at the temperature of 40° C. for 5 mins. The chips were cleaned by DI water, and sterilized by autoclave (at 121° C. for 30 mins).

On-chip cell culture and exosome collection, engineering, and releasing: The cell cartridges (8 mm coverslip) were first cleaned with distilled water, and air dried inside the bio-hood. Then, they were autoclaved at 121° C. for 30 mins. The cartridges were set in a 24-well plate, and 500 μL of 0.1 mg/mL poly-D-lysine hydrobromide (MP Biomedicals) was added to each well, and incubated at the room temperature for 5 mins. 1 mL of MD water was added to each well for 3 mins and repeated for two times to clean the cell cartridges, and then sit for air dried inside the bio-hood and stored for future use.

4 μL β2-microglobulin (Sigma-Aldrich) and 10 μL of each protein (gp100, MAGE-A3, and MART-1) were mixed with 186 μL 1×PBS to the modification solution at a final volume of 200 μL. The B-inlet was kept blocked and the modification solution was pumped from A-inlet and the washing buffer from C-inlet through the chip at the volume flow rate of 1 μL/min for 10 mins, and 0.1 μL/min for 10 mins, and static was set for another 10 mins. A washing step was processed from both A-inlet and C-inlet at the volume flow rate of 1 μL/min for 15 mins. The bottom side magnet was removed and the near UV turned on to treat the major chamber for 10 mins. Another washing step from A-inlet and C-inlet was applied at the volume flow rate of 1 μL/min for 20 mins, to collect the calved exosome from outlet about 20 μL.

Ultracentrifugation and exosomes staining: The collected 20 μL exosomes were added to the ultracentrifuge tube and diluted to the final volume of 1 mL for centrifugation (Thermo Scientific™ Sorvall™ MTX) under 1,500 rcf for 30 mins. The supernatant was removed and transferred to a fresh ultracentrifuge tube. The mixture was then processed at the speed of 100,000 rcf for 1 hour. Exosomes were stained by the PKH67 Green Fluorescent Cell Linker Midi Kit for General Cell Membrane Labeling (Sigma-Aldrich). The staining solution was prepared with 2 μL of PKH67 and 1 mL of diluent C. Any remaining solution in the tube was discarded and 1 mL of Diluent C was added to re-suspend with gentle pipetting. The stained solution to the ultracentrifuge tube, pipette mixed, and reacted at the room temperature for 3.5 mins. 2 mL of FBS (exosome depleted) was added to quench the free dye. 1.5 mL of 0.971 M sucrose solution was added for density gradient centrifugation. Another 6.5 mL of complete media was added to raise the volume to 10 mL. The ultracentrifuge was set at 100,000 rcf for 1 hour. The supernatant was discarded and the dye ring washed carefully without reaching the center of the ring. Another 2 mL of 1×PBS was added to re-suspend the pellet. The ultracentrifuge at the speed of 100,000 rcf was ran for another 1 hour. The supernatant was sucked away, and another 100 μL of 1×PBS added to re-suspend the pellet. All steps were kept under sterile condition, and 1 μL of Penicillin-Streptomycin (ATCC®, Catalog #30-2300, Lot #63525409) was added to the collected exosome, to inhibit and kill bacteria remaining in the solution. The collected exosomes were stored at 4° C. for less than 1 week and stored at −20° C. for up to one month.

Exosome uptake: THP-1 cells (ATCC®, TIB-202™) was cultured by using ATCC-formulated RPMI-1640 Medium (ATCC®, Catalog #30-2001, Lot #64331683) plus 10% exosome-depleted FBS for the completed media. The monocytes cells were sub-cultured at the number of 8*105/mL, and by using the alternative media changing method. The cells were used for exosomes up taking experiment at the density of $5*10^5$/mL. 200 uL of the monocytes cells were transferred to the 48-well plate with totally 11 wells. 20 uL of normal exosome (NE) was added to 5 wells, also 20 μL of engineered exosome (EE) to another 5 wells, and one well left as a negative control. Time intervals were set at 0 hours, 0.5 hours, 1 hour, 2 hours, 3 hours, and 4 hours. At each time section, 100 uL of cell suspension media was removed from the cytocentrifuge, at the speed of 400 RPM for 4 mins. Glass slides were collected and 100 uL of Fixative Solution (ThermoFisher®, Catalog #R37814, Lot #17B285301) was added to cells' spot. The mixture incubated at room temperature for 18 mins, and then the solution removed. 100 μL of 1×PBS buffer was added to the cells' spot, and left to set at room temperature for 3 mins. 1×PBS buffer was removed and the cells' spot gently washed by the distilled water. The slide was dried without droplet remains on the slide, and 50 μL of 500 nM DAPI (ThermoFisher®, Catalog #D1306, Lot #1844202) applied to the cells' spot, covered from light, and incubated at room temperature for 4 mins. The DAPI solution was then quickly removed and followed with a sufficient amount of 1×PBS buffer twice with 2 mins for each time. The cells' spot was washed with distilled water, and briefly dried without droplet remain on the slide. One drop of ProLong™ Gold Antifade Mountant (ThermoFisher®, Ref #P10144, Lot1887458) was applied and the slide covered with 25×25 #1.5 coverslip without any trapped bubble. The slide was stored at room temperature for 24 hours before imaging under a confocal microscope.

Figure 5:
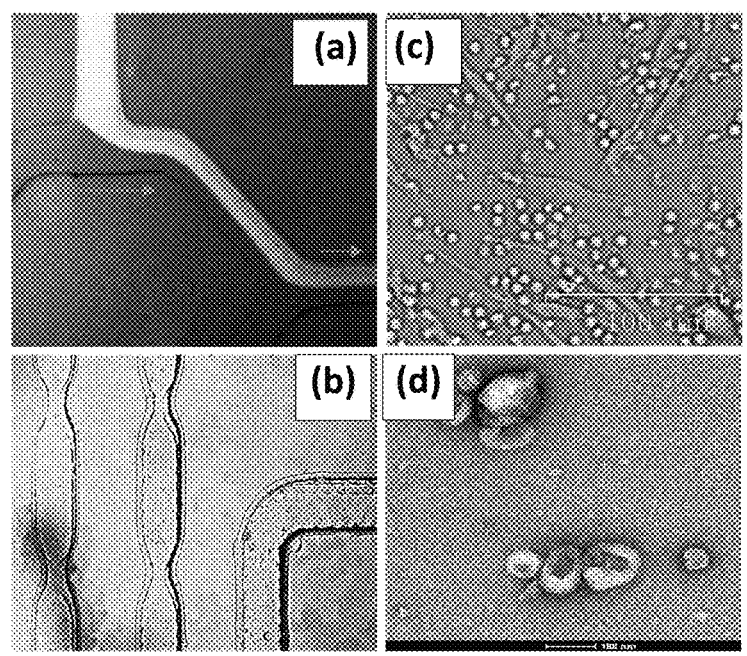
FIG. 5 shows images of (a) a microfluidic channel and flow; (b) mixing with microbeads; (d) morphology of cells; and (e) SEM image of released exosomes.

Results 3D-printing molded microfluidic cell culture device for on-inline harvesting exosomes: A facile and low-cost approach for making a PDMS-based on-chip cell culture microfluidic device using a 3D-printed mold has been developed. The culture chip contains an on-chip cell culture chamber with 1 mm diameter and 0.5 mm height for on-chip growing cells and collecting exosomes derived from culture medium at downstream. The cell culture chamber is left open on top for applying a PDMS-made, finger-push plug for medium exchange and pushing the medium to downstream collection channels. The bottom of the cell culture chamber has an outlet channel about 200 μm wide and 200 μm high (B-Inlet) for introducing culture medium to mix with immunomagnetic isolation beads (A-Inlet). The C-Inlet is used to introduce washing buffer driven by a syringe pump. FIG. 4 demonstrates the mixing process through the A-Inlet and B-Inlet and exit to exosome isolation channel (serpentine channel) under the observation of the fluorescence microscope using a fluorescence dye solution. FIG. 5(b) records the immunomagnetic beads mixing within the serpentine channel. Human blood-derived leucocytes were cultured in the culture device with the morphology showing in FIG. 5(c). Few red blood cells were still observed as a cup shape. The secreted exosomes were isolated, captured, and photo-released from the outlet of the chip, and characterized by SEM imaging shown in FIG. 5(d).

Figure 7A:
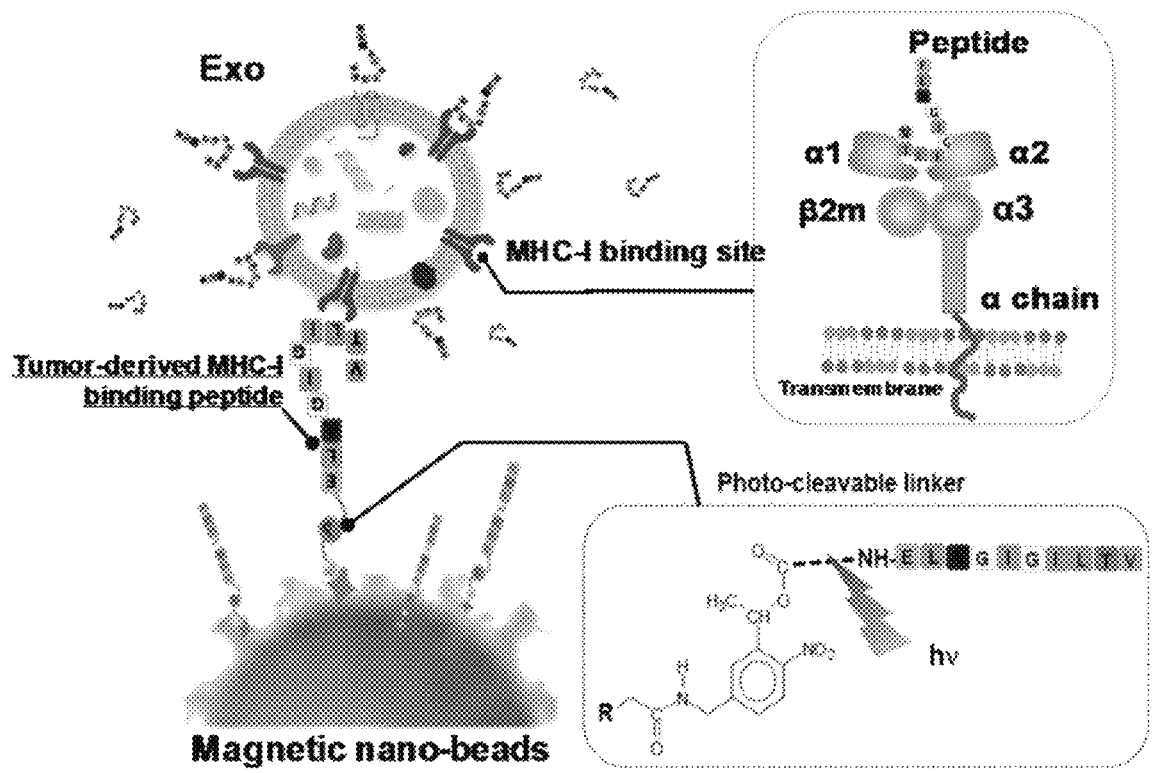
FIG. 7A shows an illustration of immunomagnetic capture and on-demand photo-release of MHC-I positive, immunogenic exosomes.

A photo-cleavable linker was conjugated with bi-function of biotin and NHS chemistry on both ends. The biotin group anchors the photo-cleavable linker to the surface of streptavidin immunomagnetic beads, and the NHS group conjugates the MHC-I peptide via the primary amine, as shown in FIG. 7A. The MHC class I molecules are heterodimers that consist of two polypeptide chains, α, and β2-microglobulin. The two chains are linked noncovalently via interaction of b2m and the α3 domain. The other two domains α1 and α2 are folded to make up a groove for binding to 8-10 amino acid peptides (MHC-I binding peptide). The MHC-I/peptide binding complex will be displayed to cytotoxic T cells consequently for triggering an immediate response from the immune system. Once the MHC-I positive exosomes are captured by tumor targeting antigenic (TTA) peptide and retained by immunomagnetic beads within the capture chamber with the magnetic field, the antigenic loading buffer with saturated TTA peptides will be introduced via C-Inlet to completely bind and occupy the rest available MHC-I peptide binding sites. This antigenic surface engineering process can substantially enhance the loading amount of TTA peptides to captured MHC-I positive exosomes and boost the potency to activate T-cells.

Figure 7B:
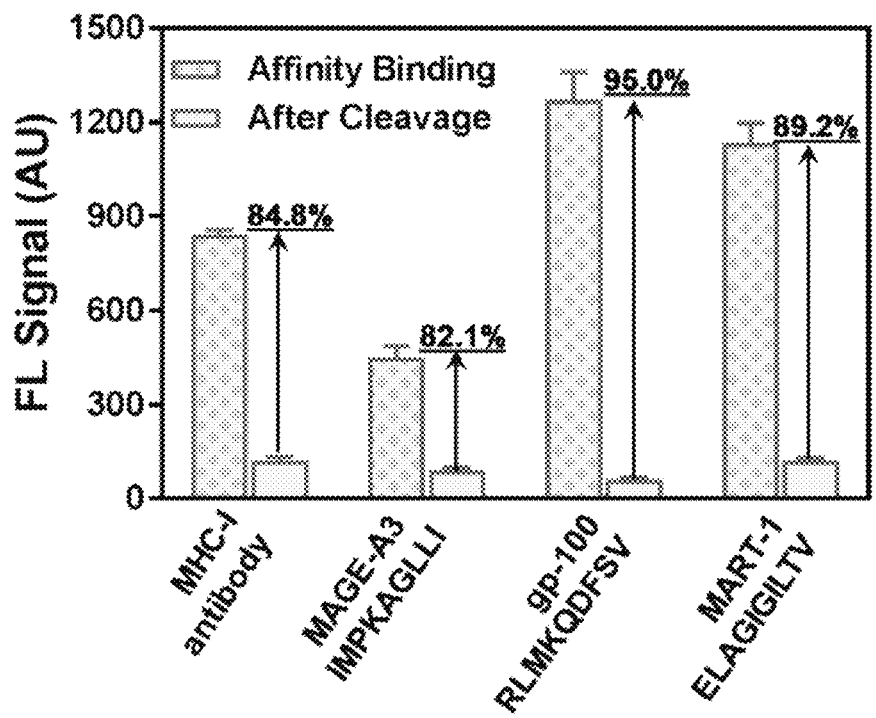
FIG. 7B shows characterization of three tumor-targeting peptide antigens conjugated with photo-cleavable immunomagnetic beads for binding and photo-release of fluorescence-labeled immunogenic exosomes. The MHC-I antibody is used as the positive control to compare the binding strength between MHC-I positive exosomes and tumor targeting peptides.
Figure 8A:
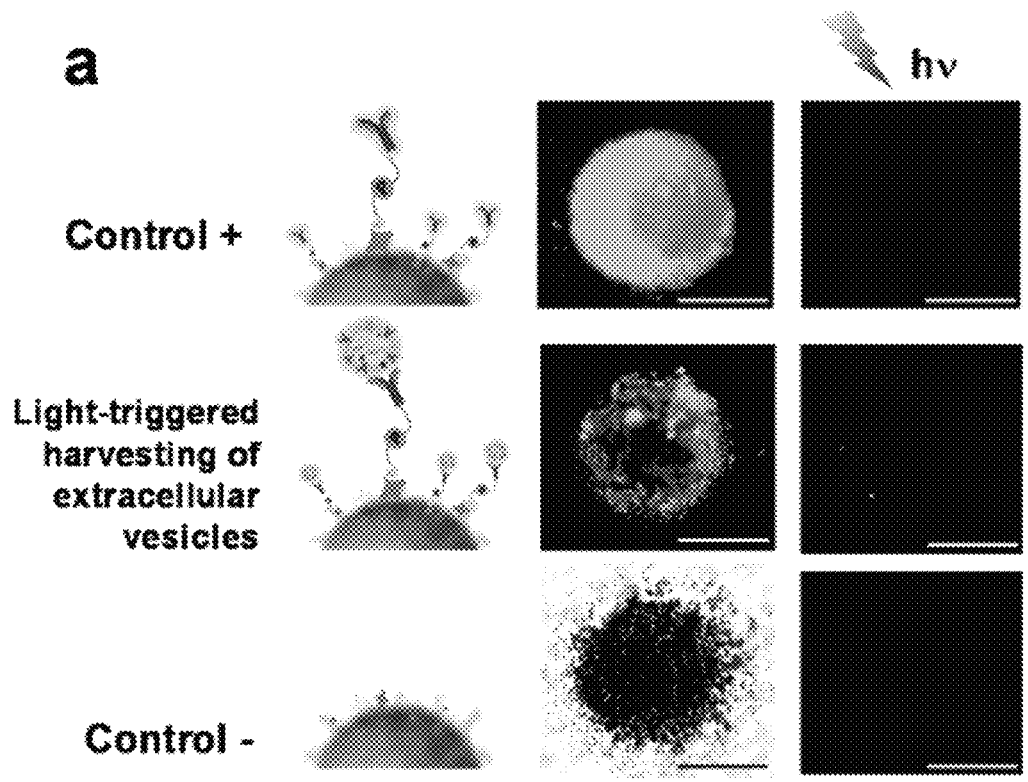
FIG. 8A show characterization of the performance of on-demand photo-release of captured exosomes from immunomagnetic capture beads. The positive control is a fluorescence-labeled antibody captured by photo-release immunomagnetic beads. The negative control is the immunomagnetic beads without a photo-cleavable linker.
Figure 8B:
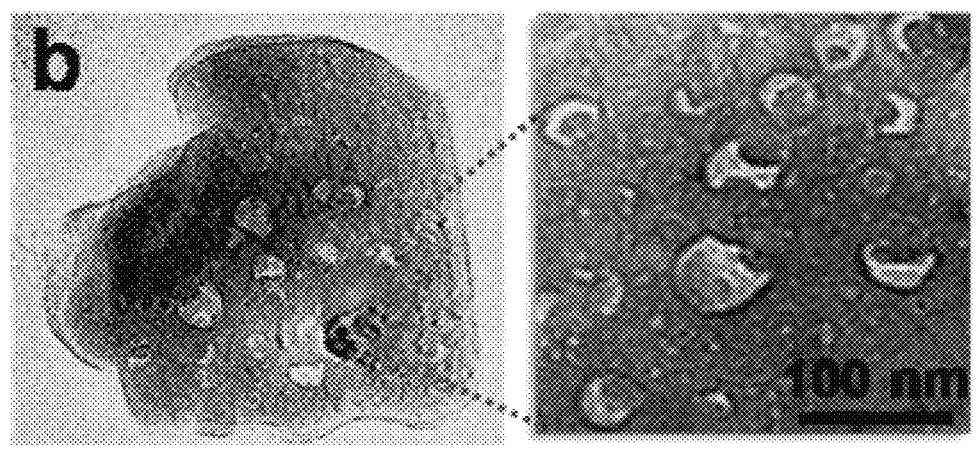
FIG. 8B shows the SEM image of a surface of photo-release immunomagnetic beads captured with exosomes. Exosome particles were seen as the cup shape due to the vacuum sample preparation.
Figure 8C:
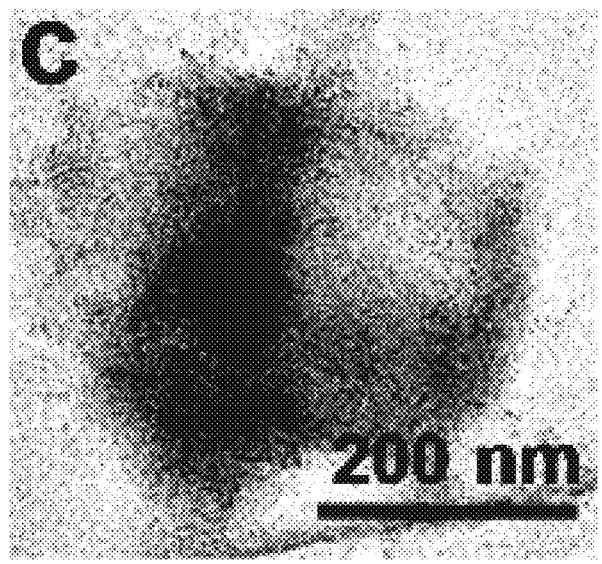
FIG. 8C shows the SEM image of the surface of photo-release immunomagnetic beads after photocleavage.
Figure 8D:
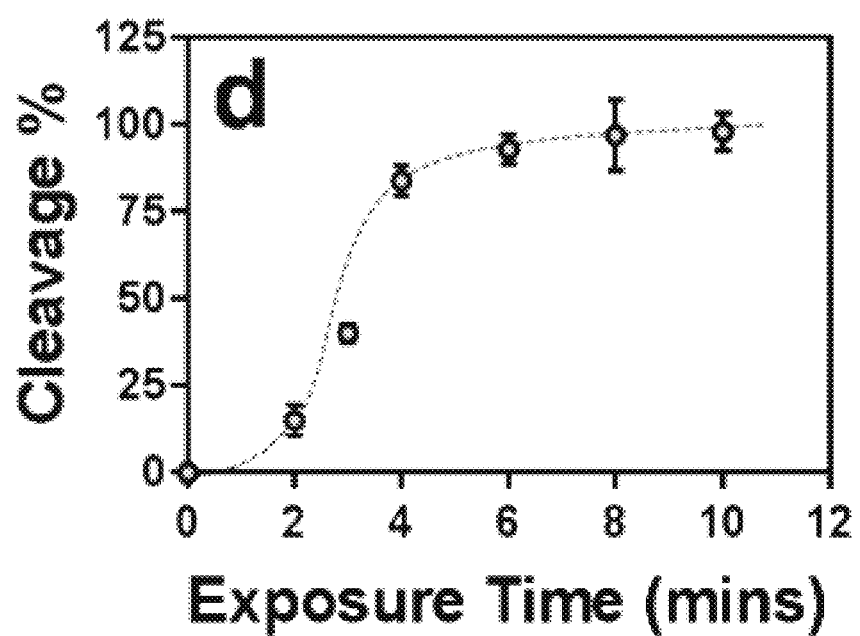
FIG. 8D shows characterization of UV exposure time influence on the photo-cleavage efficiency.
Figure 8E:
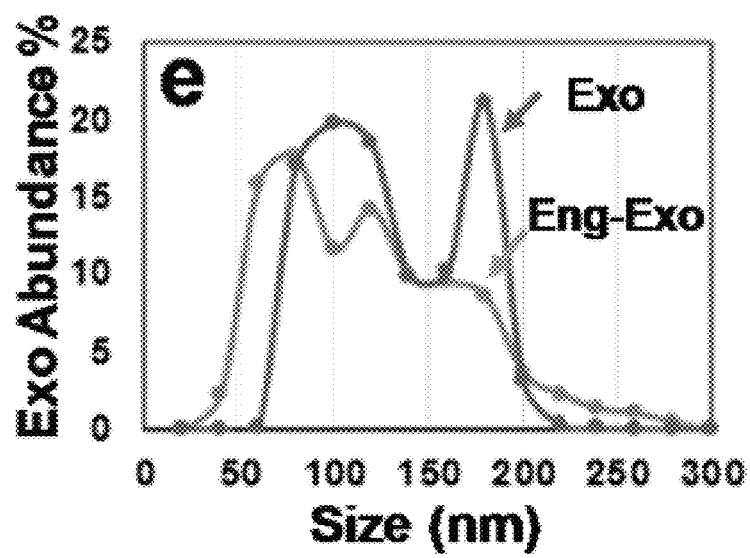
FIG. 8E shows nanoparticle tracking analysis of exosome size distribution between engineered exosomes and non-engineered exosomes.

Further characterized was the binding strength between MHC-I peptide modified photo-release immunomagnetic beads with MCH-I positives exosomes labeled with fluorescence as shown in FIG. 7B. The MHC-I antibody serves as the positive control to evaluate the binding strength between tumor targeting antigen peptides and MHC-I positive exosomes. Because of the stronger binding strength between MHC-I/peptide complex, it has a higher potential to activate T cell anti-tumor responses. gp-100 was shown to have a stronger ability to form MHC-I/peptide complex and the binding strength is even stronger than MHC-I antibody (95% vs 84.8%).

The performance of on-demand photo-release was characterized in FIGS. 8A-8E. With the comparison between positive control and negative control, the fluorescent-labeled exosomes were captured and released by measuring fluorescence intensity from beads aggregates under an invert fluorescence microscope. The SEM imaging approach was used to confirm the photo-release process. By comparing the SEM imaging of bead surface before and after photocleavage, there were no identifiable exosome particles presented on the surface of beads, indicating the good photo-release performance. The UV exposure time was characterized as well for reaching 98% photo-cleavage rate within 8-minute UV exposure. The size distribution of engineered exosomes and non-engineered exosomes was evaluated, which showed an appropriate size range of exosomes between 50 nm-200 nm, confirming that engineered exosomes are maintaining good integrity.

Figure 13:
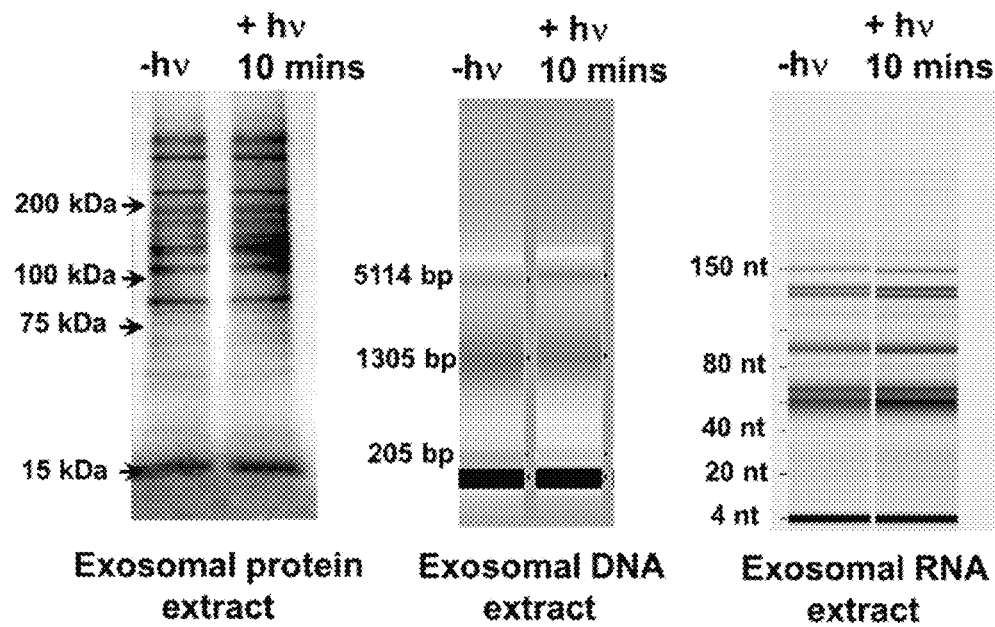
FIG. 13 shows results from investigation of the side-effect of UV exposure on exosome molecular contents in terms of proteins, DNAs and RNAs.

The side-effect of UV exposure on exosome molecular contents was investigated, which shows non-detectable changes in terms of exosomal proteins, DNAs, and RNAs under 10-minute UV treatment (FIG. 13).

Figure 9A:
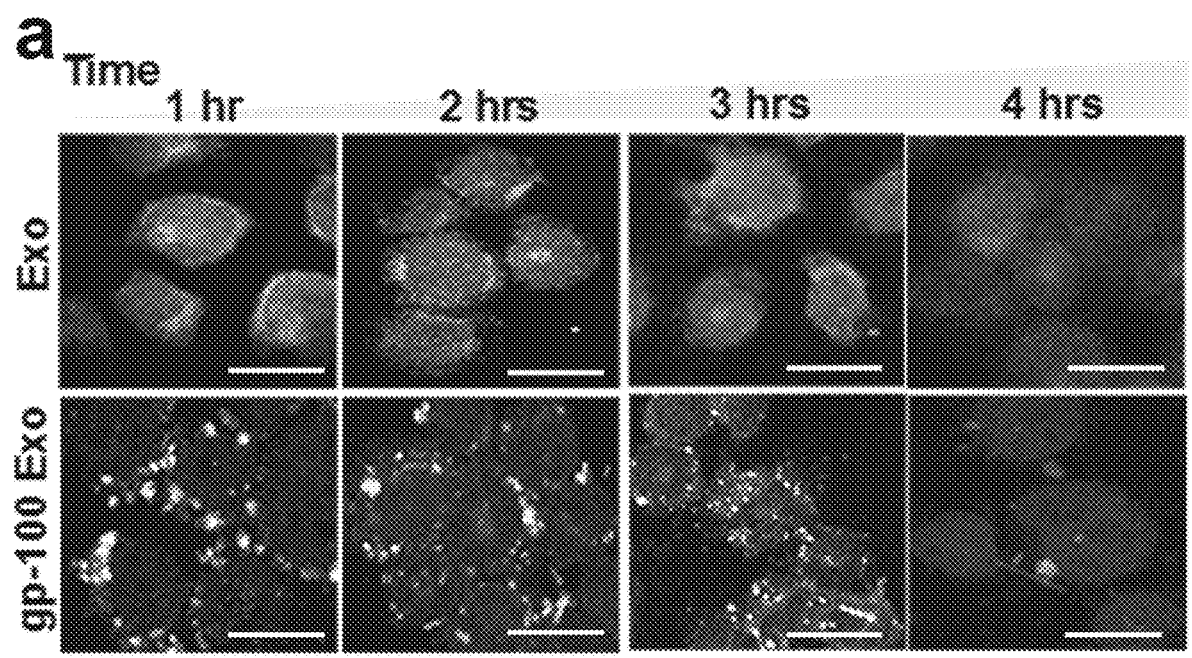
FIG. 9A shows the confocal microscope images of DC uptake of tumor targeting antigenic (TTA) peptide, gp-100 surface engineered exosomes, compared with non-engineered exosomes. The image was taken every hour for tracking the green fluorescence labeled exosomes uptake by DCs (cell nuclei were stained with DAPI).
Figure 9B:
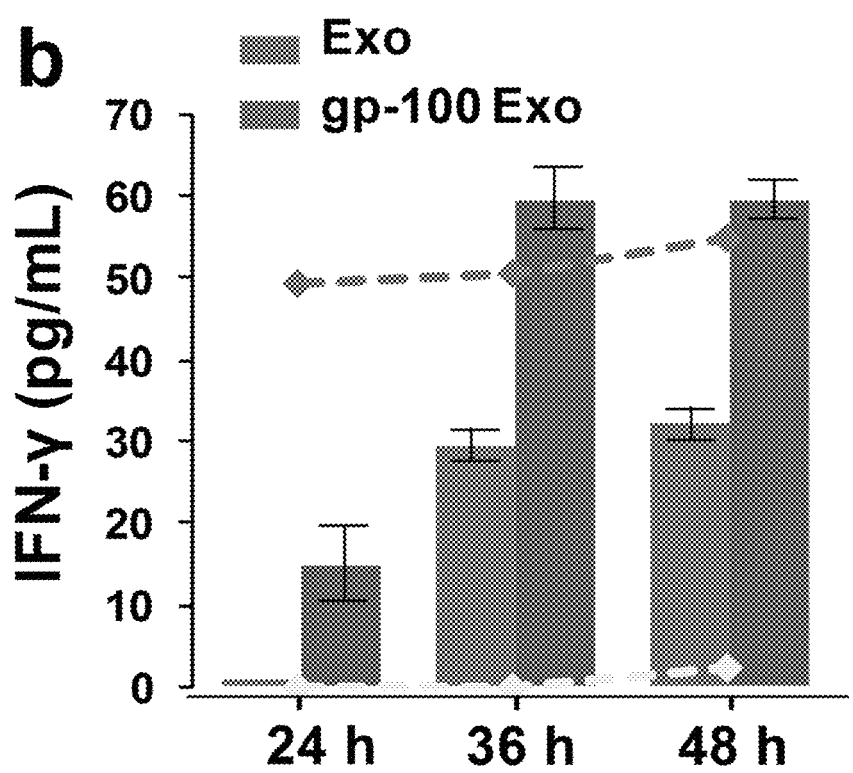
FIG. 9B shows the release of cytokine IFN-γ from DCs culture measured by ELISA for monitoring 48 hours, compared between non-engineered exosomes and gp-100 engineered exosomes.
Figure 14:
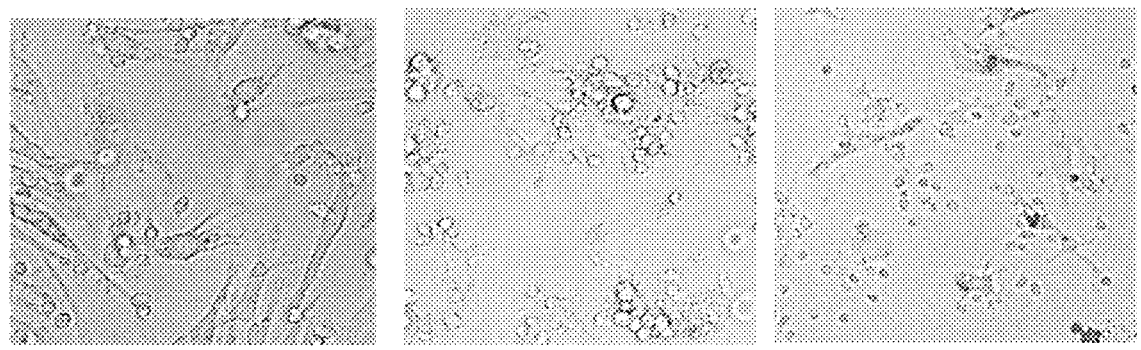
FIG. 14 shows dendritic monocytes culture under different stimulation conditions: dendritic monocytes without any stimulation (negative control; first image); PWM protein stimulation (positive control; second image); and gp-100 engineered exosome stimulation (last image).

In order to evaluate the potency and integrity of engineered exosomes released from a microfluidic cell culture device via on-demand photo-release, the exosomes from a chip outlet was harvested and labeled with green fluorescence. gp-100 engineered exosomes and non-engineered exosomes was incubated with dendritic monocytes for monitoring cellular uptake with a one-hour interval. The cells were then fixed and the nuclei were stained with DAPI. The green dots shown in FIG. 9A are labeled exosomes, which are abundantly distributed around cellular nuclei. The cellular uptake begins within one hour and the uptake speed is much faster than the non-engineered exosomes. After 4 hours, it was observed that both engineered exosomes and non-engineered exosomes were cleared by the lysosome pathway. This observation indicated that gp-100 engineered exosomes are much more active for dendritic monocytes uptake. The expression of Cytokine IFN-γ was monitored from incubating gp-100 engineered exosome with dendritic monocytes using ELISA. Compared with the incubation of non-engineered exosomes, the IFN-γ expression level was much higher for 48 hours after continuously monitoring, with a nearly 2-fold increase. The gray dash line in the FIG. 9B indicates the positive control using PWM protein as the stimulator. The dendritic cellular morphology upon stimulation was shown in FIG. 14. Compared with negative control without stimulation, the both PWM protein and gp-100 engineered exosomes gave significant influence on changing to round floating dendritic cells. The gp-100 engineered exosomes showed higher stimulation rate for Cytokine IFN-γ production than control PWM protein stimulation.

Figure 10A:
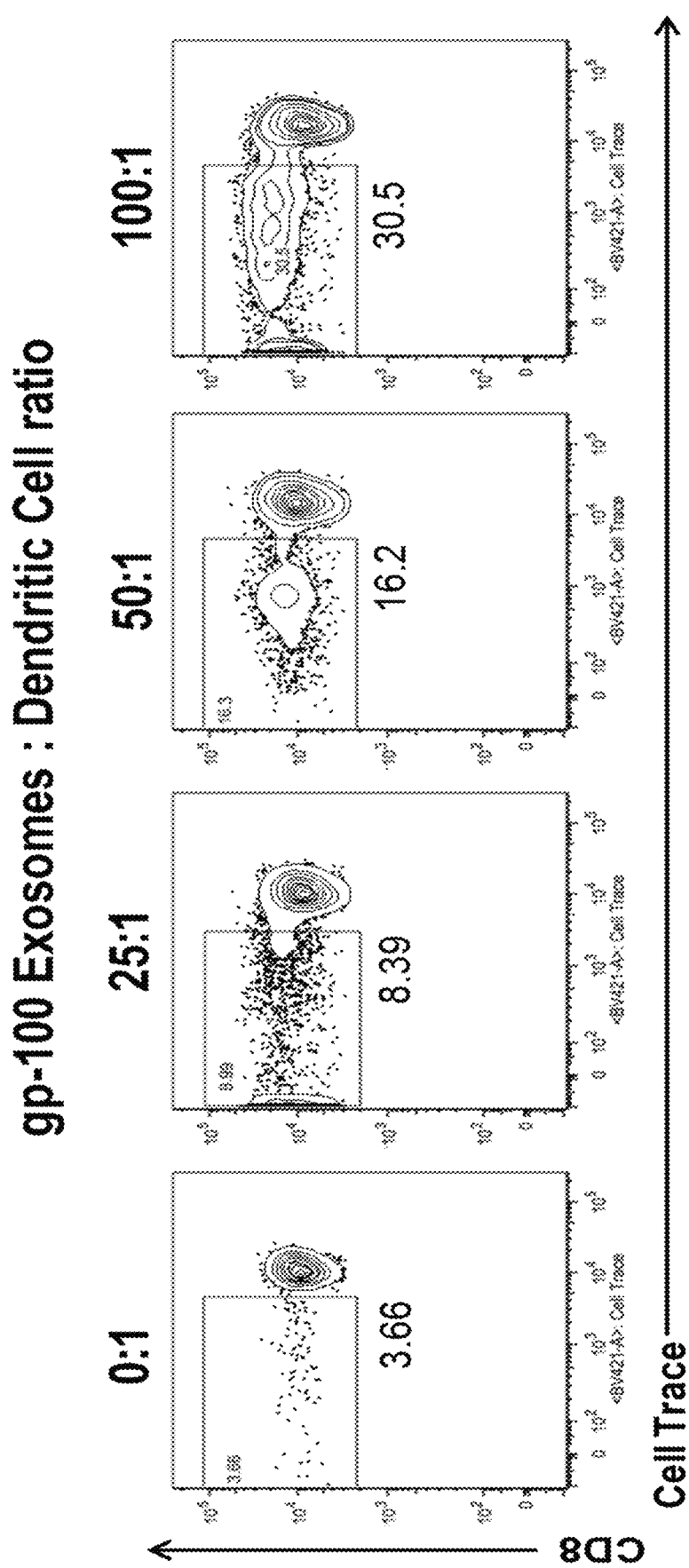
FIG. 10A depicts representative flow plots from wells containing T cells+activated JAWS cells with increasing concentrations of the gp100-engineered exosomes.
Figure 10B:
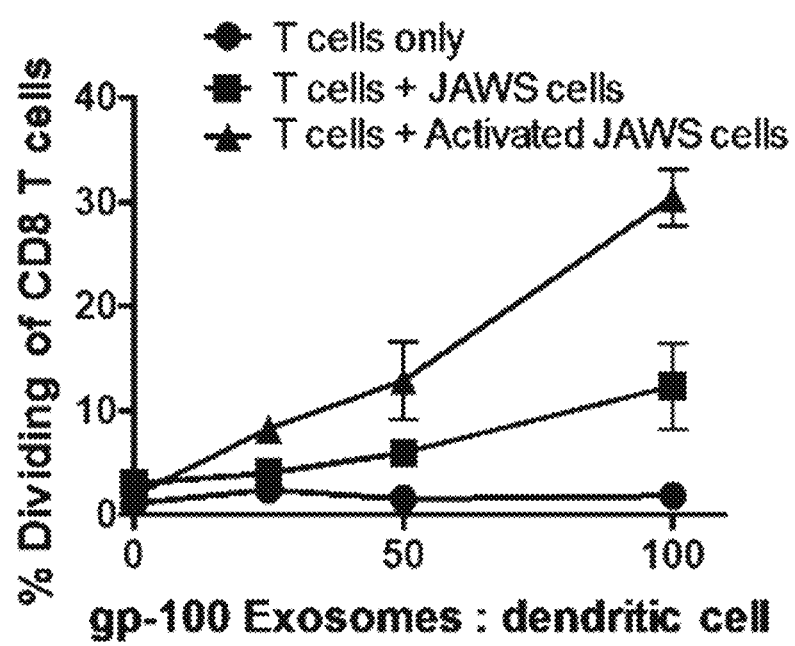
FIG. 10B depicts the cumulative data from all three culture conditions showing the CD8+ T cell dividing rate under stimulation. The results are representative of 2 independent experiments with duplicate wells for each culture condition.

Further investigated was the potency of gp-100 engineered exosome for activating CD8+ T cells undergoing proliferation and cytolysis. It was observed that gp-100 engineered exosomes have the capacity to activate transgenic T cells in the presence of activated dendritic cells. The gp100-specific CD8 T cells were purified from the spleen of 2 Pmel1 transgenic mice by magnetic cell sorting and labeled with Cell Trace Violet proliferation dye. The purified T cells were cultured alone (T cells only) and mixed at a 3:1 ratio with naïve JAWS cells (an immature dendritic cell line derived from a C57BL/6 mouse), T cells+JAWS cells, or JAWS cells that were activated for 48 hours with 200 ng/mL (T cells+Activated JAWS cells). Engineered exosomes bearing the gp100 peptide were added to the T cell cultures at increasing ratios of exosomes: dendritic cells (25, 50 and 100). FIG. 10A. The cells and exosomes were co-cultured for 5 days and then CD8 T cells were analyzed by flow cytometry for Cell Trace Violet dilution as a measure of proliferation. With T cell only condition as the negative control, it was observed that the proliferation rate of CD8+ T cells cultured with gp-100 exosomes activated JAWS showed more than 30% increase, which indicated that gp-100 engineered exosomes has strong potency to activate T cell cytolysis. FIG. 10B. The developed microfluidic on-demand antigenic surface engineering and photo-release of exosomes could be a powerful tool for developing an effective exosome-based vaccine and delivery system for advancing Cancer Immunotherapy.

Immunogenic potency was also investigated for bovine respiratory syncytial virus (BRSV). T cells and activated JAWS cells were incubated with increasing concentrations of BRSV antimicrobial peptide-engineered exosomes (exosomes engineered with Peptide 4: M187-195 peptide NAIT-NAKII, SEQ ID NO:4). The immune-stimulation of CD8+ T cell proliferation is linearly responded to the dose of engineered exosomes which is more effective than using high dose peptide vaccines. The BRSV engineered exosomes have the capacity to activate BRSV M-specific T cells in the presence of activated dendritic cells. C57BL/6 mice were immunized twice subcutaneously with 20 nM BRSV M187-196 adjuvanted in QuilA. At least 4 weeks after the final immunization, the animals were euthanized and spleens were collected. CD8+ T cells and CD11c+ splenic dendritic cells were isolated by magnetic cell separation. CD8+ T cells were labeled with Cell Trace Violet proliferation dye. The purified T cells were cultured alone (T cells only), or were mixed at a 3:1 ratio with CD11c+ splenic DC (T cells+DC).

Figure 11:
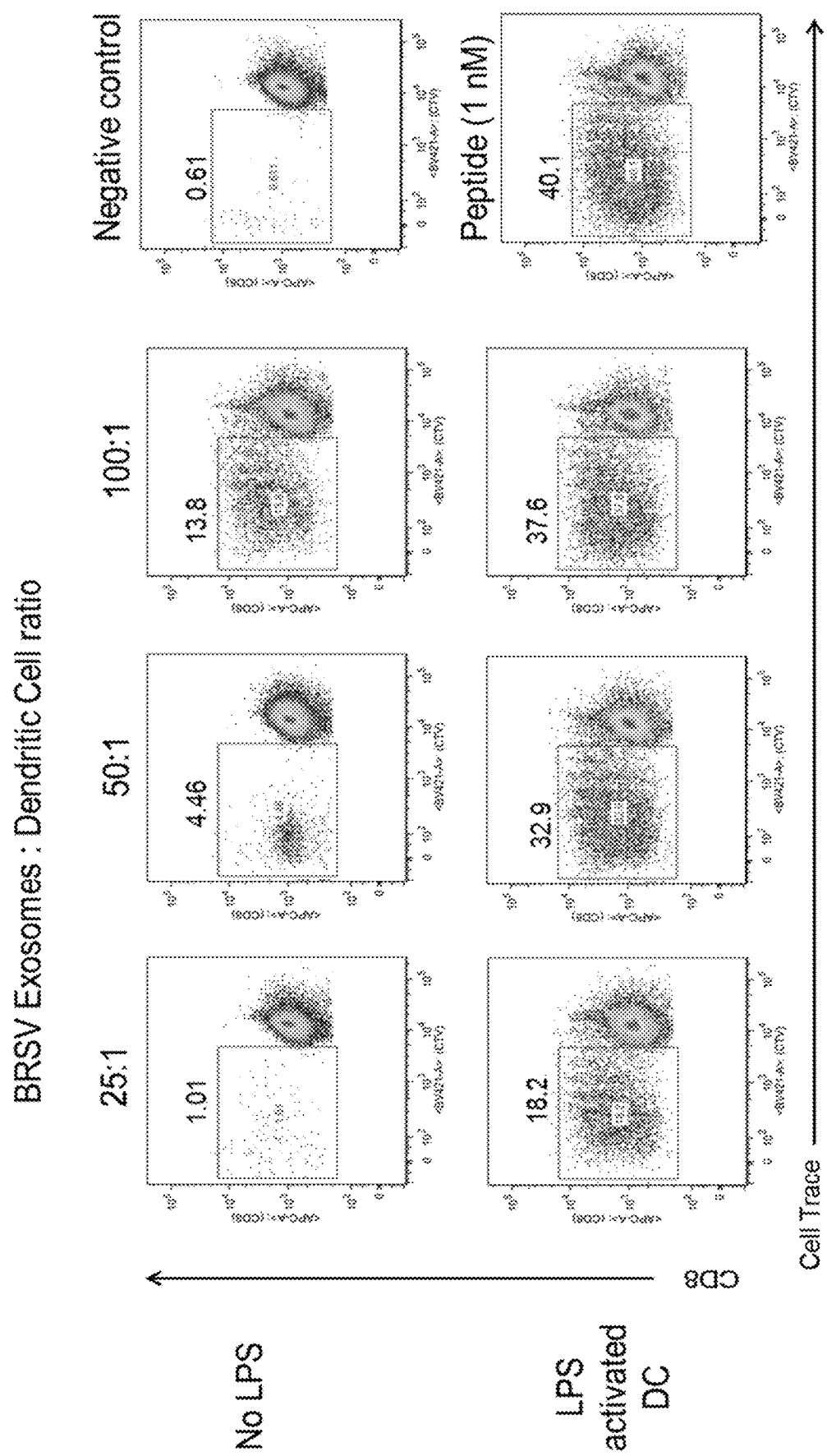
FIG. 11 depicts flow cytometry plots from wells containing T cells and activated JAWS cells with increasing concentrations of the bovine respiratory syncytial virus (BRSV) antimicrobial peptide-engineered exosomes for depicting the immunogenic potency.
Figure 12A:
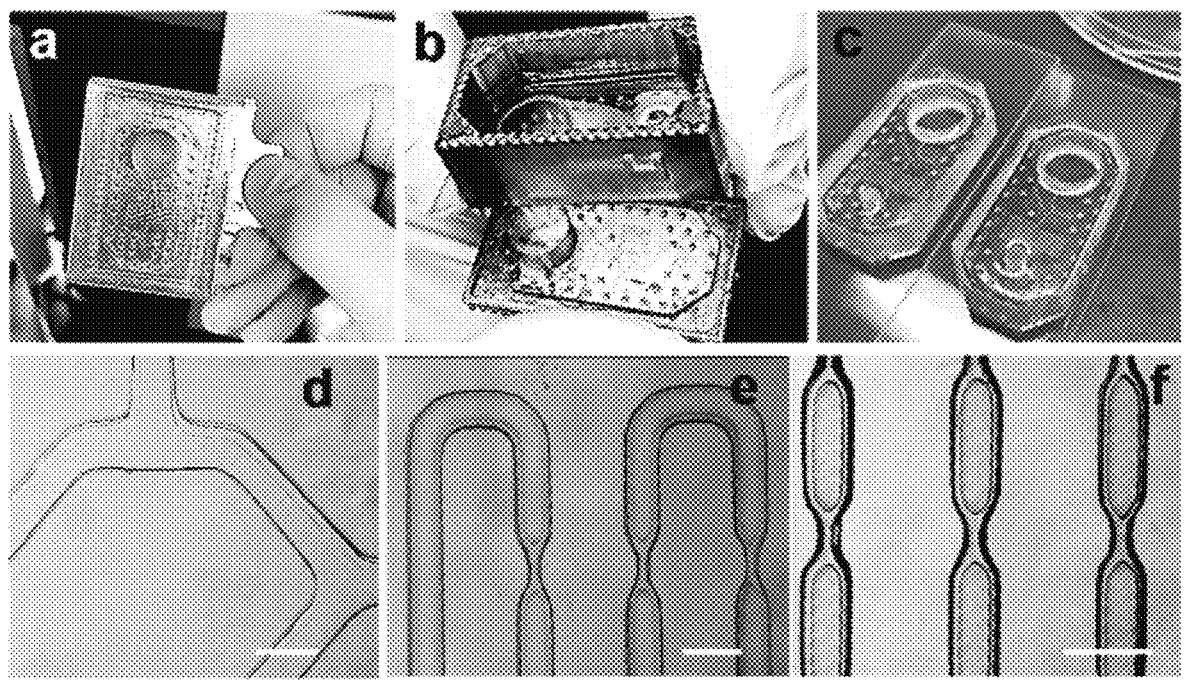
FIG. 12A illustrates a 3D printing approach for producing 3D mold integrated with cell culture and downstream exosome isolation, surface engineering, and on-demand photo release.
Figure 12B:
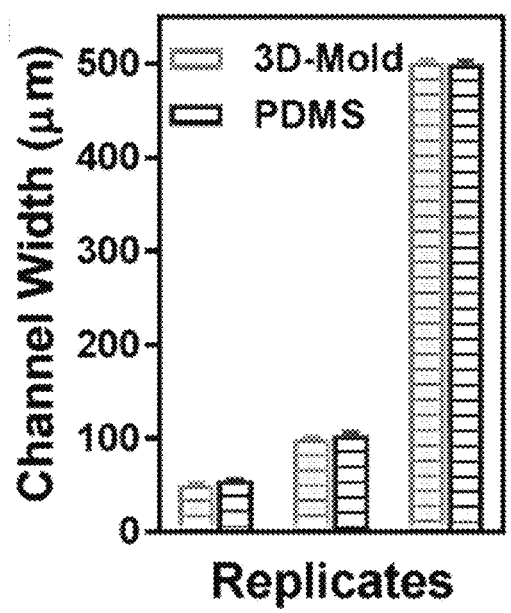
FIG. 12B shows the results from replicating PDMS microfluidic device.

DC cells were left unstimulated or were treated with 200 ng/mL LPS to induce DC activation. Engineered exosomes loaded with the BRSV peptide using the above-described microfluidic platform were added to the T cell cultures at increasing ratios of exosomes: dendritic cells (25, 50 and 100). Negative control wells did not receive exosomes. Positive control wells were treated with 1 nM or 5 nM pure M187-196 peptide. The cells and exosomes were co-cultured for 5 days and then CD8 T cells were analyzed by flow cytometry for Cell Trace Violet dilution as a measure of proliferation. The results are shown in FIG. 11. All results support that the disclosed method for capture, antigenic loading, and photo-release can effectively produce antimicrobial peptide engineered exosomes which lead to successful activation of T cells with high potency.

Example 2: In Vivo Administration of Engineered Exosomes

The above immunogenic potency study used transgenic mice which were injected with engineered exosomes using proprietary disclosed method. The exosomes were engineered with gp-100 or BRSV M187-196 peptide on the surface using the above-described streamlined/continuous microfluidic process, and suspended in the PBS buffer for in vivo Intraperitoneal injection through tail. We observed no injection site reactions or adverse responses (injection site swelling, irritation, etc.) from the injected mice. Mice were observed twice per day for the first 72 hours after the injections and no adverse reactions were noted, indicating general in vivo safety of the engineered exosomes and related compositions.

Example 3: Nanographene Fabricated Nano Pom Poms for Robust Preparation of Small Extracellular Vesicles Assisting Precision Cancer Diagnosis and Therapeutics Extracellular vesicles (EVs), particularly exosomes, are emerging in developing liquid biopsy diagnosis of cancer, as well as the therapeutic delivery. However, due to heterogeneous populations from diverse cell types, obtaining pure extracellular vesicles (EVs) that are specific to their cellular origin and molecular information is still extraordinary challenging, which substantially hindered the clinical utility. Herein, we introduced a novel 3D-structured nanographene immunomagnetic bead with unique Nano "pom poms" (aka NanoPoms) morphology for specific marker-defined capture and release of intact small EV (sEV) subpopulations from nearly all types of biological fluids, including human blood, urine, cow's milk, and cell culture medium, etc. The conjugated photo-click chemistry on bead surface enables the release of intact, captured sEVs on demand for ensuring substantially enhanced diagnostic specificity and sensitivity employed in non-invasive diagnosis of bladder cancer, as demonstrated by multi-omic analysis using the next generation sequencing (NGS) of somatic DNA mutations, miRNA profiles, as well as the Western blotting and global proteomic analysis. The Nanopoms prepared sEVs also showed distinctive in vivo biodistribution patterns specific to their subtypes with good biological activity. Such superior purity with improved specificity for pathogenic EV subpopulations will provide a precision approach critically needed in developing EV-based precision cancer diagnosis and therapeutics.

Developing the diagnostic and therapeutic utility of EVs is emerging, which promoted tremendous progress in cancer diagnosis, regenerative tissue repair, immunotherapy, drug delivery, and gene therapy. EVs are living cell-secreted membrane vesicles in multiple subpopulations, including membrane shedding microvesicles (100 nm-1000 nm), endosomal multivesicular body released exosomes (30 nm-150 nm), and apoptotic cellular fragment vesicles (≥1000 nm). Due to such large heterogeneity and significant size overlap between vesicle populations, the consensus has not yet emerged on precisely defining EV subtypes, such as endosome derived exosomes which is highly relevant to the disease pathogenesis. Assigning EVs to a particular biogenesis pathway remains extraordinarily challenging. The generic term of EVs is recommended by complying with 2018 guidelines from the International Society for Extracellular Vesicles (ISEV) proposed Minimal Information for Studies of Extracellular Vesicles ("MISEV"). However, significant attention has been focused on the exosome type small EVs (sEVs) and their molecular components (e.g., proteins, DNAs, mRNA and miRNA), which implicates a variety of physiological functions and pathological disease states. sEV secretion is exacerbated in tumor cells and enriched with a group of tumor markers, as evidenced by increased presence in plasma and ascites patients in variable cancers. However, currently there is no standardized purification method for obtaining pure sEV populations that are specific to their cellular origin and molecular information yet. The purification methods that recover the highest amount of extracellular materials, no matter with the vesicle or non-vesicular molecules, are mainly the precipitation polymer kits and lengthy ultracentrifugation-based (UC) approach. Such isolation approach is unable to differentiate the sEV populations from different cellular origin or other EV subtypes (e.g., microvesicles and apoptotic bodies), as well as free proteins. This is a significant concern particularly for studying the tumor cells derived circulating sEVs. The bulk measurement of a mixture of vesicle populations could potentially mask the essential biosignatures, which severely impairs the development of cancer diagnosis and the investigation of pathological mechanism. Moreover, the current existing isolation methods are rather in low efficiency (e.g., UC isolation at ~5-25%) and involves multiple time-consuming manual steps which is not scalable, yet unable to separate exosome sEVs from virus. Therefore, methods for recovering exosome-type sEVs without non-vesicular components are urgently needed, although the recovery could be less than total EVs.

Figure 15A:
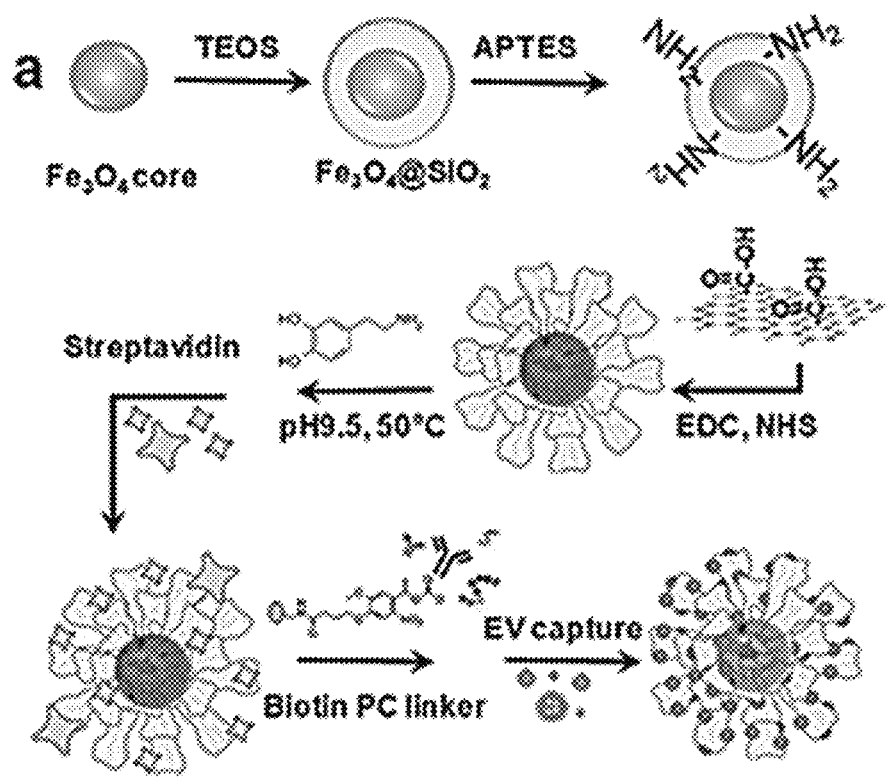
FIG. 15A is a schematic illustration of the fabrication of Nano Pom Poms immunomagnetic particles.
Figure 15B:
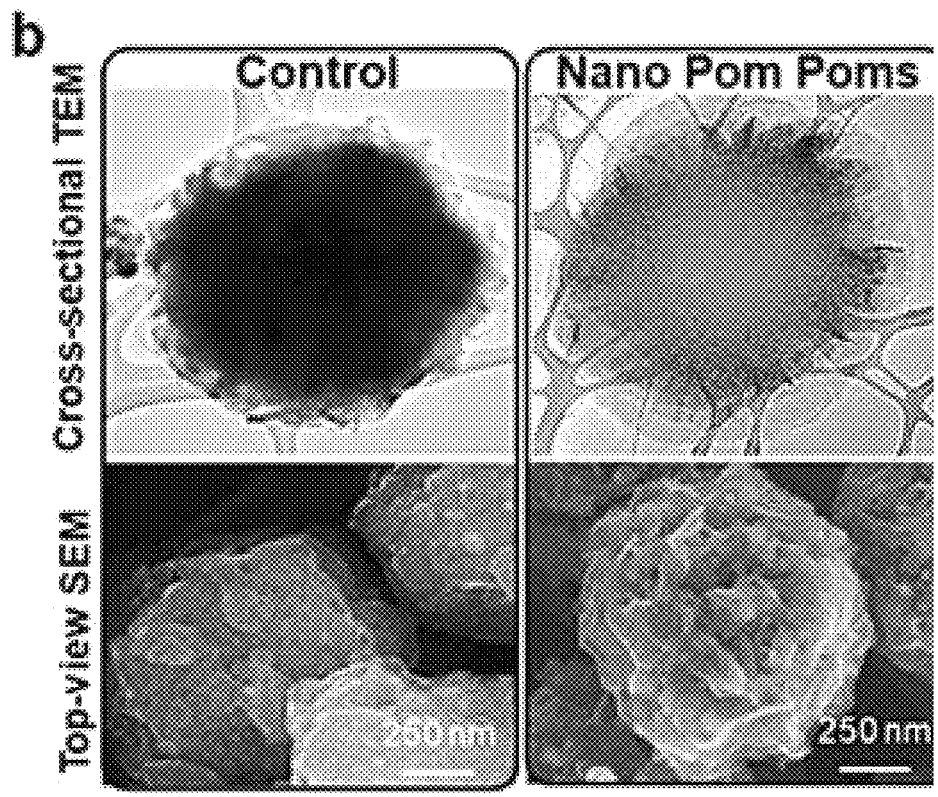
FIG. 15B shows TEM (top) and SEM (bottom) images showing the unique 3D nano-scale pom poms-like morphology from fabricated NanoPoms immunomagnetic particles (right panel) compared to commercial immunomagnetic beads (left panel).
Figure 15C:
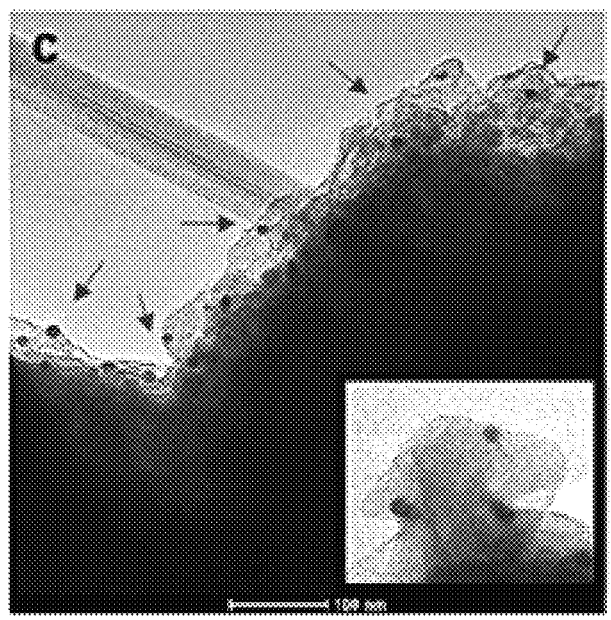
FIG. 15C shows TEM imaging of the surface of Nano-Poms captured with sEVs validated by antiCD63 gold nanoparticle immunestaining. The insert shows the captured single EV in the size range of ~100 nm with three gold nanoparticles bound (~10 nm).
Figure 15D:
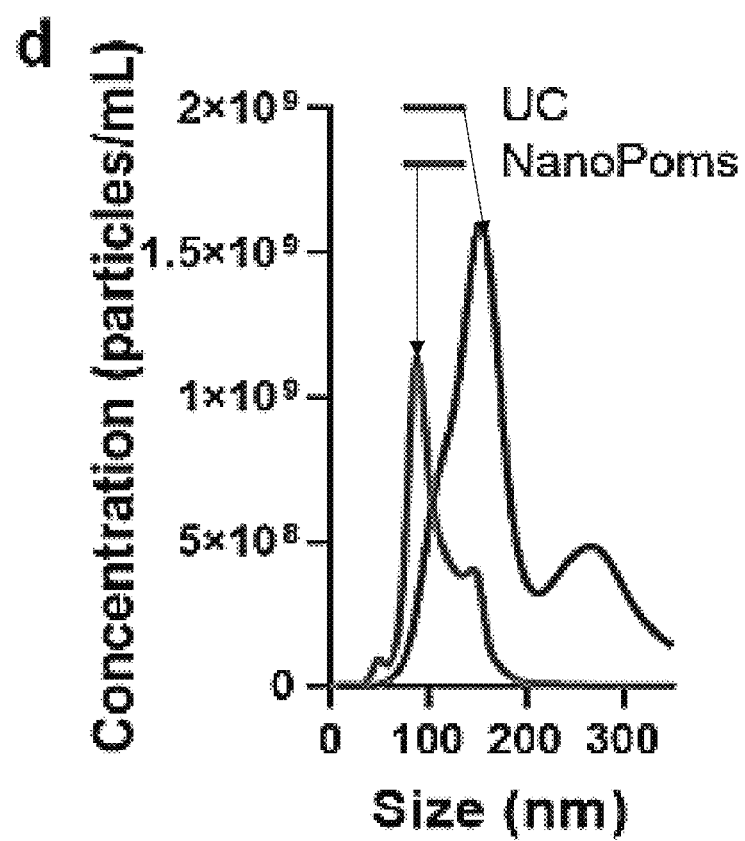
FIG. 15D is a graph of the NTA analysis of NanoPoms isolated sEVs in comparison with UC isolated EVs.
Figure 15E:
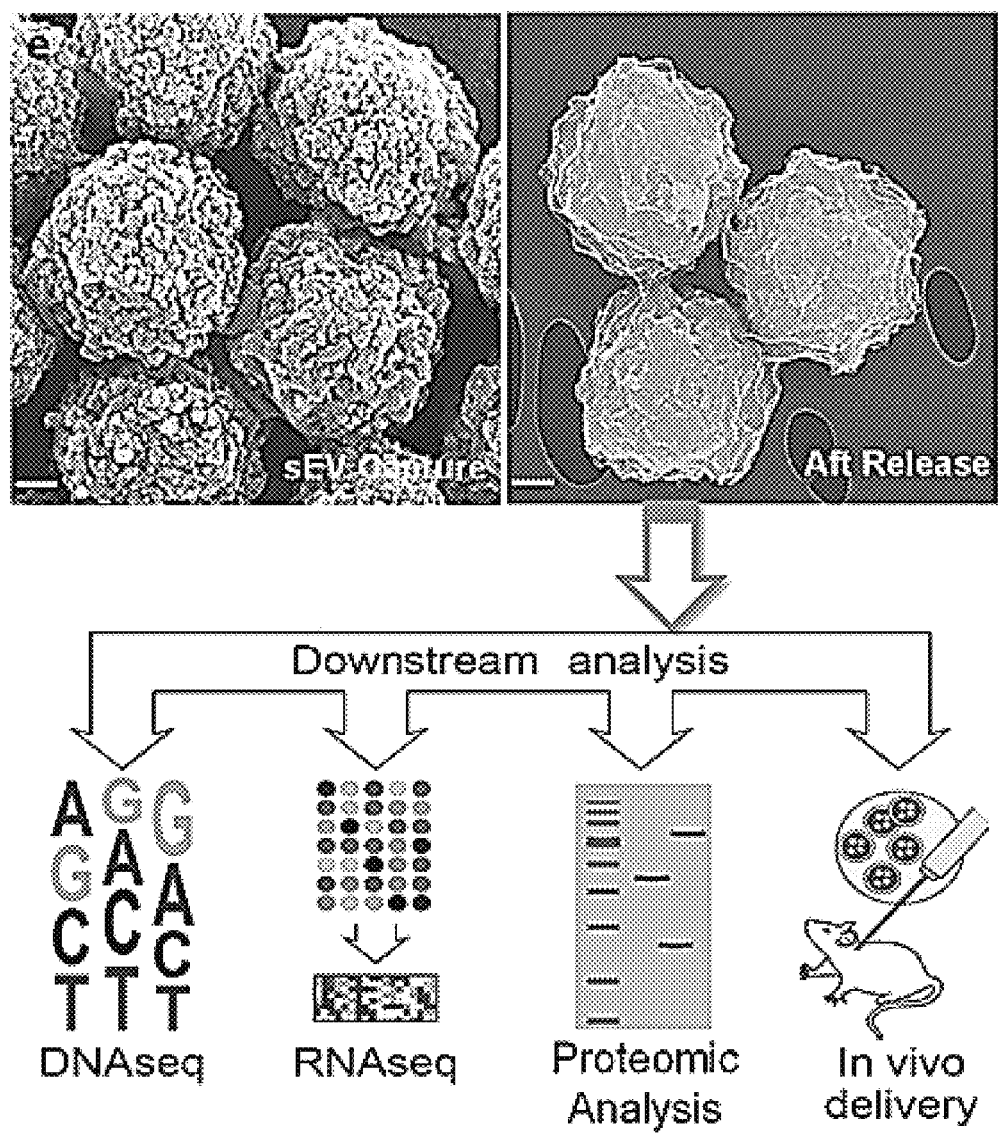
FIG. 15E shows SEM imaging of captured sEVs which are completely covering NanoPoms immunomagnetic particles, and are completely released from NanoPoms particles after photorelease. The scale bar is 100 nm. The photoreleased sEVs can be collected on-demand for downstream applications including DNA NGS, small RNA NGS, western blotting and proteomic analysis, as well as the in vivo delivery.
Figure 16A:
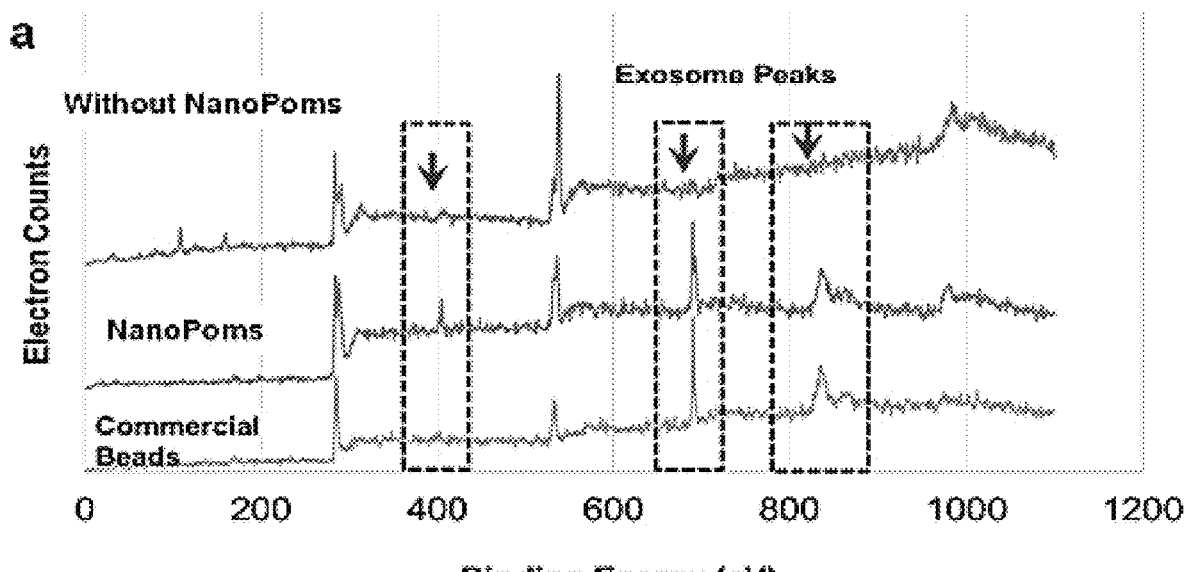
FIG. 16A is a graph from X-Ray Photoelectron Spectroscopy (XPS) analysis of NanoPoms immunomagnetic particle surface properties with extracellular vesicles captured. The immunomagnetic particles without the 3D-structured nanographene serves as the negative control. The commercial dynabeads were used as the positive control.

Immunomagnetic capture for isolating specific EV populations has been well accepted, due to the simple and straightforward protocols and specificity to their significant molecular markers. However, current existing particle capture approaches are either in small quality with manual protocols, or bound to solid surface/particles, and unable to release intact, pure EV subpopulations. In this work, we introduce novel immunomagnetic particles featured with the unique 3D hydrophilic, nanostructured graphene-sheet layers (Nano pom poms) which is capable of on-demand photo release of intact EV subpopulations from capture particles (FIG. 15A-E). Nano-graphene is an emerging interface to enhance biorecognition and bioseparation owing to its rich surface chemistry, large surface area, and small feature sizes comparable to EVs. Conventionally, the non-covalently assembled nano-graphene coating suffers from the instability in buffer solutions over time. Our method interfaces $Fe_3O_4/SiO_2$ core-shell particles (~1 μm) with graphene nanosheets via carboxamide covalent bonds, which leads to substantially improved stability in the aqueous sample solution (FIG. 16). The pom poms-like graphene nanosheets aggregate on particle surface, which produces the unique 3D nano-scale cavities in between for affinity capture of only nano-sized vesicles (FIG. 15A-E and FIG. 16). Most importantly, the conjugated photo-click chemistry on particle surface allows the release of intact, captured sEVs on demand, which further ensures the specificity for harvesting marker-defined sEV subpopulations. Herein, we demonstrated the substantially improved specificity for isolating tumor cell derived circulating sEVs from bladder cancer patient urines, without any additional purification steps.

The urological tumors make up approximately 25% of all human cancers, and their recurrence and progression rate are ~50-70% which is higher than other tumors. Thus, the most bladder cancer patients require lifelong monitoring of recurrence, and demand heavily on non-invasive diagnostic or prognostic tools for long-term follow-up. Current gold standard diagnostic procedures for bladder cancer are cystoscopy and urinary cytology which are invasive and low sensitivity to small papillary or Cis tumors, and also frequently cause side effects such as dysuria, hematuria, or urinary tract infection. Urine EVs have become a valuable and promising source of biomarkers for urological tumor detection. Additionally, the group of enriched biomarkers carried by urine EVs offers the unmatched possibility to integrate multi-omic data analysis for precisely defining the onset and progression of the bladder cancer disease. In this paper, we used our developed NanoPoms immunomagnetic particles to specifically isolate sEVs from bladder cancer patient urines, and analyzed the EV DNA mutations, microRNA profiles, as well as the protein biomarkers and proteomic profiles that are relevant to urological tumors. The results showed much higher specificity and sensitivity for detecting urological tumor biomarkers from NanoPoms isolated sEVs compared to other ultracentrifugation or beads-based isolation approaches, which is highly desired for developing liquid biopsy analysis of bladder cancer. We also tested the NanoPoms prepared intact EVs for in vivo biodistribution and assessed their biological activity, which showed viable biological property in vivo with distinctive subpopulation specificity. The in vivo study using Nano Pom Poms prepared sEVs supports the potential for developing as a precision drug delivery carrier.

Results

Figure 17:
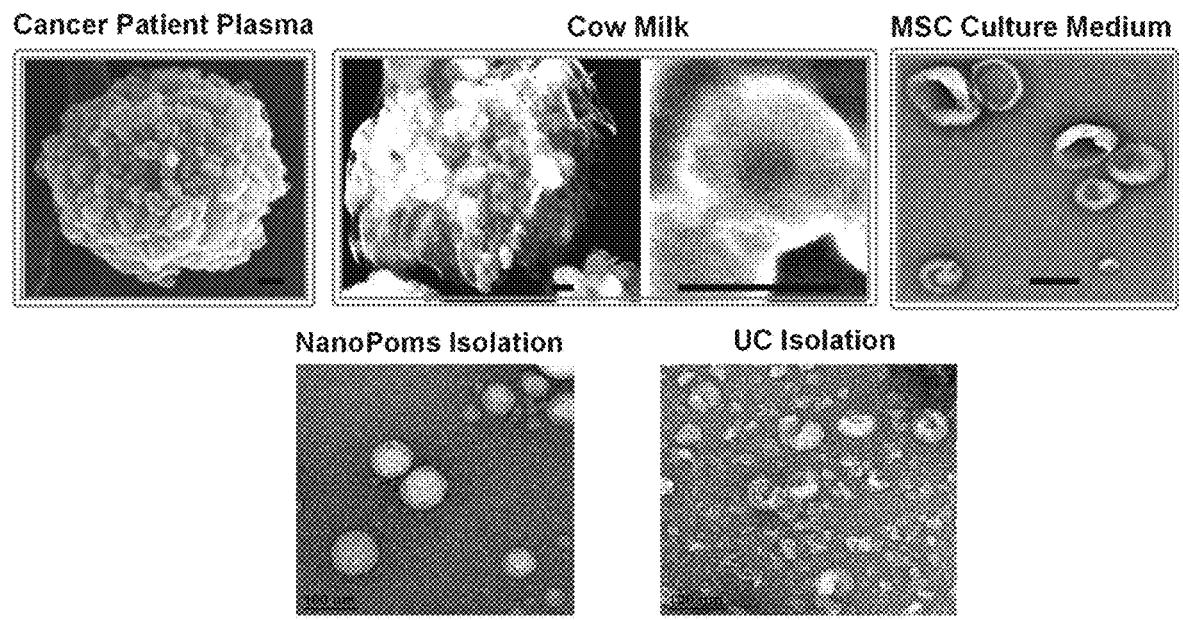
FIG. 17 shows SEM and TEM images (top row) showing the morphology of NanoPoms particle captured sEVs from a variety of biological fluids: sEVs captured from ovarian cancer patient plasma (left), sEVs captured from the cow's milk with enlarged insert showing the classic cup shape (middle), sEVs captured and released from the Wharton's jelly mesenchymal stem cell culture medium (right). The scale bar indicates the 100 nm; and TEM images (bottom row) showing the much clean and uniform sEVs prepared from NanoPoms isolation from cell culture medium. In contrast, ultracentrifugation isolation prepares EVs in a mixture with small aggregates and debris.
Figure 18:
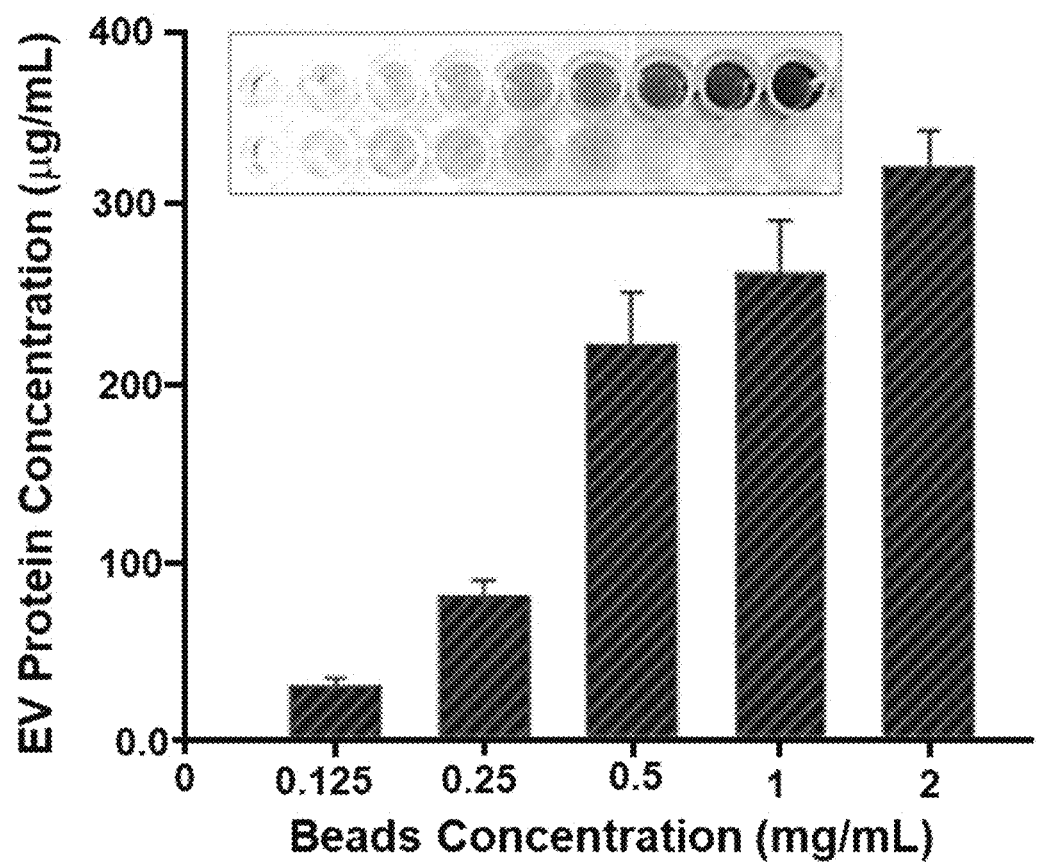
FIG. 18 shows a graph and corresponding photographic image from the optimization of NanoPoms particles concentration used for isolating sEVs from 1 mL milk solution, characterized by the Pierce BCA Protein Assay. The five repetitive measurements were performed for each data point with RSD<~5% (n=5).

NanoPoms immunomagnetic particles enable specific capture and on-demand release of intact sEV subpopulations. Compared to other EV isolation approaches, immunomagnetic beads can specifically define EV subpopulations based on their surface markers, in turn, lead to a better purity to exosome type sEVs, which is highly desirable to harvest disease pathogenesis relevant EV subpopulations in cancer liquid biopsy and early detection. The synthesis route and unique 3D nano-scale pom poms structure were shown in FIG. 15A-B. Much larger hydrophilic surface areas are available with unique pom poms morphology for immobilization of higher density of affinity capture entities (e.g., antibodies, aptamers, and affinity peptides), in contrast to commercial Dyna beads (FIG. 15B right panel vs. left panel). FIGS. 15C and E showed both TEM and SEM images on capturing nano-sized EVs from bladder cancer patient urines, which indicates the dense, round-shaped, nano-sized EVs (~100 nm) completely covering the particle surface and are completely released and separated from particles after photorelease. The X-Ray Photoelectron Spectroscopy (XPS) analysis of surface chemistry, SEM imaging of particles before capture and after release, as well as the fluorescent binding analysis were also performed to evaluate sEV capture performance and capacity (FIG. 16). More biological fluids including cancer patient plasma, cell culture medium from mesenchymal stem cells, and cow milks were also used to validate NanoPoms EV preparation approach as a generic and robust sEV isolation platform (FIG. 17 and FIG. 18). This operation protocol is also much simple and cost-effective, amenable for scaling up, sterilization settings, and GMP operations (see Table s1).

Figure 16B:
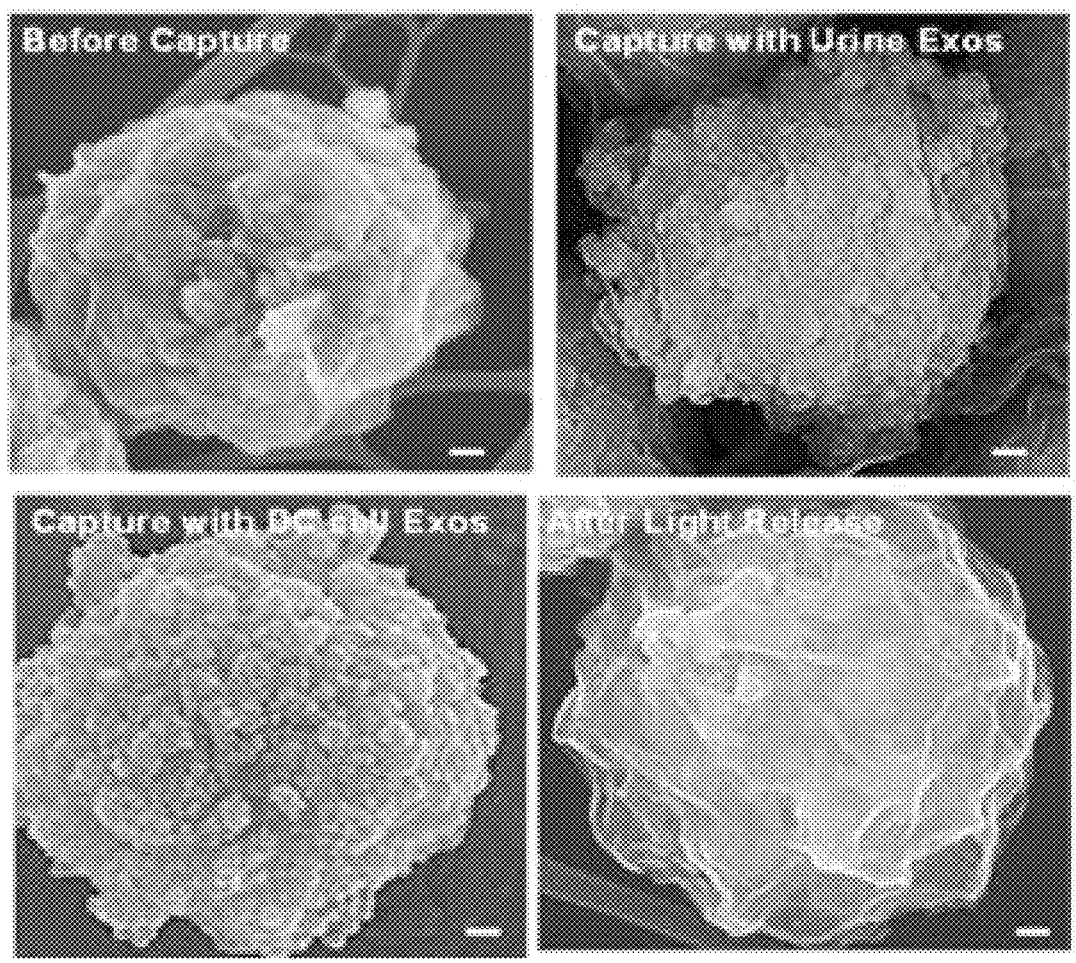
FIG. 16B shows SEM images showing the surface morphology of NanoPoms particles before EV capture, after EV capture, and after release of captured EVs. The scale bar is 100 nm. The dense round small particles were seen covering NanoPoms particle surface completely after capture and can be completely release from particles for harvesting intact sEVs.
Figure 16C:
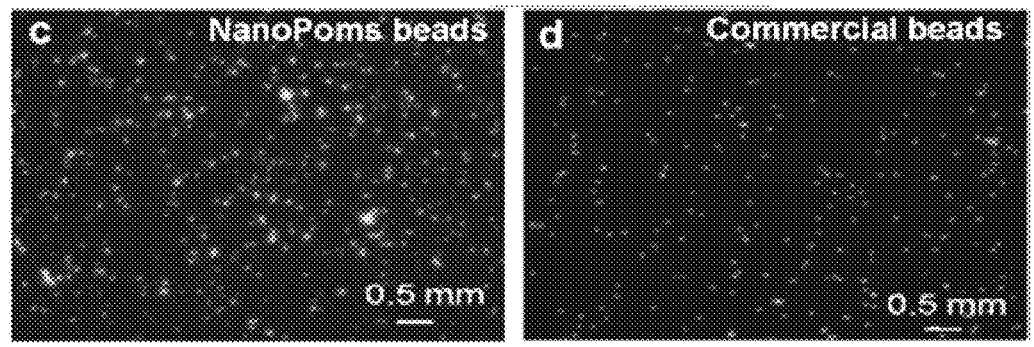
FIG. 16C shows fluorescence microscopic images showing the NanoPoms particles bound to FITC-biotin after conjugation with streptavidin, with dyna streptavidin beads as the positive control, which exhibits the much brighter fluorescence from NanoPoms particles indicating more binding sites.

The conjugated photo-click chemistry on the surface of NanoPoms immunomagnetic particles enables the on-demand, light triggered release of captured sEVs (FIG. 15 and FIG. 16B). The released sEVs purified from bladder cancer patient urines were characterized using nanoparticle tracking analysis (NTA) in comparison to UC isolation (FIG. 15E). Much narrower size range around 100 nm is observed, while UC isolated EVs are in the size range from 150 nm-400 nm. Although the total sEV number is less than UC isolated EVs, we hypothesize that NanoPoms particles isolated sEVs could be more specific and purer to their cellular origin and molecular information. In order to prove such isolation specificity and purity, we further characterized the exosomal molecular contents using the next generation sequencing (NGS) for identifying somatic DNA mutations and miRNA profiles, as well as the western blotting and global proteomic analysis of tumor protein markers.

NGS Analysis of Tumor-Specific DNA Mutations Carried by Urinary EVs.

Figure 19A:
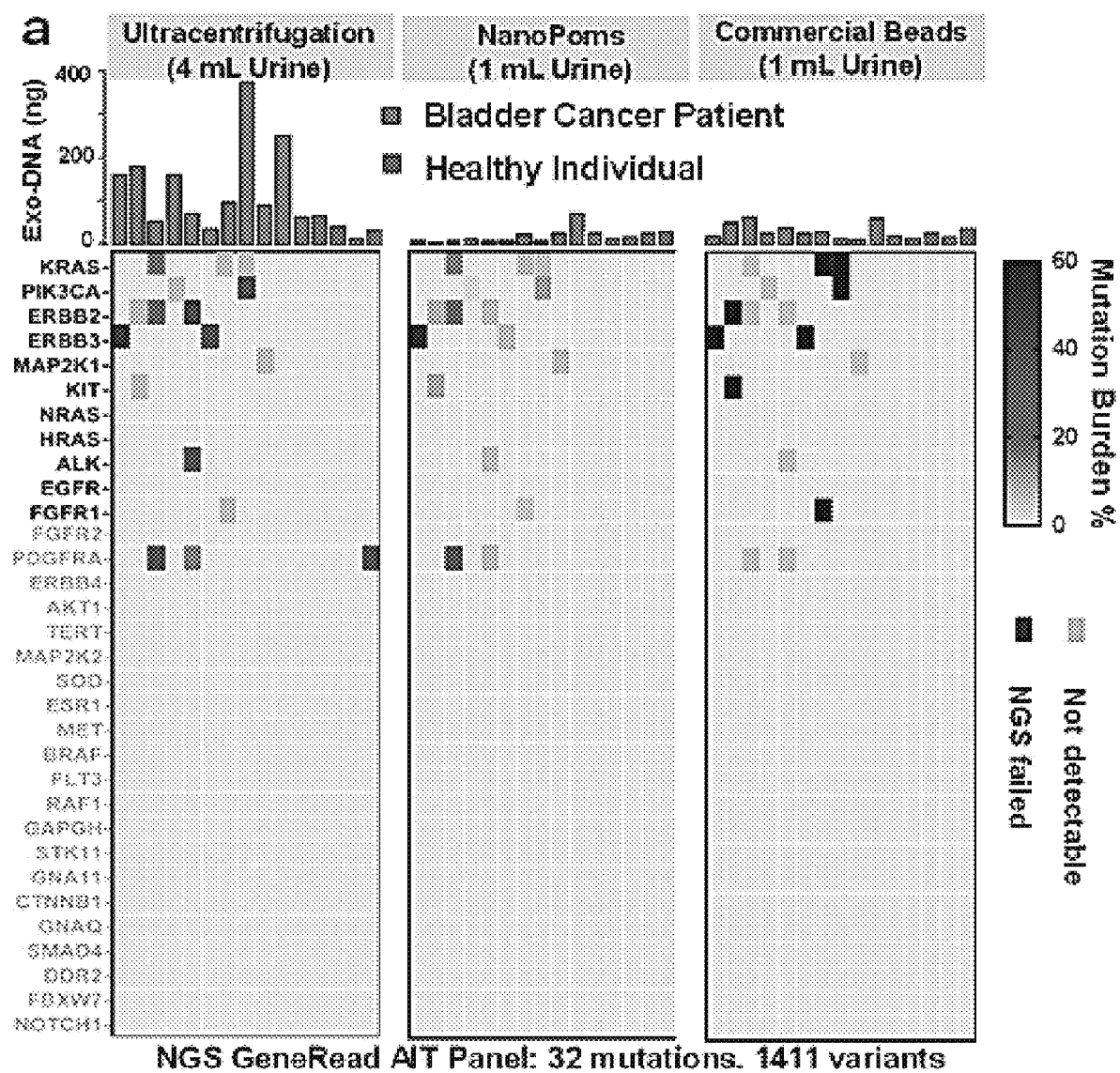
FIG. 19A shows results from DNA NGS analysis of 11 BC patient urine samples with 4 healthy individuals as the control group using GeneRead AIT panel. The EVs were prepared in parallel by UC, NanoPoms, and control bead approaches to extract total DNAs shown in the bar graphs. The most frequent 1,411 cancer relevant variants were sequenced.
Figure 19B:
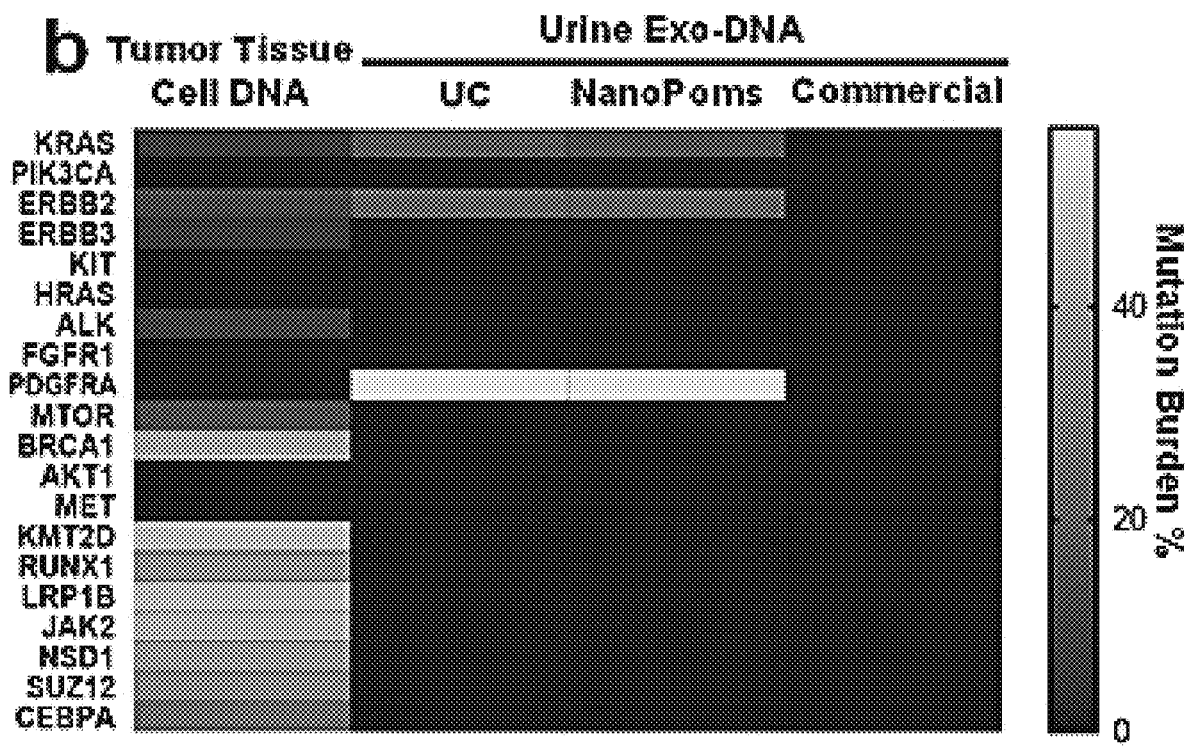
FIG. 19B shows the results from NGS GeneRead analysis of tumor cell DNAs from the matched BC patient, compared with urinary EV DNAs prepared by UC, NanoPoms, and commercial beads.

Bladder cancer (BC) is characterized by a large number of genetic alterations. EVs have been found carrying double-stranded DNA fragments, and genomic alterations in cancers. Thus, detecting DNA mutations carried by urinary tumor EVs is emerging, yet challenging, due to the needs of highly pure sample preparation which enables the sensitive detection. The 11 BC patient urine samples were used to isolate EVs by UC, NanoPoms, and commercial bead approaches in parallel, with 4 healthy urine samples as the control group. The NGS GeneRead AIT panel was used to identify the most cancer relevant 1,411 variants. UC preparation was found insensitive on cancer relevant variant detection, as it requires much larger urine sample input (4 mL) with more than 100 ng EV DNAs to give detectable variant signals (FIG. 19A). We suspect that UC isolated EV DNAs contain more genes which are not specific to cancer. The PDGFRA variant (c.1432T>C, p.Ser478Pro) with 56.8% frequency was detected from a healthy individual in the control group using UC preparation, but not from NanoPoms preparation. In the BC disease group, NanoPoms isolated sEV enabled much enhanced detection sensitivity and specificity to BC relevant mutations including KRAS, PIK3CA, and ERBB2, which only consumed 1 mL urine sample with using about 10-50 ng sEV DNAs. However, commercial bead isolated EVs using the same urine sample input did not yield sufficiently enriched DNAs for sensitive detection of cancer relevant variants (FIG. 19A). In order to validate whether the gene mutations found in urinary EVs are from the urological tumor, we evaluated the matched patient tumor tissue. The NGS GeneRead analysis of tumor tissue cells showed the consistent mutations of KRAS and ERBB2 which also were presented in the urinary EVs from the same BC patient. Although as one might expect, more mutations were detected in the tumor tissue, including MTOR and BRCA1; however, the pathogenic PDGFRA variant (c.1939A>G, p.Ile647Val) was found in the urinary EVs from both UC and NanoPoms preparations, but not in the tumor tissue cells (FIG. 19B). It is worth mentioning that the PDGFRA variant (c.1939A>G, p.Ile647Val) has been recognized as the tumor marker from the bladder urothelial carcinoma and the gastrointestinal stromal tumor, which indicates that circulating sEVs could be a good surrogate and biomarker resources for tumor cells.

Figure 19C:
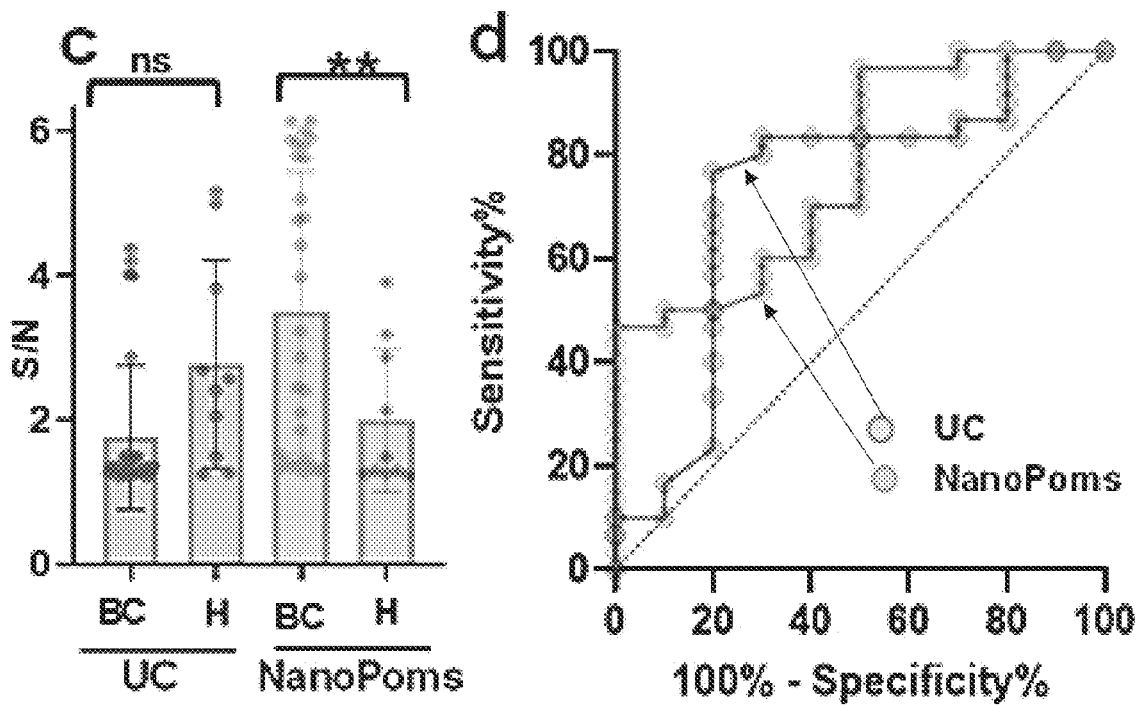
FIG. 19C shows the digital droplet PCR analysis of EGFR (Thr790Met) extracted from purified EVs using both NanoPoms (pink dots) and UC (blue dots) approaches from 30 bladder cancer urine samples with 10 healthy individuals as the control group. d) Receiver operating characteristic (ROC) analysis of ddPCR detection of EGFR showing diagnostic performance using NanoPoms prepared DNAs compared with UC preparation. The a.u.c (Area Under the Curve) for NanoPoms preparation is 0.78 with p=0.01. The a.u.c. for UC preparation is 0.71 with p=0.04.
Figure 20:
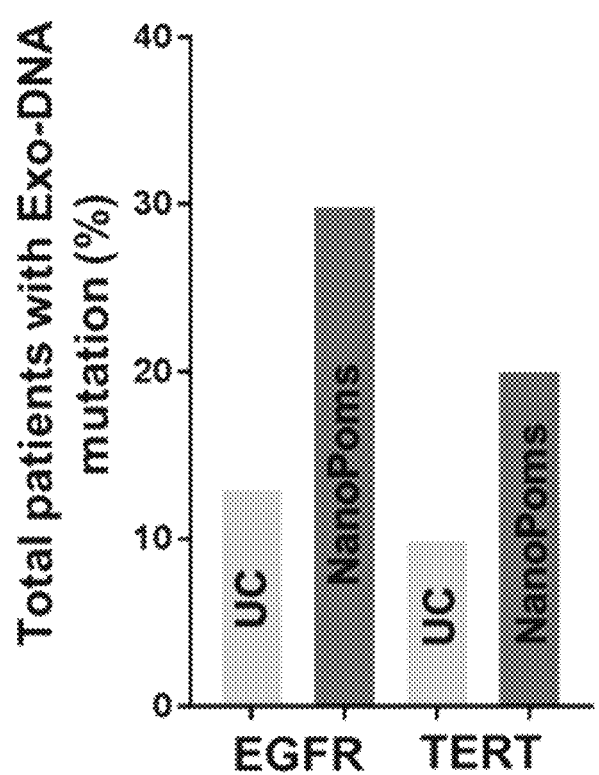
FIG. 20 is a graph of the ddPCR analysis of the mutation frequency using DNAs isolated from either NanoPoms or ultracentrifugation (UC) prepared urinary EVs.

We also analyzed urinary EV-derived DNA mutations from both UC and NanoPoms preparations using ddPCR. A total of 30 bladder cancer patient urines were analyzed with 10 healthy individuals as control group. With the same EV DNA input (10 μg), EGFR (Thr790Met) and TERT (C228T and C250T) were detected. We observed much higher signal amplitudes from NanoPoms prepared EV DNAs than that from UC approach (FIG. 19C and FIG. 20). The average patients' EGFR Wt copy number is 3185.4±468.3 from NanoPoms approach, which is 12.8-fold higher than that from UC approach (248.9±46.4) with 3-fold higher mutation detection efficiency (FIG. 20). The overall detection signal to base ratio from patient group is statistically higher than that from control group (FIG. 19C) with significant diagnostic value (FIG. 19D) from NanoPoms preparation, in contrast to UC preparation which is unable to differentiate patient group from the healthy control group (p>0.05). This result indicates the high potential of NanoPoms prepared sEVs for developing more accurate liquid biopsy cancer diagnosis.

Figure 21:
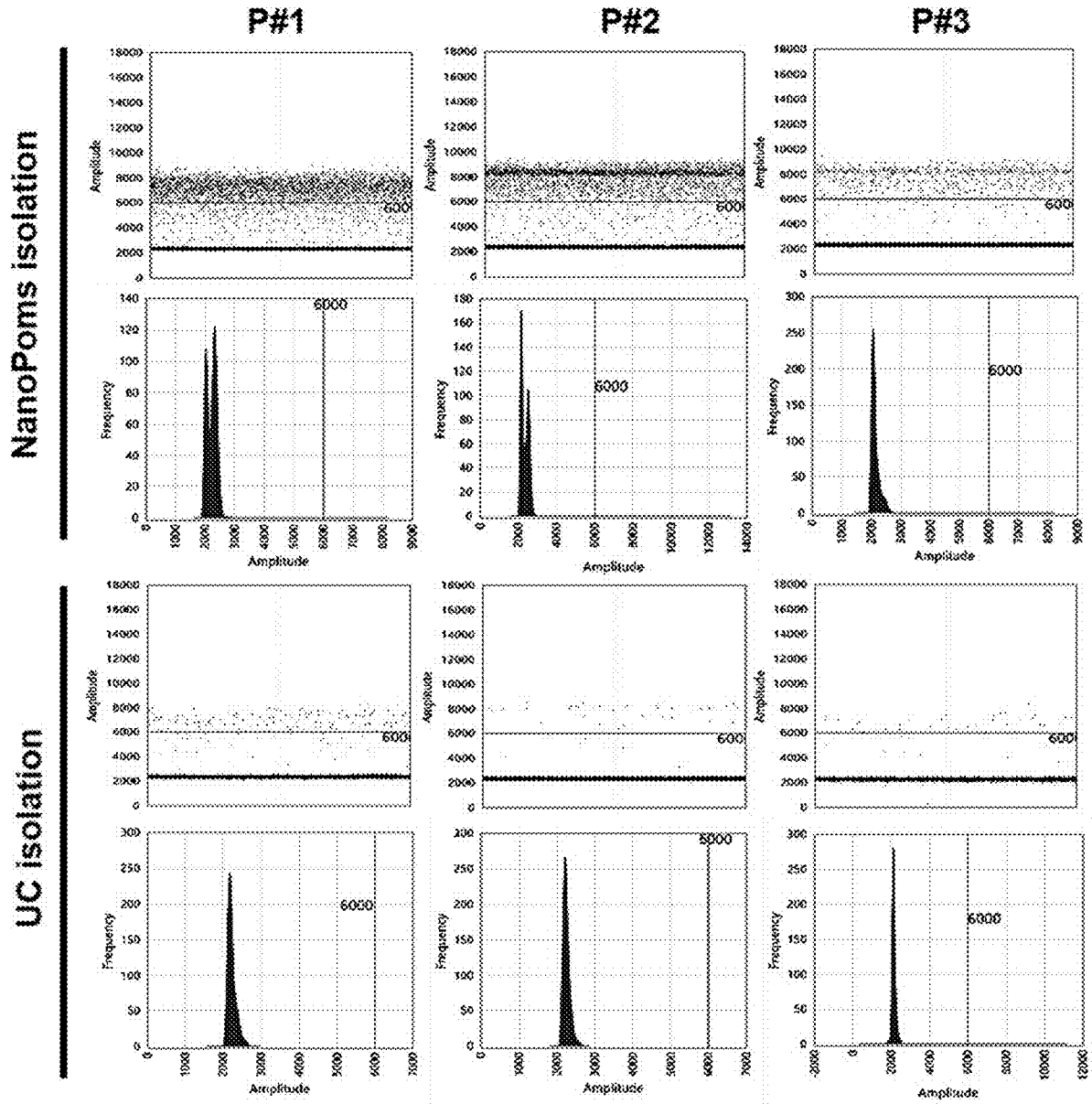
FIG. 21 shows the ddPCR analysis of NanoPoms isolated sEV DNAs showed the EGFR heterozygosity in the three bladder cancer patients. In contrast, UC isolated EV DNAs from the same sample input did not detect the EGFR heterozygosity in patient 2 and patient 3. The DNA copy number was substantially lower in UC prepared EV DNAs as compared to NanoPoms.

Interestingly, we also observed EGFR heterozygous mutations in three BC patients while conducting ddPCR analysis of NanoPoms prepared urinary sEV DNAs (see FIG. 21). In contrast, UC isolates from the same patients 2 and 3 could not show such heterozygous mutation (FIG. 22 and FIG. 21). In order to further validate this observation, we obtained the matched patient plasma and buffy coat with white blood cells (WBC) as the control. NanoPoms preparation allows to pull out marker specific sEV populations based on the exosomal surface markers (CD9, CD63, and CD81) to match urinary EV populations, which avoids the interferences from other microvesicles or non-pathogenic vesicles. Afterwards we used Sanger sequence to confirm the presence of the EGFR heterozygosity for patients 1, 2 and 3. Results were consistent with ddPCR analysis from NanoPoms preparation. As expected, the EGFR heterozygosity was not detected from matched patient WBCs. Thus, these results clearly support that marker specific capture and release enabled by NanoPoms beads can significantly enrich tumor-associated sEVs for sensitive mutation detection. Although the UC preparation yields larger numbers of vesicle particles, their specificity and purity to tumor-associated sEVs are much less.

NGS Analysis of Urinary EV Small RNAs.

Analyzing RNAs within urinary EVs has been emerging with needs for non-invasive, early detection, and timely medical checkup of BC. EV long non-coding RNAs (lncRNAs) PVT-1, ANRIL and PCAT-1 have been reported as the novel biomarker in BC diagnosis. However, NGS profiling of microRNA from tumor derived urinary EVs has not been exploited yet, which requires highly pure and consistent sample preparation. In this study, we used NanoPoms approach to purify sEVs from both BC and the healthy individual urine samples for comparing urinary EV microRNA profiles with UC preparations. The distribution of small RNA categories from NanoPoms EV preparation showed more lncRNAs in both the BC group and healthy control group (42% from NanoPoms vs. 18.9% from UC) (Table s2). In contrast, UC preparation leads to the higher percentage of tRNA. Although the exact role of EV lncRNAs is not well understood yet, several studies have showed exosomal lncRNAs are novel biomarkers in cancer diagnosis and are highly associated with cancer progression and cellular functions. Only a small number of lncRNAs has been investigated which may be due to the variation and uncertainty imposed by EV preparation differences.

Figure 23A:
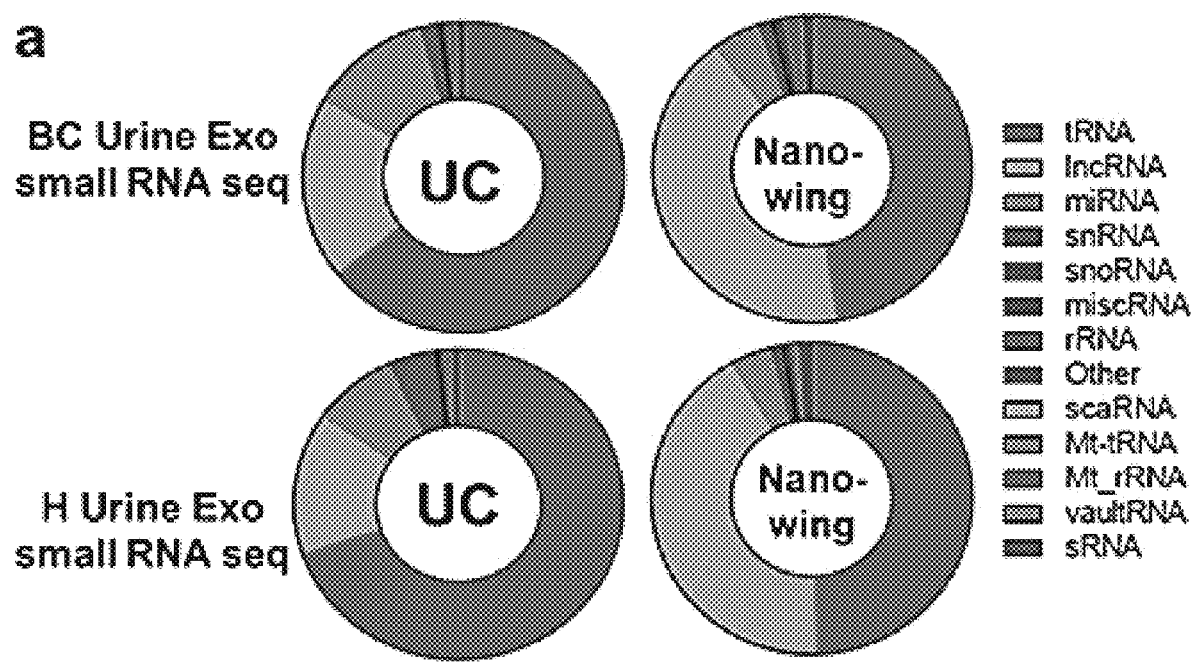
FIG. 23A shows the distribution of small RNA categories from both NanoPoms and UC prepared urinary EVs from BC patient and healthy control.
Figure 23B:
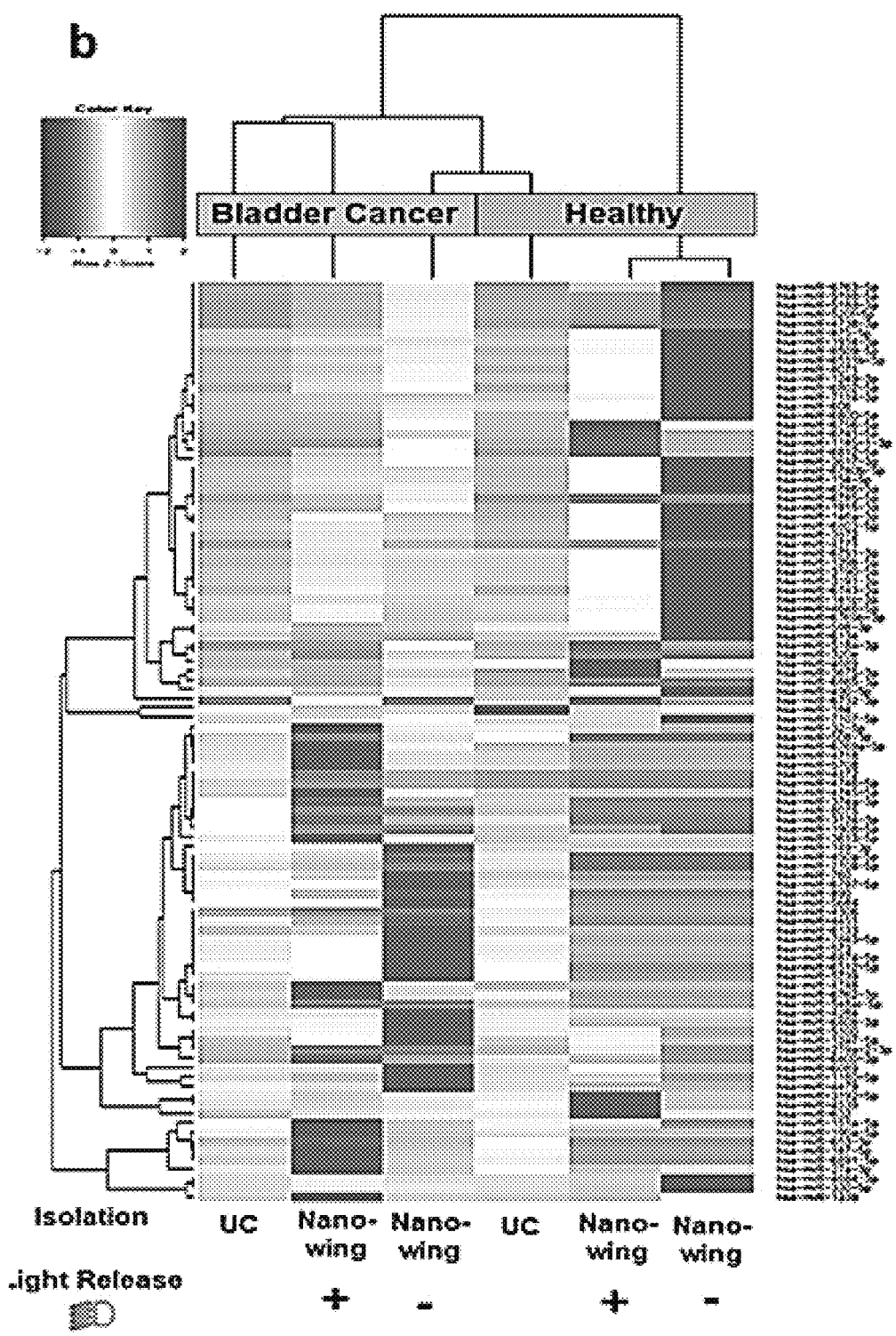
FIG. 23B is a heatmap with dendrogram clustering analysis depicts the top 100 highly expressed miRNAs from urinary EVs isolated from both BC patient and healthy individual using UC, NanoPoms without or without light release process. Red color indicates a higher expression z-score. Hierarchical clustering was performed, using the Spearman correlation method. NanoPoms isolation approach with or without light release processes have been clustered together due to higher similarities in their transcript expressions.
Figure 24:
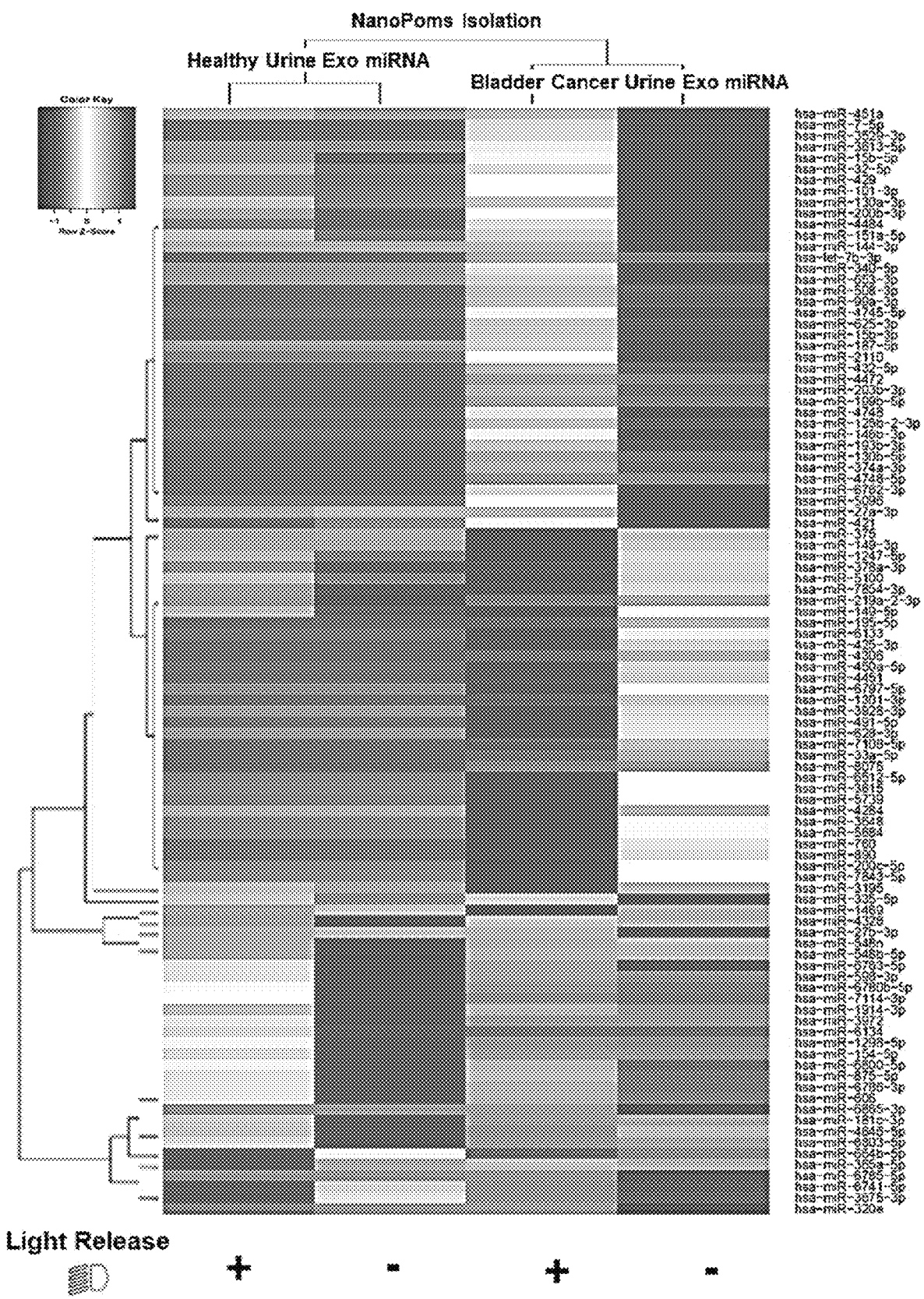
FIG. 24 is a heatmap with dendrogram clustering analysis depicts the top 100 highly expressed miRNAs from urinary EVs derived both the BC patient and the healthy control which were isolated by the NanoPoms approach with and without light release process. Red color indicates a higher expression z-score. Hierarchical clustering was performed, using the Spearman correlation method.

We further look into the top 100 miRNAs expression profiles as shown in FIG. 23B. The heatmap clustering analysis indicates the clear differentiation between BC group and healthy control from NanoPoms preparation, in contrast to UC preparation. We also investigated the influence of photo cleavage process on the integrity of overall EV miRNAs (FIG. 24). We did not observe significant differences in heatmap profiles with and without photo cleavage process. Generally, miRNAs are not stable and sensitive to environmental changes. The NanoPoms EV preparation is able to maintain the differentiation ability between BC and healthy control groups, in contrast to UC approach.

Figure 23C:
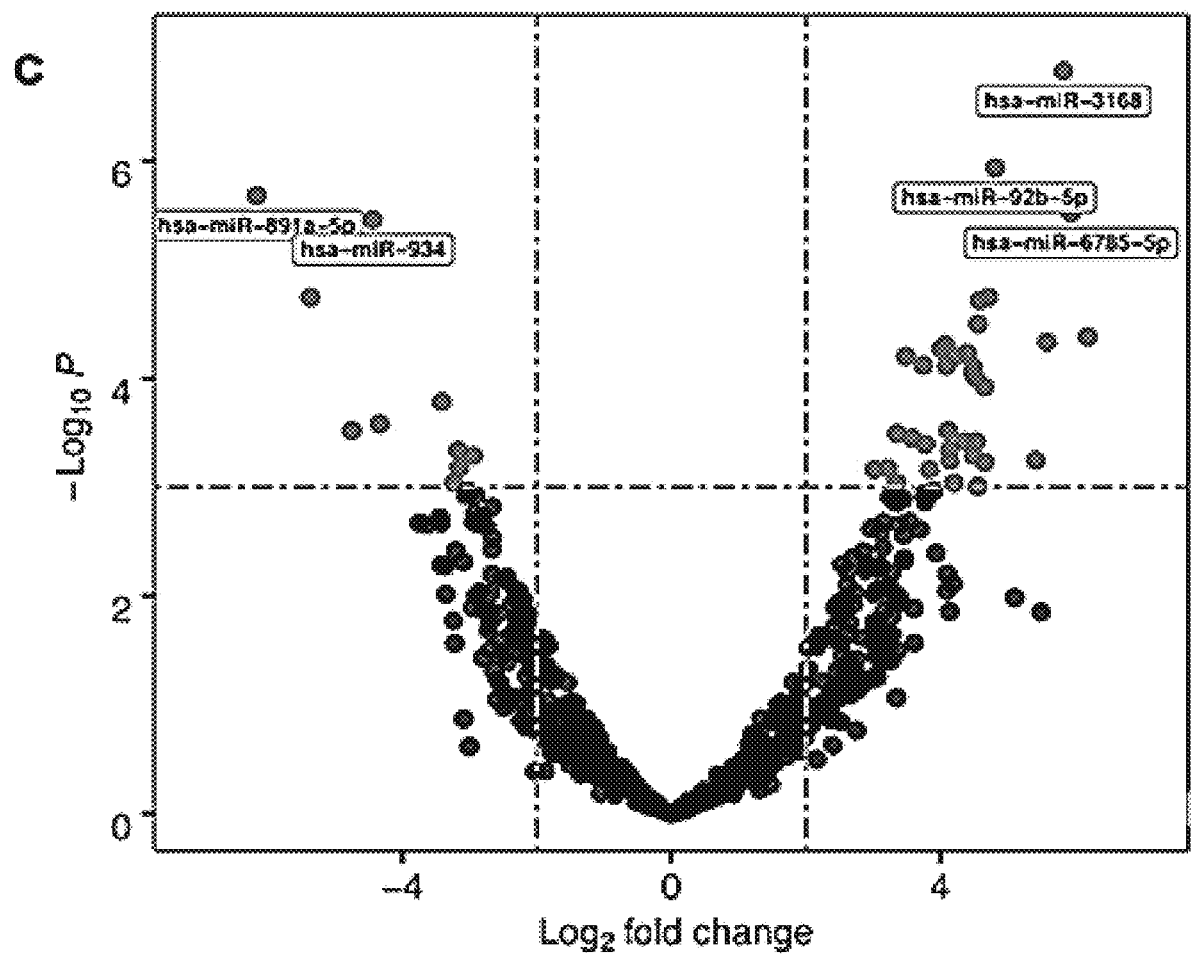
FIG. 23C is a Volcano plot analysis that depicts the most biologically significant urinary EV miRANs with large fold changes identified by using NanoPoms preparation compared to UC preparation. Top 5 highly significant miRNAs are labeled in plot, which are from NanoPoms preparation.

In order to further interpret urinary EV miRNA profiles and characterize the influences imposed by EV sample preparation steps, we used the volcano plot to analyze the statistical significance (P value) versus fold-gene expression changes from both UC and NanoPoms preparations. It is interesting to note that top 10 miRNAs were highly enriched from the NanoPoms preparations, including hsa-miR-3168, hsa-miR-92b-5p, hsa-miR-891a-5p, hsa-miR-934, and hsa-miR-6785-5p (FIG. 23C and Table s3). We searched the reported miRNA functions and found those miRNAs were reported as the cancer relevant markers specifically sorted into exosomes (Table s3). For instance, hsa-miR-3168 has been reported to be enriched in exosomes via a KRAS-dependent sorting mechanism in colorectal cancer cell lines and is known as the melanoma mature miRNA. The miR-92b-5p has been found to play a critical role in promoting EMT in bladder cancer migration. The hsa-miR-934 is an essential exosomal oncogene for promoting cancer metastasis. NanoPoms preparation offered much higher molecular relevance with tumor derived exosomes, which is crucial for developing biomarkers in liquid biopsy analysis of cancers.

Proteomic Analysis of Urinary EV Proteins.

Figure 25A:
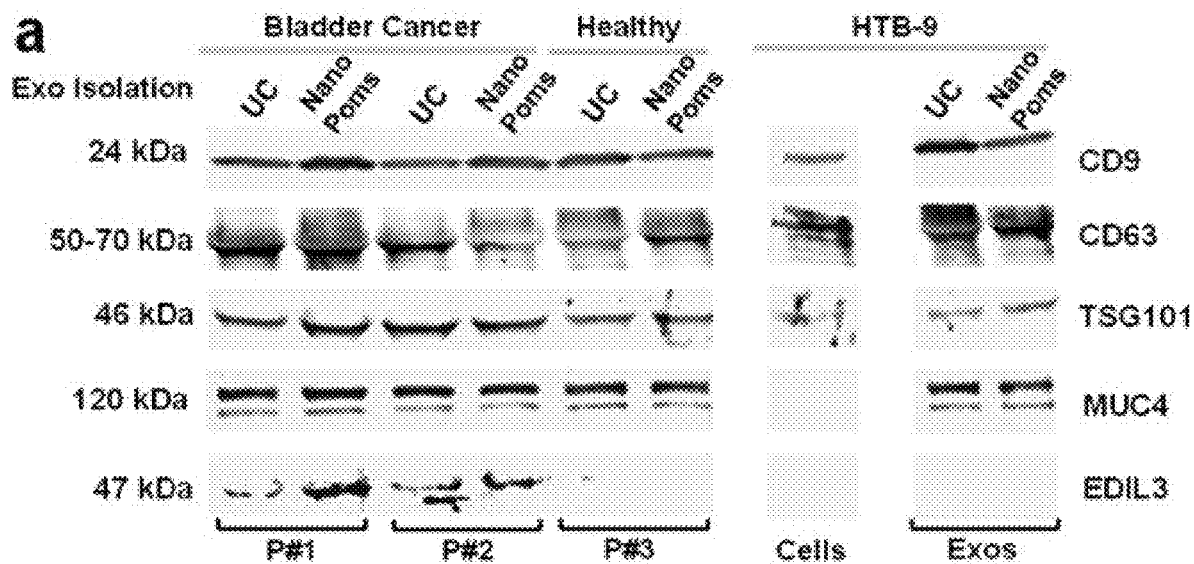
FIG. 25 A shows Western blotting analysis of urinary EV proteins prepared by both NanoPoms and UC approaches. Two BC patients and one healthy individual urine samples were used with HTB9 cells and their EVs from conditioned media as the control. Protein loading amount is consistent between samples (~5 µg).
FIG. 25C shows a Venn diagram illustrating the relationship of proteomes from BC and healthy urinary EVs prepared by the NanoPoms approach, with references from ExoCarta Exosome Protein Database and the Urinary Exosome Protein Database.

By introducing the non-invasive urinary protein biomarkers, the cystoscopic evaluations in BC diagnosis can be confirmed with improved accuracy, which has significant clinical values. EDIL-3 (Epidermal growth factor (EGF)-like repeat and discoidin I-like domain-containing protein 3) and mucin 4 (MUC 4) both have been found in exosomes purified from BC patient urines. We selected exosomal markers CD9, CD63, and TSG101, as well as the EDIL-3 and MUC4 for Western blotting analysis of urinary EV proteins prepared by both UC and NanoPoms, with the human bladder carcinoma cell line HTB9 as the control (FIG. 25A). The exosomal markers CD9, CD63, and TSG101 were consistently expressed in urinary EVs, HTB9 cells and their EVs, which indicates consistent isolation of EVs, although there is no significant difference between two preparation methods. The expression level of EDIL-3 is significantly higher in BC patients than healthy individuals, but not in the tumor cell line or their EVs from conditioned media. MUC4 protein marker was only observed in the human urinary EVs and HTB9 EVs, but not in HTB9 cells. This observation supports the previous report that EDIL-3 and MUC 4 are highly promising biomarkers in developing urinary EV-based BC diagnosis and prognosis tests.

Figure 25B:
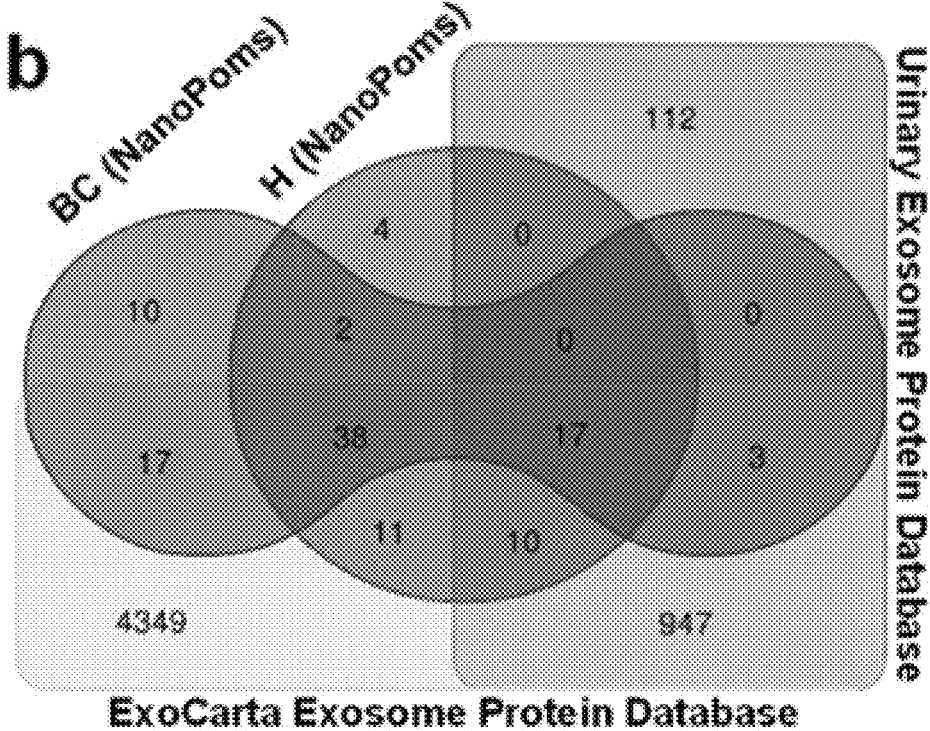

The proteomic profiling of urinary EVs from both UC and NanoPoms preparations was shown in FIG. 25B. The identified proteins were compared with the ExoCarta Exosome Protein Database and the Urinary Exosome Protein Database. Several proteins associated with exosome biosynthesis were observed, such as proteins PIGQ and PAPD7 involved in Golgi apparatus, the cytosol protein S100-A7 and A9 found within the exosome lumen which is engaged with natural membrane budding process during multivesicular body formation. We also observed a diverse group of cytosolic enzymes (glyceraldehyde-3-phosphate dehydrogenase) and cytoskeletal constituents (actin, Beta-actin-like protein 2 ACTBL2, and myosin-9). Although the majority of proteins are shared identifications within BC patient and healthy control groups (~65%), as well as the databases we used, interestingly, we found 10 proteins which are uniquely identified only from BC patient using NanoPoms preparation (Table s4). Those proteins have previously been reported to be associated with bladder cancer metastases, including IRAK4, KRT23, and RALGAPA2 (full list in Table s4). Also 4 proteins were found uniquely in the healthy group using NanoPoms preparation, but not reported by ExoCarta and Urinary Exosome Protein Databases. From the Human Protein Atlas database (www.proteinatlas.org/), those proteins are intracellular and associated with vesicles, Golgi apparatus, and secreted pathway. The identifications are broadly consistent with that expected for exosomes and compatible with other researchers' investigations. Approximately 35% of proteins do not overlapped between the BC patient and the healthy control, which further support the utility of NanoPoms prepared sEVs for aiding the diagnosis of BC.

Figure 25C:
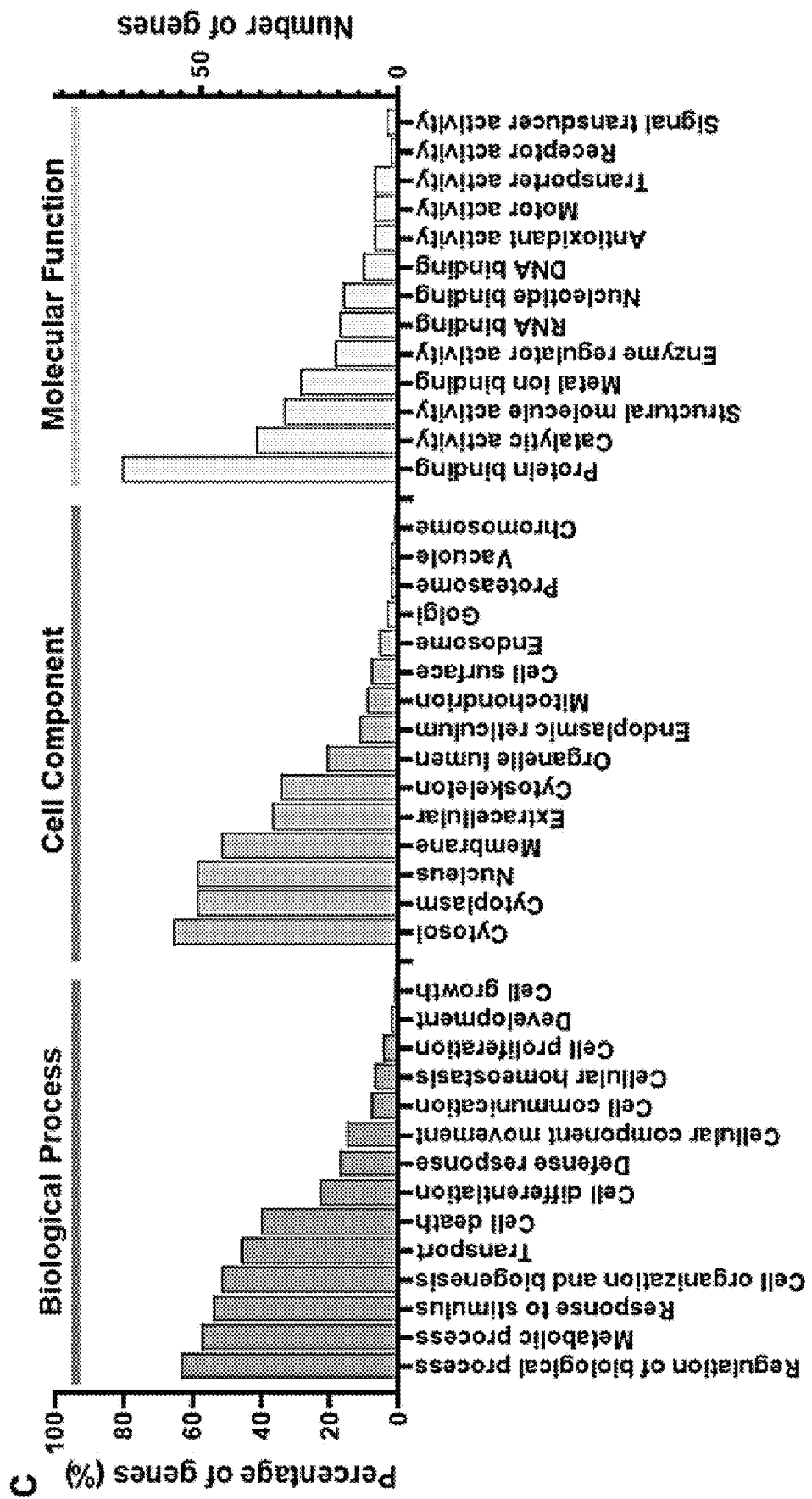

Identified proteins were classified by encoding genes which indicate the majority are located within membranous vesicles, cytosol, cytoplasm, and the cytoskeleton, and some are located in Golgi (FIG. 25C). The biological processes associated proteome revealed significant associations with regulation of biological process, metabolic process, response to stimulus, cell organization and biogenesis, transport, and the cell death. The protein binding molecular function from this proteome is dominant. Results exhibit good specificity to exosomal proteome, indicating NanoPoms preparation could provide a pure and high-quality exosome type sEVs, which facilitates the important research area in EV proteomics or multi-omics.

In Vivo Biodistribution Study of NanoPoms Prepared sEVs.

Figure 26A:
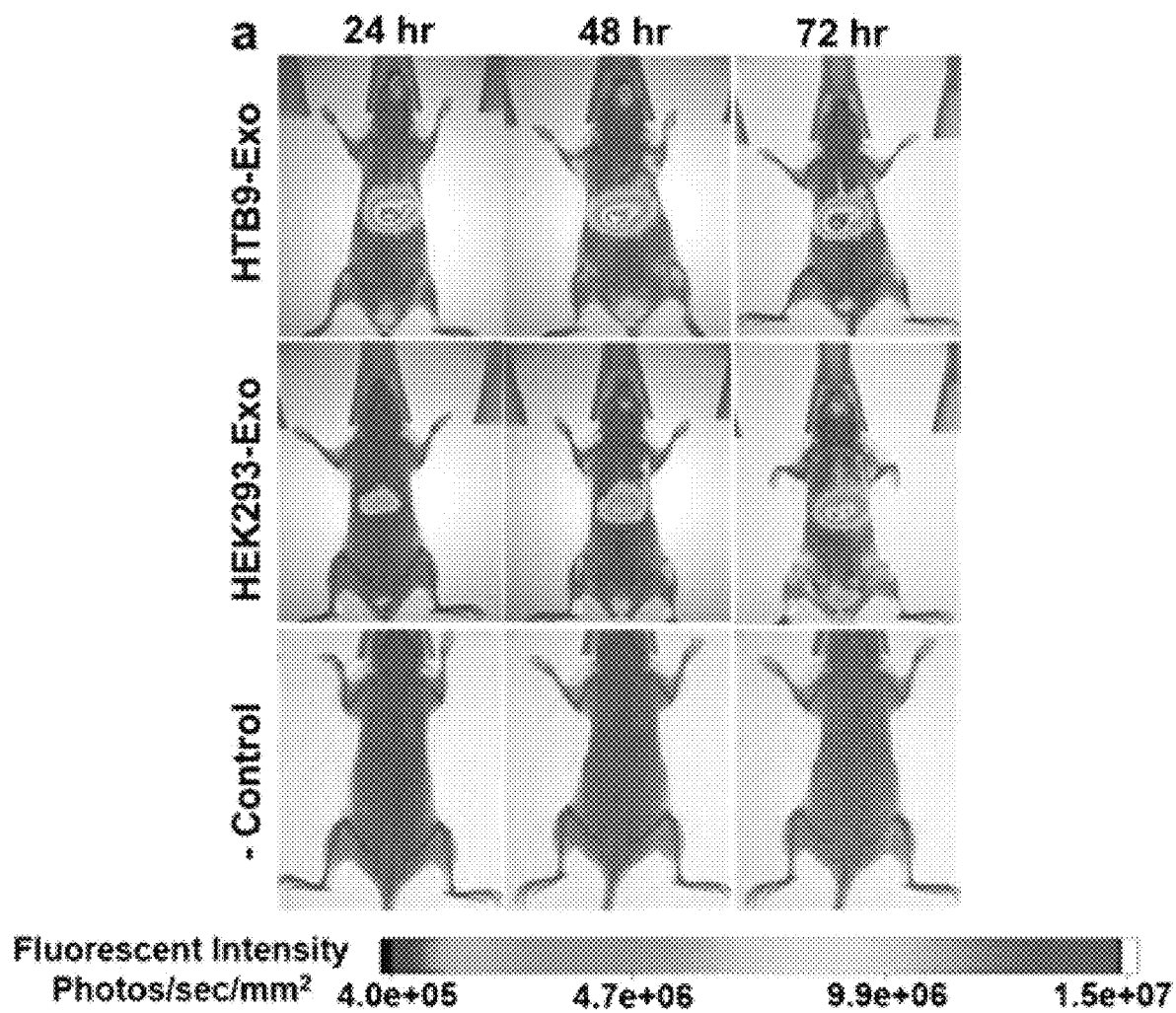
FIG. 26A shows representative IVIS images at 24 hours, 48 hours, and 72 hours post-injection of live mice. The HTB9 tumor cell derived sEVs and non-malignant HEK cell derived sEVs with DiR labeling ($2.0 \times 10^9$ particles/ml) were prepared by NanoPoms approach for intravenous tail injection into BALB/cJ mice. The buffer solution without EVs was used as the negative control.
Figure 26B:
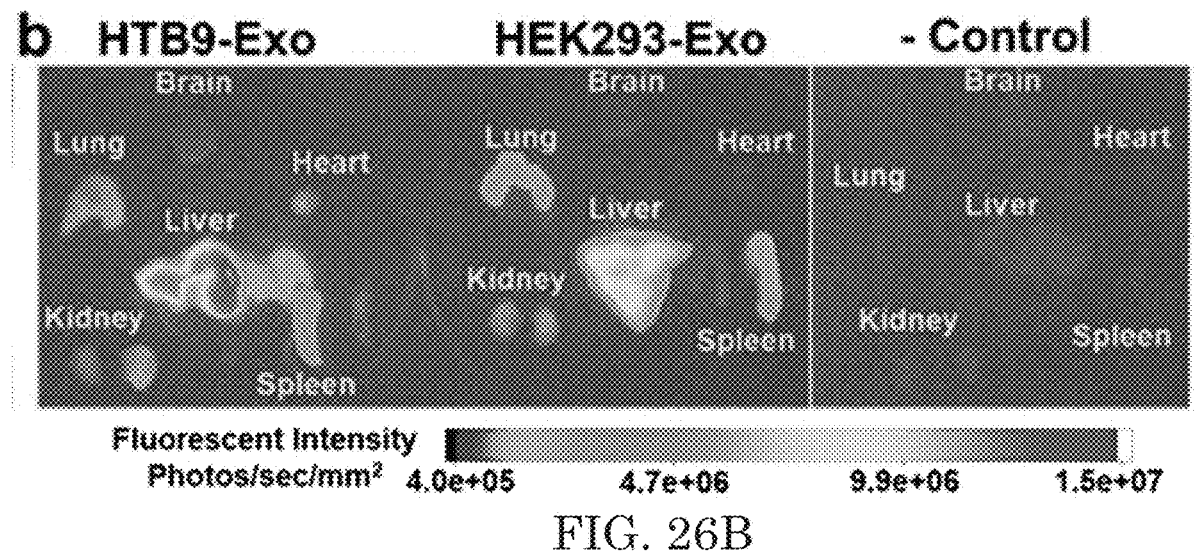
FIG. 26B shows representative IVIS images of harvested organs (lung, liver, kidney, spleen, heart, and brain) at 48 hours and 72 hours post injection from mice.
Figure 26C:
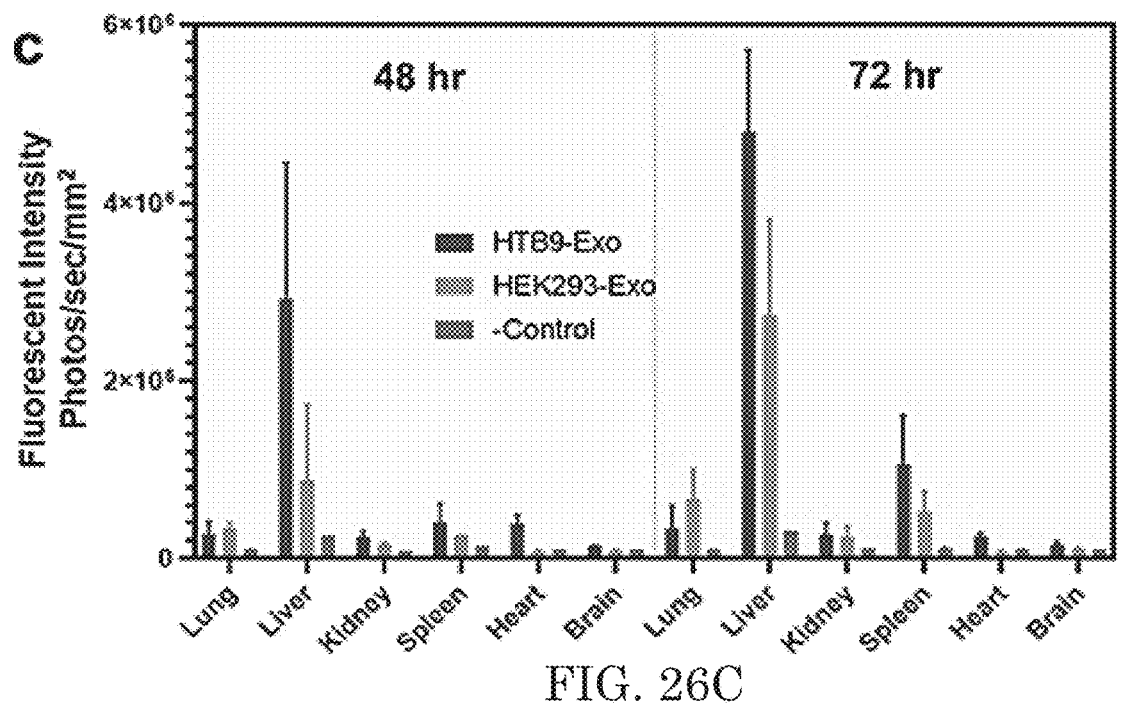
FIG. 26C shows the fluorescence signals normalized with negative control from IVIS images in each organ harvested at 48 hours and 72 hours post injection (n=2, mean±SD).

The NanoPoms preparation of sEVs via marker specific capture and release is able to collect intact, pure and homogenous sEV subtypes. Due to the on-demand, light-triggered release process, the molecular engineering, such as the surface modification, drug loading, or dye labeling, can be implemented to immunomagnetically captured EVs before washing and releasing. This protocol avoids the redundant post purification of small molecules from isolated sEVs, which is often challenging and causes contaminations. For instance, the remaining free dye during in vivo tracking of EVs could cause false signals with longer distribution half time, unspecific staining or tissue accumulation. With such unique capture and on-demand release, we can prepare pure and intact sEV samples without contamination. In this study, we prepared sEVs from HTB9 cells and non-malignant HEK cells with DiR labeling for intravenous tail injection into BALB/cJ mice. The buffer solution from beads washing step (without EVs) was used as the negative control. From these representative images in 24, 48, and 72 hr time intervals post injection, the fluorescent whole mouse imaging is unable to provide enough precision to describe the levels of sEV distributions in tissue organs (FIG. 26A). Thus, to minimize signal interference, the organs were harvested and imaged ex vivo in the time intervals of 48 and 72 hr, respectively (FIG. 26B, 26C). To rule out of the signal originating from the blood in the organs or from the free dye, we normalized the EV tracking signal with the negative control signal to affirm the in vivo EV tacking. In fact, the negative control images did not show much detectable signals indicating no remaining free dye during in vivo tracking of sEVs as the background signal. By further observing the harvested organs, HTB9-derived sEVs exhibit different biodistribution profile in lung, liver, kidney, spleen, heart, and brain, as compared to sEVs isolated from the non-malignant HEK293 cells. sEVs prepared from the HTB9 tumor cells were more concentrated in the liver and spleen with gradually increased intensity from 48 hrs to 72 hrs post injection. In contrast, non-malignant HEK293-derived sEVs tend to spread from liver to lung and spleen after 48 hrs post injection. Although HTB9 sEV biodistribution profile has not been reported elsewhere previously, the HEK293 sEV biodistribution profile is consistent with reported study in C57BL/6 mice. FIG. 26C provides the repetitive and quantitative analysis of biodistribution pattern over time. The results potentially indicate the distinctive biodistribution profile from cancer-associated sEVs which could be very important for understanding tumor cell-mediated communications within the microenvironment. Currently, substantial efforts have been made for using sEVs as therapeutic agents or delivery vehicle in vivo. Thus, being able to reproducibly prepare pure and homogenous sEVs is critical for maintaining consistent biodistribution patterns.

Discussion

All living cells secret EVs which are diverse populations with heterogeneous molecular functions. Recent and substantial research has shown the heterogeneity of EVs in terms of density, molecular cargos, and morphology, which are even released by a single cell type. Our recent study also observed that molecular packaging of secreted EVs or exosomes is highly variable upon the change of cellular culture environment as well as surrounding community. Thus, the more advanced analytical methods are urgently needed to be able to decipher such heterogeneity in precision. The bulk measurements could average out or mask essential disease associated signaling markers, leading to the misinterpretation of mechanisms. Additionally, for therapeutic delivery, the well-defined molecular components from the homogenous EV population is also critical to precisely maintain controllable biodistribution pattern and delivery behavior. Due to the unique 3D nanographene structure and specific marker defined capture-release process, our developed NanoPoms isolation approach focuses on the pure and homogenous sEV subpopulations for advancing the clinical utility.

Figure 22A:
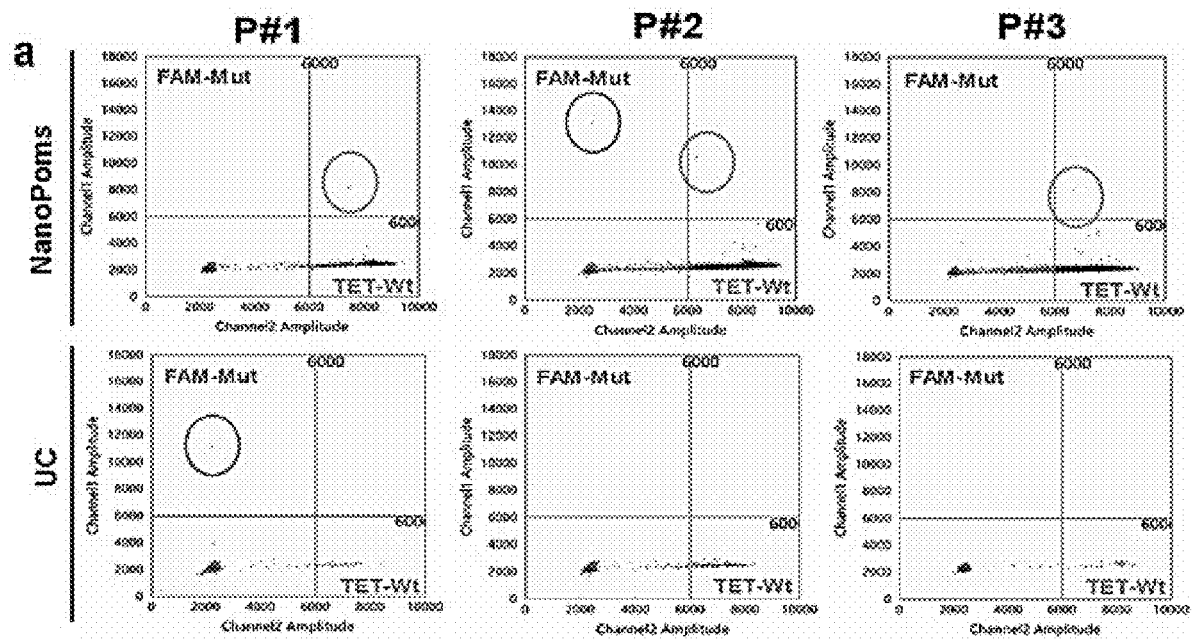
FIG. 22A shows the ddPCR analysis of DNAs from NanoPoms prepared urinary sEVs for detecting EGFR (Thr790Met) in three BC patients, compared with UC EV preparation.
Figure 22B:
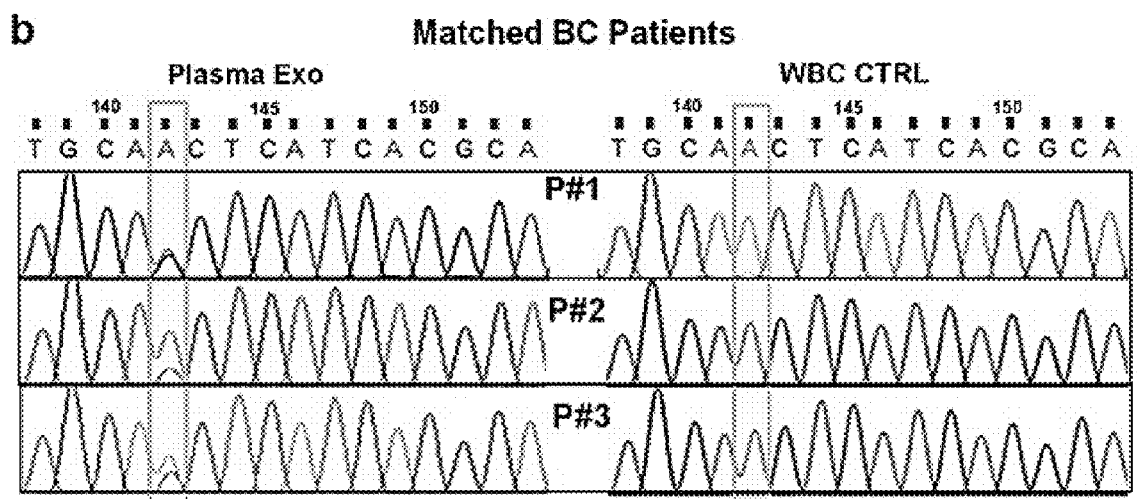
FIG. 22B shows the Sanger sequence validation of NanoPoms prepared plasma sEV EGFR heterozygosity from matched patients in FIG. 22A. DNAs from the corresponding patients' white blood cells (WBC) as the wild-type control.

The NGS analysis in our study demonstrated that DNAs isolated from NanoPoms prepared sEVs are enriched for tumor-associated DNA mutations which are highly relevant to the bladder cancer (FIG. 19A) and comparable to matched patient tumor tissue cells (FIG. 19B). The ddPCR analysis also confirmed such performance with significantly higher detectable copy numbers (FIG. 19C and FIGS. 20 and 21). The heterozygosity also can be readily detected from very low level of copy numbers in NanoPoms prepared sEV DNAs, as confirmed by Sanger sequencing with matched patient plasma and buffy coat (FIGS. 21 and 22A-B). The NGS analysis of sEV RNAs prepared by NanoPoms also reveals the distinctive profiles between BC patient and healthy individual, in terms of RNA types and miRNA levels, in contrast to UC sample preparation (FIG. 23A-B, Table s2). Most importantly, the top 10 miRNAs identified from NanoPoms sEV preparation are highly relevant as the important cancer markers specifically sorted into exosomes (FIG. 23C and Table s3). This evidence further supports that specific cancer-associated biomarker are enrich in exosome type circulating sEV and can serve as surrogates for tumor cells.

The miRNAs represent the most dynamic nucleic acid cargos in EVs, which is relatively unstable and sensitive to external stimulus and changes. Thus, in order to gauge the impact of light release process on sEV isolation via Nano-Poms approach, we compared the miRNA profiles with or without light release process, which did not show statistically significant differences based on dendrogram clustering analysis (FIG. 23B and FIG. 24). The light release process also is able to ensure the specificity via releasing specifically captured sEVs only, not non-specific binders. This data supports the quality and integrity of NanoPoms prepared sEVs as a novel, rapid, and easy-to-use method. Currently, although urinary miRNA profiling is highly essential for BC diagnosis, such study and relevant database have not been fully established yet. NanoPoms based EV sample preparation could potentially speed up this research direction by offering much simple and accurate sample preparation.

The urinary sEV cargos at the protein level from our study reveals the consistent expression of exosomal proteins CD9, CD63, and TSG101 from both patient urinary EVs and cell lines from both UC and NanoPoms preparations. However, EDIL-3 levels have been observed much higher in BC patient urinary EVs compared to healthy individuals, which is consistent with reported literature, indicating the high-quality preparation of exosome sEVs using NanoPoms approach (FIG. 25A). Further, the proteomic profiling also supports that NanoPoms prepared urinary sEV proteins can be used to differentiate BC disease from healthy status (FIG. 25B-C, and Table s4) with unique identification of pathogenic EV proteins, suggesting a promising avenue using NanoPoms prepared sEVs to develop non-invasive bladder cancer diagnosis.

In order to further prove the integrity and biological activity of NanoPoms prepared sEVs, in vivo biodistribution study exhibits distinctive distribution patterns between tumor-associated sEVs and non-malignant sEVs (FIG. 26). This result may indicate that different subtypes and sources of EVs could have impact on the performance of drug delivery while using EVs as the carrier. To date, the therapeutic potential of different subpopulations of EVs, even from a single cell type, is not well known. It has been discussed that possibly only a small fraction of the EVs from a cell can mediate the therapeutic effects, and another EV population could have opposing effects. Thus, the reproducible isolation of specific sEV subpopulations are essential to support the development of EV-based methods for effective therapeutic delivery. However, current existing EV isolation strategies are still unable to reproducibly differentiate sEV subpopulations. Our NanoPoms approach for enriching exosome type sEVs with marker definition could open a new avenue for preparing pure and homogenous sEVs with improved diagnostic and therapeutic efficacy.

Methods

NanoPoms immunomagnetic particles fabrication and characterization. The proprietary bead fabrication follows the protocol of $Fe_3O_4/SiO_2$ core-shell-based particle (~1 μm) method with surface anchored graphene oxide nanosheets via carboxamide covalent bonds and EDC/NHS chemistry, and further modified with (3-aminopropyl) triethoxysilane (APTES) and streptavidin (Vector Laboratories, SA-5000). Beads were washed with PBST then resuspend in 1 ml PBST and 0.09% $NaN_3$ solution for storage at 4° C. In this study we used the pan capture with a mixture of CD9, CD63, and CD81 antibodies for bead-conjugation. For in vivo biodistribution study, we used CD9 antibody conjugated NanoPoms particles beads to prepare HTB9 and HEK cells derived sEVs. After bead fabrication and conjugation, XPS analysis was used (PHI 5000 VERSA PROBE II) with an Al anode of the x-ray source (46.95 eV) and 100μ X-ray beam size for operating at 23.2 W. The power of the source was reduced to minimize X-ray damage for analyzing EVs on bead surface.

The EV isolation from patients' plasma, urine, or cow milk and conditioned cell culture media were performed by incubation of 100 ul antibody-beads complex with 1 mL of samples at 4° C. overnight. After washing, the photo release was performed using Analytikjena UVP 2UV Transilluminator Plus at 365 nm wavelength at 4° C. for 15 min (~6 $mW/cm^2$). The UC isolation of EVs followed the well-documented protocols published previous. Briefly, to remove any possible apoptotic bodies and large cell debris, the supernatants were centrifuged at 10,000 g for 30 mins, then transferred to ultracentrifuge tube (Thermo Scientific, USA) for ultracentrifugation at 100,000 g for 70 min (Sorvall™ MTX150 Micro-Ultracentrifuge, USA), with second ultracentrifugation (100,000 g for 70 min) for finally collecting EV pellets. The size characterization of EVs was performed using the nanoparticle tracking analysis (NTA) Nano-Sight LM10 (Malvern Panalytical). Post-acquisition parameters were adjusted to a screen gain of 10.0 and a detection threshold to 5. Standard 100 nm nanoparticles were used for calibration. Appropriate sample dilution in 1×PBS was evaluated before every measurement with five repeats for each measurement.

sEV DNA extraction and NGS sequencing. Frozen urine samples were thawed overnight at 4° C. and pre-centrifuged at 4° C. 10,000 g for 30 min to remove cell debris. By using NanoPoms isolation, the extracted sEVs were treated with DNase I before DNA extraction. The QIAamp DNA Mini Kit (Qiagen, 51304) was utilized to extract DNA from all EV samples. The addition of 1 μl of an aqueous solution containing 10 μg of carrier DNA (poly dA) to 200 μl Buffer AL was used to ensure binding conditions are optimal for low copy number DNA according to the manufacturer's protocols. DNA was Eluted in 20 μL Buffer AE. DNA concentrations were measured using a Nanodrop platform at an absorbance at 260 and 280 nm subtracted by the background value of carrier ploy dA only.

The library preparation by targeted enrichment using Qiagen GeneRead QIAact AIT DNA UMI and GeneRead clonal Amp Q Kits, was subjected to next-generation sequencing (NGS) to generate FASTQ files (text-based format for storing nucleotide sequences). This test is a targeted NGS Panel that encompasses 30 genes and 1411 variants (AKT1, ALK1, BRAF, CTNNB1, DDR2, EGFR, ERBB2, ERBB3, ERBB4, ESR1, FBXW7, FGFR1, FGFR2, FGFR3, FLT3, GNA11, GNAQ, HRAS, KIT, KRAS, MAP2K1, MAP2K2, MET, NOTCH1, NRAS, PDGFRA, PIK3CA, RAF1, SMAD4, STK11) with variable full exon or partial region. The reads are mapped to the Homo_sapiens_sequence hg19 reference and variants identified using QIAGEN QCI-Analyze pipeline.

The extracted DNAs were amplified by PCR to detect the EGFR (P00533:p.Thr790Met) mutation using forward 5'-ATGCGTCTTCACCTGGAA-3' (SEQ ID NO:60) and reverse 5'-ATCCTGGCTCCTTATCTCC-3' (SEQ ID NO:61) primers. Primers were designed by Primer3Plus online. The PCR assay was performed with Promega GoTaq Flexi DNA Polymerase kit in a 50-μL mixture containing 10 μL of 5×PCR buffer, 0.25 μL GoTaq Flexi DNA Polymerase, M of each primer (IDT, USA) and 20 μL of DNA in an ABI PCR instrument (Applied Biosystems). The PCR conditions were as follows: Initial denaturation at 95° C. for 2 min, followed by 35 cycles at 95° C. for 15 sec, 54° C. for 30 sec and 72° C. for 40 sec, then a hold at 72° C. for 5 min and a final permanent hold at 4° C. The 319 bp DNA size of PCR products were clarified by 1% agarose gel electrophoresis using 5 µL PCR products and remained DNA were purified by QIAquick PCR Purification Kit (Qiagen, 28104). The purified PCR products were sequenced by Sanger Sequencing approach (GeneWiz, USA) using the same primers above.

EV RNA extraction and NGS sequencing. The miRNeasy Mini Kit (Qiagen, 217004) was used to extract total RNA from all EV samples per manufacture's protocols. The amount of 700 µL QIAzol lysis reagent was adapted according to the manual. To achieve a higher RNA yield, the first eluate of 30 µL was applied to the membrane a second time. Isolated RNAs were quantified by High Sensitivity RNA ScreenTape Assay using Agilent TapeStation 2200 (Agilent, 5067-5579, 5067-5580). Total RNA was stored at −80° C. until small RNA Library preparation. The QIAseq miRNA Library is prepared for Single Read 75 bp sequencing, with UMI tag per manufacture's protocols. After small RNA sequencing using Illumina MiSeq system, the Qiagen specific UMI analysis per the kit instruction was performed with details in supplementary information.

Droplet digital PCR. A pair of probes and a pair of primers were designed to detect EGFR and TERT mutation respectively. Due to the short size of the probe, in order to increase the hybridization properties and melting temperature, Locked Nucleic Acid (LNA) bases were introduced on the bases indicated with a "+". One probe was designed to recognize wildtype (5'-TET/T+CATC+A+C+GC/ZEN/A+GCTC/-3' IABkFQ, SEQ ID NO:62). The second probe was designed to recognize the EGFR (P00533:p.Thr790Met) mutation loci, (5'-6FAM/T+CATC+A+T+GC/ZEN/A+GC+TC/-3' IABkFQ, SEQ ID NO:63). Primers were designed to cover both side of detection loci. For TERT, a probe was designed to detect both C228T and C250T mutation as both mutations result in the same sequencing string, with (TERT Mut:/56-FAM/CCC+C+T+T+CCGG/3IABkFQ/, SEQ ID NO:64). A second probe was designed to recognize the C228 loci, also containing LNA bases, (TERT WT, /5HEX/CCCC+C+T+CCGG/3IABkFQ/, SEQ ID NO:65). Probes and primers were custom synthesized by Integrated DNA Technologies (IDT). Amplifications were performed in a 20 µL reaction containing 1×ddPCR Supermix for Probes (No dUTP), (Bio-Rad, 1863024), 250 nM of probes and 900 nM of primers and 8 µL EV DNA template. Droplets were generated using the QX200 AutoDG Droplet Digtal PCR System (Bio-Rad). Droplets were transferred to a 96-well plate for PCR amplification in the QX200 Droplet Reader. Amplifications were performed using the following cycling conditions: 1 cycle of 95° C. for 10 minutes, then 40 cycles of 94° C. for 30 seconds and 60° C. for 1 minute, followed by 1 cycle of 98° C. for 10 minutes for enzyme deactivation. Keep all ramp rate at 2° C./sec. QuantaSoft analysis software (Bio-Rad) was used to acquire and analyze data.

Western blot analysis. The 5 mL of each urine sample for two patients and one healthy control were used for EV isolation and subsequent Western blot analysis. 40 mls of HTB-9 conditional cell culture media and 40 mg cell pellets were also used as controls in this study. Samples were lysed in 1×RIPA buffer supplemented with protease inhibitors for 15 min on ice. Only cell sample were ultrasonicated for 1 min. Protein concentration was quantified using Micro BCA Protein Assay Kit (Thermo Fisher, 23235). The absorbances were read at 562 nm on a Synergy H1 reader (BioTek). All sample concentration were adjusted to 0.1 µg/µL. Western blotting was performed under reducing conditions (RIPA buffer, β-mercaptoethanol and Halt Protease Inhibitor Cocktail, EDTA-Free) at 95° C. for 5 min. 20 µL of protein lysate, each, were loaded onto 4-20% Mini-PROTEAN TGX Precast Protein Gels (BioRad, 4561093). The separated proteins were transferred to a PVDF membrane (BioRad, 1620218). After blocking the membrane in Intercept (PBS) Blocking Buffer (LI-COR, 927-70001) for one hour at room temperature, it was incubated over-night with the primary antibody at 4° C., followed by another incubation with the secondary antibody for half hour at room temperature. The following primary antibodies were used, all diluted in blocking buffer (1:1000): anti-CD9 (Thermo Fisher, 10626D), anti-CD63 (Thermo Fisher, 10626D), anti-EDIL3 (Abcam, ab88667), anti-MUC4 (Abcam, ab60720), anti-TSG101 (Invitrogen, PA5-86445), anti-ANXA7 (LSBio, LS-C387129-100). The secondary anti-mouse and anti-rabbit IRDye 800CW antibodies (LI-COR, 926-32210 and 926-32211) were applied in 1:15,000 dilution. Imaging were performed by LI-COR Odyssey CLx system.

SEM and TEM. sEV-bead complex was resuspended in 200 µL cold PBS solution. For electron microscope evaluation, EV-bead complexes were washed with pure water followed by the fixation in a 2% EMS-quality paraformaldehyde aqueous solution. 5 µL of sEV-bead mixtures were added to cleaned silicon chips and immobilized after drying EVs under a ventilation hood. Samples on silicon chips were mounted on a SEM stage by carbon paste. A coating of gold-palladium alloy was applied to improve SEM image background. SEM was performed under low beam energies (7 kV) on Hitachi SU8230 filed emission scanning electron microscope. For TEM, ~5 µL of each sEV-beads complex was left to adhere onto formvar carbon coated copper Grid 200 mesh (Electron Microscopy Sciences) for 5 mins followed by 5 mins of negative staining with 2% aqueous uranyl acetate. Excess liquids were blotted by filter papers. Total grid preparation was performed at room temperature till totally air-dried under a ventilation hood for 25 mins. Images were acquired on the same day at 75 kV using Hitachi H-8100 transmission electron microscope.

In vivo biodistribution analysis. The human bladder cancer cell line HTB-9 (ATCC, 5637) and the negative control of human embryonic kidney epithelial cell line HEK293 (ATCC, CRL-1573) were cultured in DMEM and MEM respectively, supplemented with 10% normal FBS and 1% penicillin/streptomycin. Once the cell cultures reached ~70% confluency, the media was replaced with fresh media containing 10% exosome-depleted FBS (Thermo Fisher, A2720803). The cells were cultured for an additional 72 h before the conditioned media were collected.

sEVs were isolated using Nanopoms approach. sEVs were incubated with 1 mM fluorescent lipophilic tracer DiR (1,1-dioctadecyl-3,3,3,3-tetramethylindotricarbocyanine iodide) (Invitrogen, D12731) at room temperature (RT) for 15 minutes. DiR-labelled sEVs or free DiR dyes were segregated using Amicon Ultra-15 Centrifugal Filter method. The $2.0\times10^9$ particles/ml of isolated sEVs measured via NTA were used for each mouse injection. The 6- to 8-week-old female BALB/cJ mice were used. The animal IACUC protocols have been approved by the University of Kansas Institutional Animal Care and Use Committee with protocol number 258-01 and operated in the KU Animal Care Unit. Freshly purified DiR-labelled sEVs were injected through the tail vein for intravenous (i.v.) injection. The In-Vivo Systems (Bruker, USA) with high-sensitive CCD camera was used for collecting fluorescence, luminescence and X-ray images. Isoflurane sedated live mice were taken fluorescence and X-ray images prior to the animals were sacrificed, then main organs (brain, heart, lung, liver, kidney and spleen) were harvested for fluorescence imaging in 3 mins (excitation 730 nm, emission 790 nm), X-ray imaging (120 mm FOV, 1 min) and luminescence imaging (90 fov, 0.2 sec) at 24 h, 48 h and 72 h time points, respectively. The data were analyzed using the Bruker MI software.

Supplemental Materials

Nanographene Fabricated Nano Pom Poms for Robust Preparation of Small Extracellular Vesicles Assisting Precision Cancer Diagnosis and Therapeutics Characterization of Nanopoms Immunomagnetic Particles for Specific Capture and Release of sEVs from a Variety of Biological Fluids.

As shown in FIG. 18, the optimization of NanoPoms particles concentration used for isolating sEVs from 1 mL milk solution, characterized by the Pierce BCA Protein Assay. The five repetitive measurements were performed for each data point with RSD<~5% (n=5). With increasing the amount of capture beads in 1 mL biofluids, more EVs were isolated to gradually reach to the maximum. Once the available capture binding sites on the bead surface excess the number of overall EVs, the increase of beads amount does not influence on the overall EV capture amount. Thus, the 1 mg/mL of NanoPoms capture particles were used for appropriate capture efficiency ranging from ~$10^8$ to ~$10^{13}$ particles/mL.

3. NGS Analysis of Urinary EV Small RNAs

Bioinformatics Analysis: The sequences of precursor miRNA, tRNA, snRNA, snoRNA, scaRNA, rRNA, scRNA, vaultRNA, lncRNA, miscRNA, pseudogenes, retained introns, ribozymes and transcribed unprocessed pseudogenes were extracted from RefSeq (hg38) and GENCODE (v29) to build a customized database. We refer to this database as the customized ncRNA database. For further quantifying mature miRNA abundance, their sequences were extracted from miRBase (ver. hg38) to form another database, which is refer to as the mature miRNA database. Initial quality assessment of the reads was performed using the FASTQC (www.bioinformatics.babraham.ac.uk/projects/fastqc/) package. Cutadapt was used to trim the 5' (GUUCAGAGUUCUACAGUCCGACGAUC, SEQ ID NO:66) and 3' (AACTGTAGGCACCATCAAT, SEQ ID NO:67) adaptor sequences from the sequences. The unique molecular indices (UMI) sequences in the QIAseq libraries were further trimmed using FASTP (--umi_loc=read1--umi_len=12). The trimmed reads were filtered with a minimum length of 15 nt. Mapping to the mature miRNA database and customized non-ncRNA database was performed using BWA (bwa-aln). We relaxed the BWA parameter to allow each read to mapped to at most 100 locations, accounting for the numerous multi-mapping cases induced by the short-read length of the sequencing reads. To ensure maximum accuracy, we further restrict perfect sequence in TABLE s1

Comparative analysis of cost, time, steps, and performance between EV isolation methods.

| EV Isolation Methods | NanoPoms | Ultracentrifugation | Chromatographic Column | Polymer Precipitation |
|---|---|---|---|---|
| Cost | Low, no instrument required | High, very expensive equipment cost | Low | Low |
| Protocol duration | ~4 hrs | ~12 hrs | ~6 hrs | ~6 hrs |
| Processing capacity | From ~µL to L | ~12-500 mL | ~150 µL-100 mL (IZON) | ~≤1 mL ExoQuick™ |
| Subtype specificity | Surface marker defined specificity to subtypes | No | No | No |
| Purity | High to pathogenic EVs | Mixture of EV populations | Mixture of EV populations | Mixture of EV with protein aggregates |
| Reproducibility | High | Low | — | — |
| Scalability | Yes | No | Yes | No |

NanoPoms Prepared sEVs for Droplet Digital PCR Analysis with Substantially Improved Detection Specificity and Sensitivity.

As shown in FIG. 20, both EGFR (Thr790Met) and TERT (C228T and C250T) mutations were detected, but the detection efficiency was 3-fold higher from NanoPoms isolated sEV DNAs as compared to UC approach. As shown in FIG. 21, the ddPCR analysis of NanoPoms isolated sEV DNAs showed the EGFR heterozygosity in the three bladder cancer patients. In contrast, UC isolated EV DNAs from the same sample input did not detect the EGFR heterozygosity in patient 2 and patient 3. The DNA copy number was substantially lower in UC prepared EV DNAs as compared to NanoPoms.

seeding (by setting –k=0). All other parameters were used as default. With an in-house script, we counted the read mapping to quantify the expression level of each ncRNA gene and the abundance of each mature miRNA. For multi-mapping, we evenly distributed its abundances to all mapped locations. The mapping results against the customized ncRNA database were used to quantify different types of ncRNAs as the Pie charts (refer pie-chart figures here). The mapping results against the mature miRNA database were summarized as the volcano plot (refer volcano plot here). The mapping results were further analyzed using the Deseq2 to reveal significantly different abundant miRNAs. The most significant 100 miRNAs were further selected to generate the heatmap (shown below).

TABLE s2

The distribution of small RNAs from urinary EV isolated by UC and NanoPoms.

| % | tRNA | lncRNA | miRNA | snRNA | snoRNA | miscRNA | rRNA | scaRNA |
|---|---|---|---|---|---|---|---|---|
| UC-BC Urine EVs | 64.35 | 18.89 | 12.40 | 1.92 | 0.18 | 0.50 | 1.39 | 0.01 |
| Nano-Wing-BC Urine EVs | 47.52 | 42.02 | 4.94 | 1.41 | 0.29 | 0.89 | 1.98 | 0.07 |
| UC-Healthy Urine EVs | 69.88 | 14.68 | 8.59 | 4.66 | 0.23 | 0.46 | 1.09 | 0.01 |
| Nano-Wing-Healthy Urine EVs | 49.62 | 42.10 | 4.19 | 1.16 | 0.38 | 0.51 | 0.85 | 0.01 |

| % | Mt-tRNA | Mt_rRNA | scRNA | vaultRNA | sRNA | Other |
|---|---|---|---|---|---|---|
| UC-BC Urine EVs | 0.02 | 0.002 | 0.00 | 0.004 | 0.001 | 0.34 |
| Nano-Wing-BC Urine EVs | 0.03 | 0.01 | 0.00 | 0.002 | 0.001 | 0.82 |
| UC-Healthy Urine EVs | 0.003 | 0.003 | 0.00 | 0.003 | 0.001 | 0.38 |
| Nano-Wing-Healthy Urine EVs | 0.03 | 0.01 | 0.00 | 0.002 | 0.001 | 1.14 |

TABLE s3

The top 10 highly enriched miRNAs identified from NanoPoms isolated urinary EVs as compared with UC.

| Genes | Log2 Fold Change | p value | Reported signaling pathway/functions |
|---|---|---|---|
| hsa-miR-3168 | 5.140358266 | 1.38E−07 | KRAS-dependent sorting to exosomes from colorectal cancer cell lines<br>Known Melanoma mature miRNA |
| hsa-miR-92b-5p | 4.358349687 | 1.08E−06 | Cancer metastasis<br>Promote EMT in bladder cancer migration |
| hsa-miR-891a-5p | −5.329381923 | 1.19E−06 | Prognostic marker for HR-positive breast cancer |
| hsa-miR-6785-5p | 5.063745282 | 1.80E−06 | miRNA target genes in the TP53 signaling pathway in tumor |
| hsa-miR-934 | −4.078662275 | 3.10E−06 | Cancer metastasis, exosomal oncogene<br>Non-coding RNA with neurogenic function |
| hsa-miR-6883-3p | 4.420682437 | 5.64E−06 | Target CDK4/6 in colon cancer cells |
| hsa-miR-3202 | 5.039882582 | 8.31E−06 | Regulating TLR signaling pathway<br>Promoted Cell Apoptosis |
| hsa-miR-3648 | −4.682609314 | 1.30E−05 | Promote invasion and metastasis of human bladder cancer<br>Regulate cell proliferation |
| hsa-miR-6802-5p | 4.168335059 | 1.84E−05 | Exosomal regulatory miRANs<br>Heart disease |
| hsa-miR-6763-5p | 4.0778099 | 2.21E−05 | Immunity Regulation |

As shown in FIG. 24, the disease group can be significantly differentiated from healthy group regardless if the light release process was implemented.

4. Proteomic Analysis of Urinary EV Proteins

Urinary EV pellets resultant from ~2 mL of urine from both bladder cancer patients and healthy individuals were reconstituted in 400 µL of M-PER Mammalian Protein Extraction Buffer (Thermo) supplemented with 1× Halt Protease Inhibitors (Thermo) and sonicated in an ultrasonic water bath for 15 min. Lysates were exchanged into ~40 µL of 100 mM triethylammonium bicarbonate using Amicon Ultra-0.5, 3 k columns (Millipore). Lysate were digested overnight with Trypsin Gold, Mass Spectrometry Grade (Promega). Peptides were finally reconstituted into 0.1% formic acid to a concentration of 0.1 µg/µL and injected into a 1260 Infinity nHPLC (Agilent) with separation from a Jupiter C-18 column, 300 Å, 5 µm, Phenomenex) in line with a LTQ XL ion trap mass spectrometer equipped with a nano-electrospray source (Thermo). All fragmentation data were collected in CID mode. The nHPLC was configured with binary mobile phases that included 10 min at 5% of 0.1% formic acid and 85% acetonitrile, 180 min (LTQ XL), 5 min wash using 70% of 0.1% formic acid, 85% acetonitrile, and 10 min equilibrate. Samples were performed in duplicate for obtaining the average values utilized for analysis. Searches were performed with UniRef100 database which includes common contaminants from digestion enzymes and human keratins. Peptides were filtered and quantified using ProteoIQ (Premierbiosoft, Palo Alto, Calif.).

TABLE S4

The 10 unique gene products identified from BC patient only and 4 unique genes identified from healthy control group only, by proteomic analysis of NanoPoms isolated urinary EV proteins. The Human Protein Atlas database was used: www.proteinatlas.org/

| BC Patient | FASTA Title Lines | Reported Functions and Pathways |
| --- | --- | --- |
| ARMCX4 | \|Q5H9R4\|ARMX4__HUMAN Armadillo repeat-containing X-linked protein 4 | Intracellular, Nucleoplasm and additionally in Vesicles<br>Prognostic marker, novel passenger cancer genes |
| DSC3 | \|Q14574\|DSC3__HUMAN Desmocollin-3 | Plasma membrane, Cell Junctions<br>Regulated by p53 signaling pathway in colorectal cancer<br>Down-regulated in primary breast tumors |
| IRAK4 | \|Q9NWZ3\|IRAK4__HUMAN Interleukin-1 receptor-associated kinase 4 | Intracellular, Microtubules and additionally in Nucleoli, Cytosol<br>Prognostic marker in endometrial cancer and urothelial cancer<br>Disrupts inflammatory pathways and delays tumor development |
| KRT23 | \|Q9C075\|K1C23__HUMAN Keratin, type I cytoskeletal 23 | Intracellular, Intermediate filaments and additionally in Cytosol<br>Prognostic marker in urothelial cancer<br>Keratin 23 promotes telomerase reverse transcriptase expression and human colorectal cancer growth |
| PIGQ | \|Q9BRB3\|PIGQ__HUMAN Phosphatidylinositol N-acetylglucosaminyltransferase subunit Q | Golgi apparatus, Vesicles and additionally in Nucleoplasm<br>Prognostic marker in renal cancer<br>GPI-AP biosynthesis deficiency disorder syndrome |
| SERPINB2 | \|P05120\|PAI2__HUMAN Plasminogen activator inhibitor 2 | Intracellular<br>Prognostic marker in urothelial cancer<br>SerpinB2 inhibits migration and promotes a resolution phase signature in large peritoneal macrophages |
| PDHA2 | \|P29803\|ODPAT__HUMAN Pyruvate dehydrogenase E1 component subunit alpha, testis-specific form, mitochondrial | Intracellular, Mitochondria, links the glycolytic pathway to the tricarboxylic cycle<br>Testis specific<br>In Tumor Suppressor gene database https://bioinfo.uth.edu/TSGene/, |
| RALGAPA2 | \|Q2PPJ7\|RGPA2__HUMAN Ral GTPase-activating protein subunit alpha-2 | Intracellular, Plasma membrane, Cytosol<br>Prognostic marker in renal cancer<br>Downregulation of Ral GTPase-activating protein promotes tumor invasion and metastasis of bladder cancer |
| SMARCD3 | \|Q6STE5\|SMRD3__HUMAN SWI/SNF-related matrix-associated actin-dependent regulator of chromatin subfamily D member 3 | Intracellular, Nucleoplasm<br>Prognostic marker in colorectal cancer<br>The chromatin remodeler SMARCD3 regulates cell cycle progression and its expression predicts survival outcome in ER+ breast cancer |
| PAPD7 | \|Q5XG87\|PAPD7__HUMAN Non-canonical poly(A) RNA polymerase | Intracellular, Nucleoplasm and additionally in Nuclear membrane, Golgi apparatus<br>Prognostic marker in renal cancer and urothelial cancer |
| Healthy | FASTA Title Lines | Reported Functions and Pathways |
| ORM2 | \|P19652\|A1AG2__HUMAN Alpha-1-acid glycoprotein 2 | Intracellular, Vesicles and additionally in Golgi apparatus<br>Orm1 and Orm2 are conserved endoplasmic reticulum membrane proteins regulating lipid homeostasis and protein quality control |
| ATP5F1A | \|P25705\|ATPA__HUMAN ATP synthase subunit alpha, mitochondrial | Intracellular, Mitochondria<br>Reduced Levels of ATP Synthase Subunit ATP5F1A Correlate with Earlier-Onset Prostate Cancer |
| DEFB1 | \|P60022\|DEFB1__HUMAN Beta-defensin 1 | Secreted pathway<br>Normal tissue annotation |
| MPP7 | \|Q5T2T1\|MPP7__HUMAN MAGUK p55 subfamily member 7 | Intracellular, Cell Junctions and additionally in Nucleoplasm<br>Acts as an important adapter that promotes epithelial cell polarity and tight junction formation via its interaction with DLG1. Involved in the assembly of protein complexes at sites of cell-cell contact |

The invention claimed is:

1. A method for capture and photorelease of extracellular vesicles from a test sample suspected of containing one or more target extracellular vesicles, comprising:

contacting said test sample with a plurality of immunomagnetic particles in a test container to create a first assay mixture, said immunomagnetic particles each comprising:

a central magnetic particle comprising a core particle having a surface; a graphene-oxide-layer coating said core particle, said graphene-oxide layer comprising graphene-oxide nanosheets, said graphene-oxide nanosheets being covalently bonded to the particle surface; and at least one polydopamine polymer coupled with the graphene-oxide nanosheets, a targeting moiety coupled to the at least one polydopamine polymer, and a photocleavable linker, said photocleavable linker connecting said magnetic particle and said targeting moiety, wherein said target extracellular vesicles, if present, are bound by said targeting moiety to create an immunomagnetic complex;

magnetically immobilizing said immunomagnetic complexes at a first location in said container;

washing said first assay mixture and resuspending said magnetically immobilized immunomagnetic complexes in solution to create a second assay mixture;

exposing said immunomagnetic complexes to activating radiation to cleave said photocleavable linker, wherein said target extracellular vesicles are released from said immunomagnetic complex to yield released extracellular vesicles and released immunomagnetic particles;

magnetically immobilizing said released immunomagnetic particles at a second location in said container, wherein said released target extracellular vesicles remain suspended in the second assay mixture; and isolating said released target extracellular vesicles from the second assay mixture, and optionally separately recovering said released immunomagnetic particles.

2. The method of claim 1, wherein said test sample is selected from a biological fluid selected from the group consisting of cell culture medium, tissue fluid, urine, milk, saliva, serum, plasma, blood, cerebrospinal fluid, nasal secretions, exhaled breath condensate, tears, adipose tissue, seminal fluid, vaginal secretions, synovial fluid, pleural fluid (pleural lavage), pericardial fluid, peritoneal fluid, amniotic fluid, otic fluid, gastric fluid, placental fluid, breast milk, Perilymph fluid, ascitic fluid, and combinations thereof.

3. The method of claim 1, wherein said first or second assay mixture comprises water or buffer system selected from the biological buffer consisting of, but not limited to, phosphate buffered saline, HEPES (4-(2-hydroxyethyl)-1-piperazineethanesulfonic acid), MOPS, Bis-Tris, MOPSO, ADA, ACES, PIPES, BES, TES, MOBS, and mixtures thereof.

4. The method of claim 1, wherein said assay volume ranges from 1 µL to 10 L.

5. The method of claim 1, wherein said targeting moiety is selected from the group consisting of antibodies, aptamers, antigenic peptides, tissue targeting/penetration peptides, MEW binding peptides, neoantigens, phage displayed epitopes, nucleic acid oligos, enzyme, receptors, inhibitors, and combinations thereof.

6. The method of claim 1, wherein the photocleavable linkage comprises biotin.

7. The method of claim 1, wherein said test container is selected from the group consisting of microfluidics chambers, test tubes, centrifuge tubes, microtubes, beakers, vials, flasks, bottles, ELISA well plate, 6-well, 12-well, 24-well, 48-well, 96-well, or 384-well plates, and cell culture containers.

8. The method of claim 1, wherein said immunomagnetic particles have a diameter of 5 nm or greater.

9. The method of claim 1, further comprising detecting one or more biomarkers, or multi-omic analysis in said released target extracellular vesicles.

10. The method of claim 9, further comprising rendering a diagnosis based upon said one or more biomarkers.

11. The method of claim 10, wherein said diagnosis is a cancer diagnosis, wherein said method is repeated over time, said method further comprising monitoring the progression of said cancer over time.

12. The method of claim 10, wherein said diagnosis is a cancer diagnosis, wherein said method is repeated after treatment for said diagnosis, said method further comprising monitoring the effect said treatment of said cancer.

13. The method of claim 9, said assay having high sensitivity for said one or more biomarkers.

14. The method of claim 9, wherein said biomarkers are selected from the group consisting of nucleic acids, proteins, peptides, enzymes, inhibitors, lipids, metabolites, cytokines, stimulating factors, hormones, fragments thereof, and mutated forms thereof.

15. The method of claim 10, wherein said diagnosis is a specific genetic mutation, or expression level changes of a biomarker or downstream product thereof, such as mRNA, miRNA, proteins, and peptides.

16. The method of claim 1, wherein said released target extracellular vesicles comprise a surface modified with one or more of said targeting moieties, said targeting moieties remaining bound to said target extracellular vesicles after said release.

17. The method of claim 16, wherein said targeting moieties are active agents.

18. The method of claim 1, wherein said container is a microfluidic mixing channel, wherein said magnetically immobilizing said immunomagnetic complexes at a first location comprises applying a magnetic field within a microfluidic chamber, and wherein after photolytically releasing said immunomagnetic particles and said target extracellular vesicles, said magnetically immobilizing said released immunomagnetic particles at a second location comprises immobilizing said released immunomagnetic particles in a microfluidic chamber, wherein said released target extracellular vesicles are washed downstream to an outlet of the microfluidic mixing channel.

19. A composition comprising a plurality of released target extracellular vesicles prepared according to claim 1, wherein said released target extracellular vesicles each comprise a surface modified with one or more of said targeting moieties, said targeting moieties remaining bound to said target extracellular vesicles after said release, wherein said target extracellular vesicles remain intact after said release, wherein said targeting moieties are active agents.

20. The composition of claim 19, wherein said active agents are therapeutic or diagnostic nucleic acids, drugs, small molecule compounds, chemotherapeutics, stimulating factors, binding peptides, and/or antigens.

21. A method of treatment or diagnosis comprising administering to a subject in need thereof, a composition according to claim 19.

22. The method of claim 21, wherein said targeting moieties are released from said target extracellular vesicles before administering said target extracellular vesicles to said subject.

23. A composition comprising a plurality of released target extracellular vesicles prepared according to claim 1, wherein said released target extracellular vesicles each comprise a surface modified with one or more of said targeting moieties, said targeting moieties having been released from said target extracellular vesicles, wherein said target extracellular vesicles remain intact after said release.

* * * * *